(12) United States Patent
Walker et al.

(10) Patent No.: US 12,082,975 B2
(45) Date of Patent: Sep. 10, 2024

(54) METHODS, SYSTEMS AND COMPUTER PROGRAM PRODUCTS FOR ULTRASOUND IMAGING USING COHERENCE CONTRIBUTION

(71) Applicant: Duke University, Durham, NC (US)

(72) Inventors: William Walker, Chapel Hill, NC (US); Matthew Morgan, Durham, NC (US); Gregg Trahey, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 359 days.

(21) Appl. No.: 17/284,860

(22) PCT Filed: Oct. 18, 2019

(86) PCT No.: PCT/US2019/056981
§ 371 (c)(1),
(2) Date: Apr. 13, 2021

(87) PCT Pub. No.: WO2020/081962
PCT Pub. Date: Apr. 23, 2020

(65) Prior Publication Data
US 2021/0386404 A1   Dec. 16, 2021

Related U.S. Application Data

(60) Provisional application No. 62/748,055, filed on Oct. 19, 2018.

(51) Int. Cl.
*A61B 8/08* (2006.01)
*A61B 8/06* (2006.01)
*G01S 7/52* (2006.01)

(52) U.S. Cl.
CPC .............. *A61B 8/5207* (2013.01); *A61B 8/06* (2013.01); *A61B 8/488* (2013.01); *G01S 7/52036* (2013.01)

(58) Field of Classification Search
CPC ......... A61B 8/5207; A61B 8/06; A61B 8/488; G01S 7/52036
See application file for complete search history.

(56) References Cited

U.S. PATENT DOCUMENTS 5,924,986 A * 7/1999 Chandler ............ G01S 7/52017
600/407
2006/0173313 A1 * 8/2006 Liu ...................... G01S 15/8993
600/437

(Continued)

FOREIGN PATENT DOCUMENTS

CN         102549450 B     2/2014

OTHER PUBLICATIONS

International Search Report and Written Opinion for PCT/US149/56981, mailed Jan. 14, 2020, 9 pages.

(Continued)

*Primary Examiner* — John D Li
(74) *Attorney, Agent, or Firm* — Myers Bigel, P.A.

(57) ABSTRACT

An ultrasound system for imaging a target is provided. The system includes a plurality of transducer elements; at least one transmitter configured to excite at least one of the transducer elements to emit ultrasound energy to the target; a plurality of samplers configured to sample echo signals received by at least some of the plurality of transducer elements, the echo signals comprising acoustic echoes received from the target responsive to the ultrasound energy; a coherence calculator configured to calculate a plurality of coherence values, each of the coherence values corresponding to a measure of similarity between at least two sample echo signals; an estimator configured to estimate a coherence contribution estimate, the coherence contribution estimate comprising an estimate of a contribution of at least one coherence model to the plurality of coherence values.

26 Claims, 28 Drawing Sheets

(56) References Cited

U.S. PATENT DOCUMENTS

| | | | |
|---|---|---|---|
| 2014/0276065 A1* | 9/2014 | He | A61B 8/0891 600/445 |
| 2015/0342567 A1* | 12/2015 | Ustuner | A61B 8/5207 600/447 |
| 2017/0061217 A1* | 3/2017 | Cha | G06F 18/2415 |
| 2017/0209121 A1* | 7/2017 | Davis, Sr. | A61B 8/4494 |

OTHER PUBLICATIONS

Bell, et al., "Improved Visualization of Endocardial Borders with Short-Lag Spatial Coherence Imaging of Fundamental and Harmonic Ultrasound Data", 2012 IEEE International Ultrasonics Symposium. Dresden, Germany, 2012, 2129-2132.
Bell, et al., "Resolution and Brightness Characteristics of Short-Lag Spatial Coherence (SLSC) Images", IEEE Transactions on Ultrasonics, Ferroelectrics, and Frequency Control, 62(7), 2015, 1265-1276.
Bell, et al., "Short-Lag Spatial Coherence Imaging of Cardiac Ultrasound Data: Initial Clinical Results", Ultrasound in Medicine & Biology, 39(10), 2013, 1861-1874.
Bottenus, et al., "Acoustic reciprocity of spatial coherence in ultrasound imaging", IEEE Transactions on Ultrasonics, Ferroelectrics, and Frequency Control, 62(5), 2015, 852-861.
Bottenus, et al., "Synthetic Aperture Focusing for Short-Lag Spatial Coherence Imaging", IEEE Transactions on Ultrasonics, Ferroelectrics, and Frequency Control, 60(9), 2013, 1816-1826.
Camacho, et al., "Phase Coherence Imaging", IEEE Transactions on Ultrasonics, Ferroelectrics, and Frequency Control, 56(5), 2009, 958-974.
Dahl, et al., "Harmonic Spatial Coherence Imaging: An Ultrasonic Imaging Method Based on Backscatter Coherence", IEEE Transactions on Ultrasonics, Ferroelectrics, and Frequency Control, 59(4), 2012, 648-659.
Dahl, et al., "Lesion Detectability in Diagnostic Ultrasound with Short-Lag Spatial Coherence Imaging", Ultrasonic Imaging, 33(2) (Author Manuscript), 2011, 119-133.
Hyun, et al., "Efficient Strategies for Estimating the Spatial Coherence of Backscatter", IEEE Transactions on Ultrasonics, Ferroelectrics, and Frequency Control, 64(3), 2017, 500-513.
Hyun, et al., "Short-Lag Spatial Coherence Imaging on Matrix Arrays, Part I: Beamforming Methods and Simulation Studies", IEEE Transactions on Ultrasonics, Ferroelectrics, and Frequency Control, 61(7), 2014, 1101-1112.
Jakovljevic, et al., "In Vivo Application of Short-Lag Spatial Coherence Imaging in Human Liver", Ultrasound in Medicine & Biology, 39(3), 2013, 534-542.
Jakovljevic, et al., "Short-Lag Spatial Coherence Imaging on Matrix Arrays, Part II: Phantom and In Vivo Experiments", IEEE Transactions on Ultrasonics, Ferroelectrics, and Frequency Control, 61(7), 2014, 1113-1122.
Kakkad, et al., "In Vivo Application of Short-Lag Spatial Coherence and Harmonic Spatial Coherence Imaging in Fetal Ultrasound", Ultrasonic Imaging, 37(2) (Author Manuscript), 2015, 101-116.
Lediju, et al., "Short-Lag Spatial Coherence of Backscattered Echoes: Imaging Characteristics", IEEE Transactions on Ultrasonics, Ferroelectrics, and Frequency Control, 58(7), 2011, 1377-1388.
Li, et al., "Adaptive Imaging Using the Generalized Coherence Factor", IEEE Transactions on Ultrasonics, Ferroelectrics, and Frequency Control, 50(2), 2003, 128-141.
Long, et al., "Clinical Utility of Fetal Short-Lag Spatial Coherence Imaging", Ultrasound in Medicine & Biology, 44(4), 2018, 794-806.
Long, et al., "Spatial Coherence in Medical Ultrasound: A Review", Ultrasound in Medicine & Biology, 48(6), 2022, 975-996.
Nilsen, et al., "Wiener Beamforming and the Coherence Factor in Ultrasound Imaging", IEEE Transactions on Ultrasonics, Ferroelectrics, and Frequency Control, 57(6), 2010, 1329-1346.
O'Donnell, et al., "Optimum Displacement for Compound Image Generation in Medical Ultrasound", IEEE Transactions on Ultrasonics, Ferroelectrics, and Frequency Control, 35(4), 1988, 470-476.
Oliver, B.M., "Sparkling Spots and Random Diffraction", Proceedings of the IEEE 51.1, 1963, 220-221.
Ophir, et al., "Elastography: Ultrasonic Estimation and Imaging of the Elastic Properties of Tissues", Proceedings of the Institution of Mechanical Engineers, Part H: Journal of Engineering in Medicine, 213(3), 1999, 203-233.
Petersen, Kaareb., "The Matrix Cookbook", Technical University of Denmark, 7(15), 2008, (72 pages).
Pinton, et al., "Rapid Tracking of Small Displacements with Ultrasound", IEEE Transactions on Ultrasonics, Ferroelectrics, and Frequency Control, 53(6), 2006, 1103-1117.
Pinton, et al., "Sources of Image Degradation in Fundamental and Harmonic Ultrasound Imaging Using Nonlinear, Full-Wave Simulations", IEEE Transactions on Ultrasonics, Ferroelectrics, and Frequency Control, 58(4), 2011, 754-765.
Pinton, et al., "Spatial Coherence in Human Tissue: Implications for Imaging and Measurement", IEEE Transactions on Ultrasonics, Ferroelectrics, and Frequency Control, 61(12), 2014, 1976-1987.
Prieur, et al., "Signal Coherence and Image Amplitude with the Filtered Delay Multiply and Sum Beamformer", IEEE Transactions on Ultrasonics, Ferroelectrics, and Frequency Control, 65(7), 2018, 1133-1140.
Rayleigh, Lord, "XII. On the Resultant of a Large No. of Vibrations of the Same Pitch and of Arbitrary Phase", The London, Edinburgh, and Dublin Philosophical Magazine and Journal of Science, 10(60), 1880, 73-78.
Sarvazyan, et al., "Shear Wave Elasticity Imaging: A New Ultrasonic Technology of Medical Diagnostics", Ultrasound in Medicine & Biology, 24(9), 1998, 1419-1435.
Sasso, et al., "Medical ultrasound imaging using the fully adaptive beamformer", IEEE International Conference on Acoustics, Speech, and Signal Processing, vol. 2, 2005, II-489-II-492.
Savord, et al., "Fully sampled matrix transducer for real time 3D ultrasonic imaging", IEEE Symposium on Ultrasonics, vol. 1. Honolulu, Hawaii, 2003, 945-953.
Schmidt, Ralpho., "Multiple Emitter Location and Signal Parameter Estimation", IEEE Transactions on Antennas and Propagation, 34(3), 1986, 276-280.
Shin, et al., "Spatial Prediction Filtering of Acoustic Clutter and Random Noise in Medical Ultrasound Imaging", IEEE Transactions on Medical Imaging, 36(2), 2017, 396-406.
Synnevag, et al., "Benefits of Minimum-Variance Beamforming in Medical Ultrasound Imaging", IEEE Transactions on Ultrasonics, Ferroelectrics, and Frequency Control, 56(9), 2009, 1868-1879.
Torp, et al., "Optimum beamformer strategy for detecting signals in clutter noise", IEEE International Ultrasonics Symposium (IUS). Taipei, Taiwan, 2015, (4 pages).
Trahey, et al., "A quantitative approach to speckle reduction via frequency compounding", Ultrasonic Imaging, 8(3), 1986, 151-164.
Trahey, et al., "Speckle pattern correlation with lateral aperture translation: Experimental results and implications for spatial compounding", IEEE Transactions on Ultrasonics, Ferroelectrics, and Frequency Control, 33(3), 1986, 257-264.
Verdet, E., "Étude sur la constitution de la lumière non polarisée et de la lumière partiellement polarisée (Study on the Constitution of Non-Polarized and Partially Polarized Light)", Annales scientifiques de l'É.N.S. 1re série, vol. 2, 1865, 291-316.
Viola, et al., "Adaptive Signal Processing in Medical Ultrasound Beamforming", IEEE Ultrasonics Symposium, 4(4), 2005, 1980-1983.
Wagner, et al., "Fundamental Correlation Lengths of Coherent Speckle in Medical Ultrasonic Images", IEEE Transactions on Ultrasonics, Ferroelectrics, and Frequency Control, 35(1), 1988, 34-44.
Wagner, et al., "Statistics of Speckle in Ultrasound B-Scans", IEEE Transactions on Sonics and Ultrasonics, 30(3), 1983, 156-163.
Wagner, et al., "Unified Approach To The Detection And Classification Of Speckle Texture In Diagnostic Ultrasound", Optical Engineering, 25(6) (Author Manuscript), 1986, 738-742.

(56) References Cited

OTHER PUBLICATIONS

Wang, et al., "SNR-Dependent Coherence-Based Adaptive Imaging for High-Frame-Rate Ultrasonic and Photoacoustic Imaging", IEEE Transactions on Ultrasonics, Ferroelectrics, and Frequency Control, 61(8), 2014, 1419-1432.

Wildes, et al., "Elevation Performance of 1.25D and 1.5D Transducer Arrays", IEEE Transactions on Ultrasonics, Ferroelectrics, and Frequency Control, 44(5), 1997, 1027-1037.

\* cited by examiner

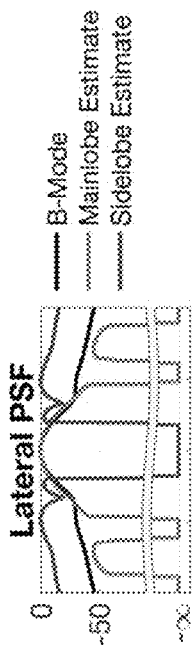
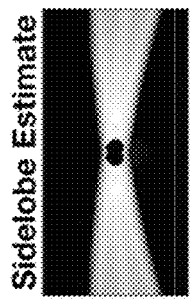
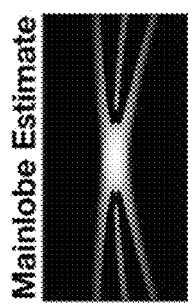
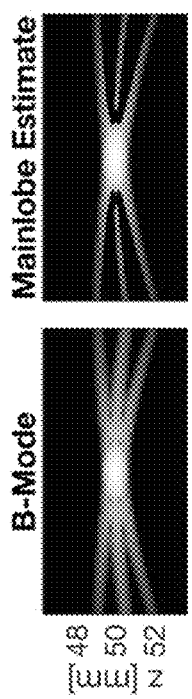
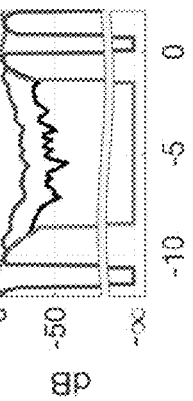
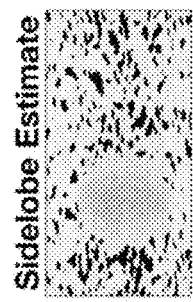
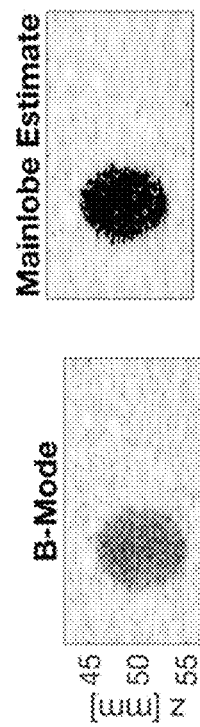
FIG. 19A  FIG. 19B  FIG. 19C  FIG. 19D
FIG. 19E  FIG. 19F  FIG. 19G  FIG. 19H

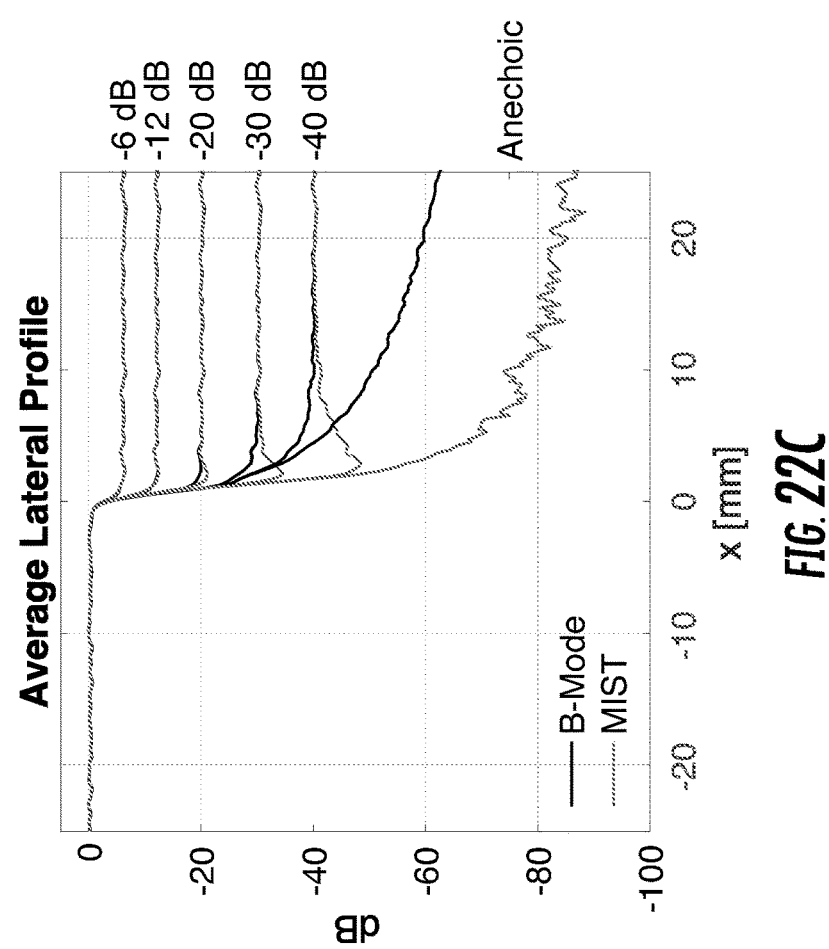
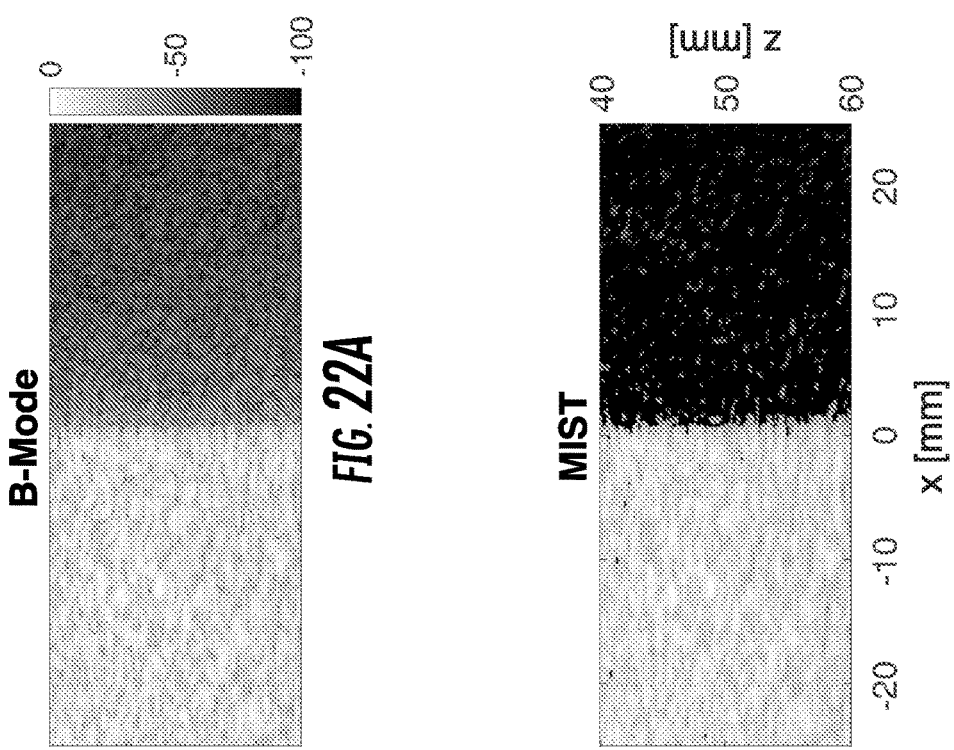
FIG. 22A  FIG. 22B  FIG. 22C

FIG. 23B
FIG. 23C
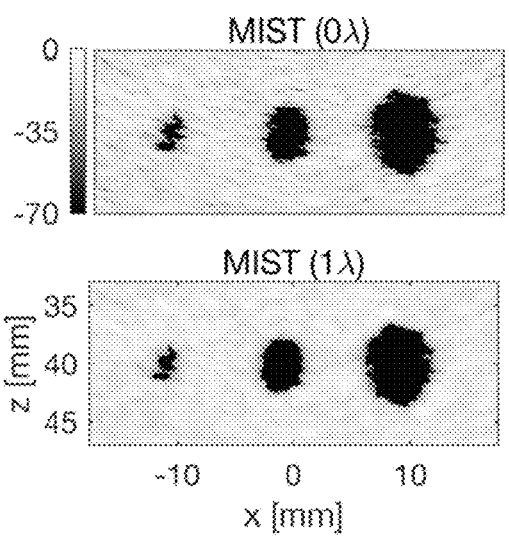

FIG. 23E
FIG. 23F
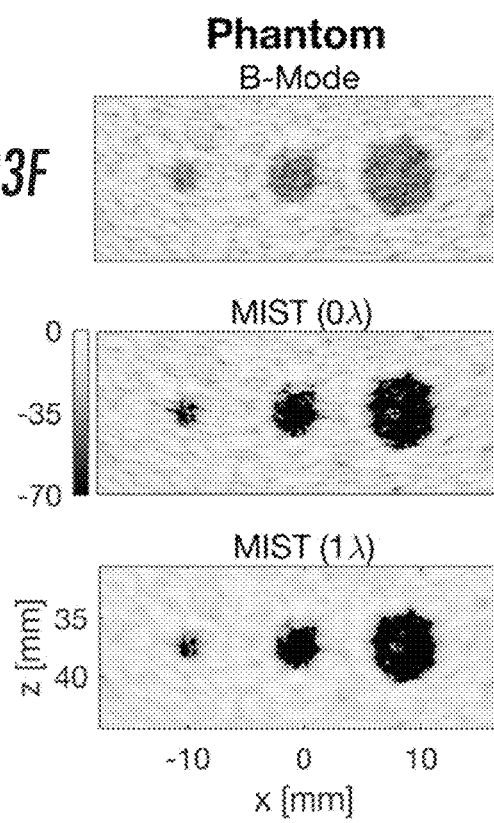
FIG. 23G
FIG. 23H

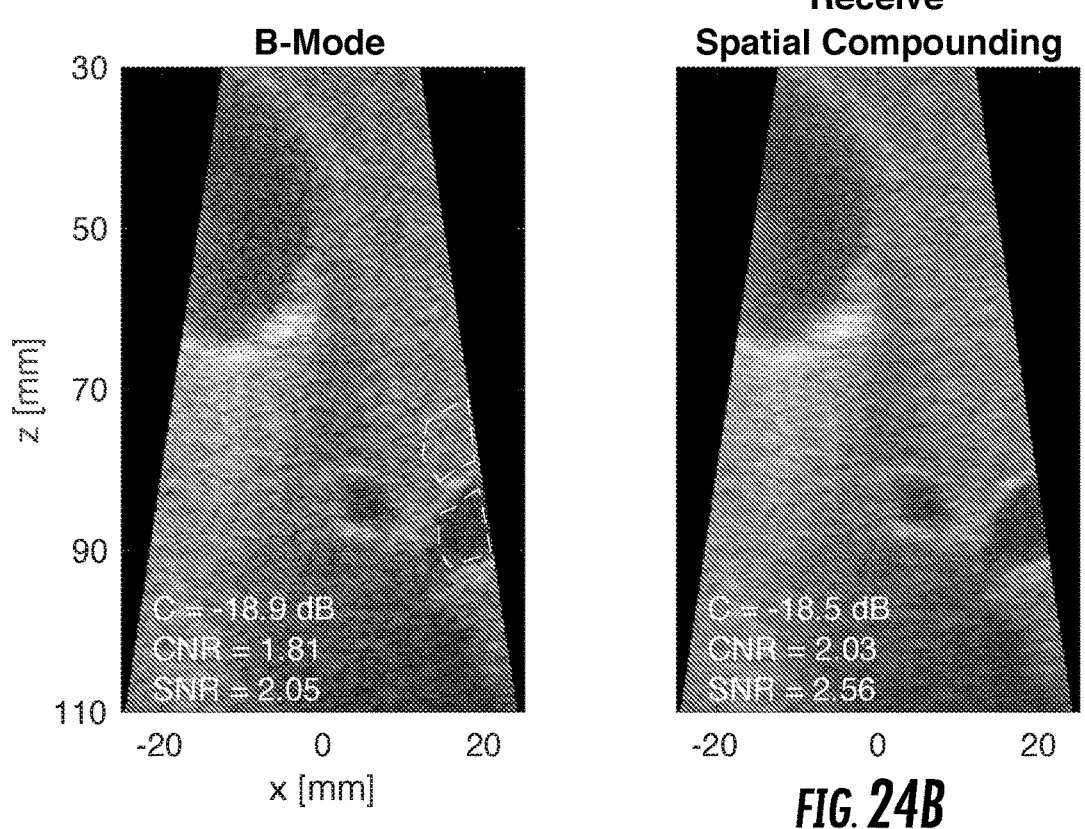
FIG. 24A
FIG. 24B
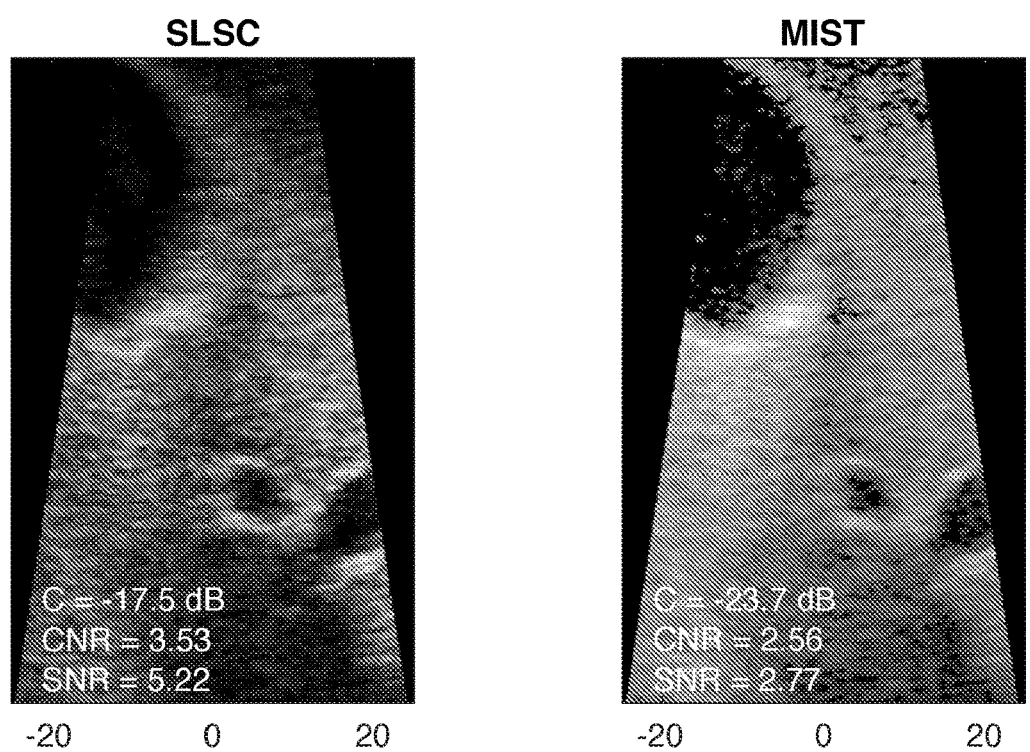
FIG. 24C
FIG. 24D

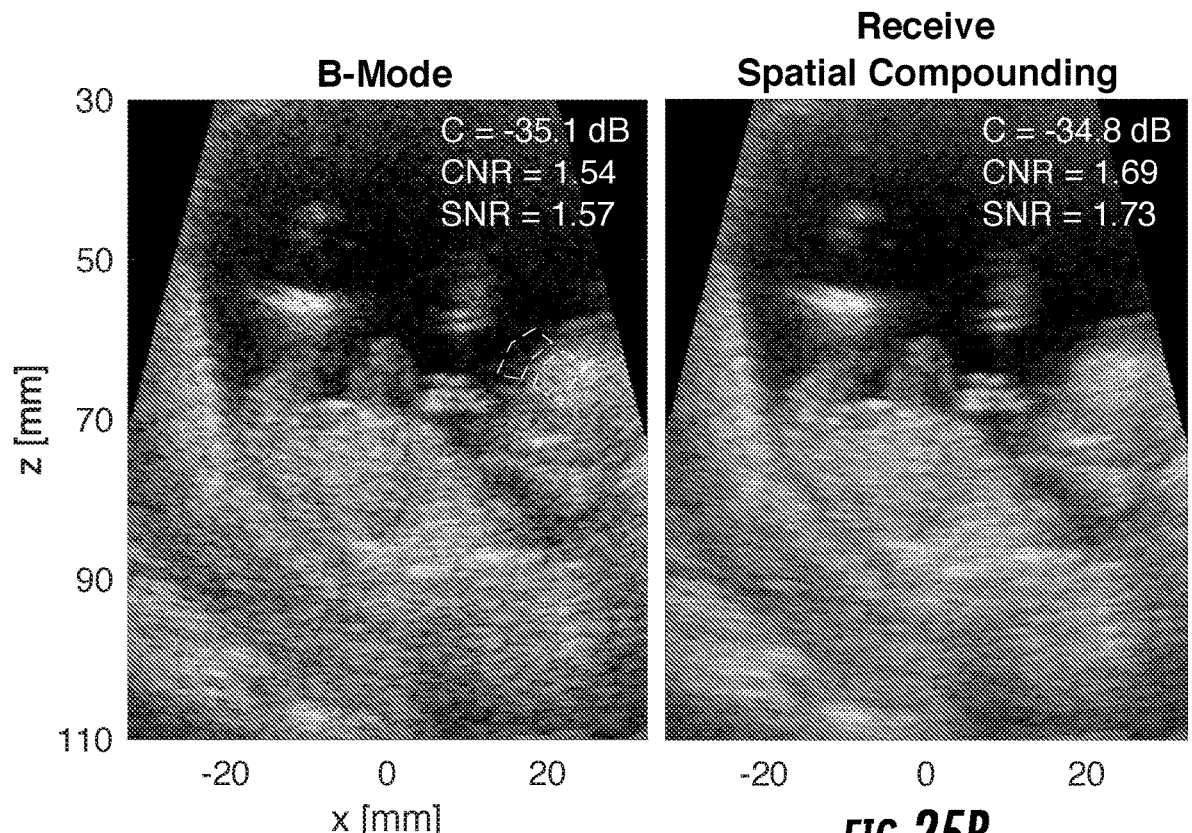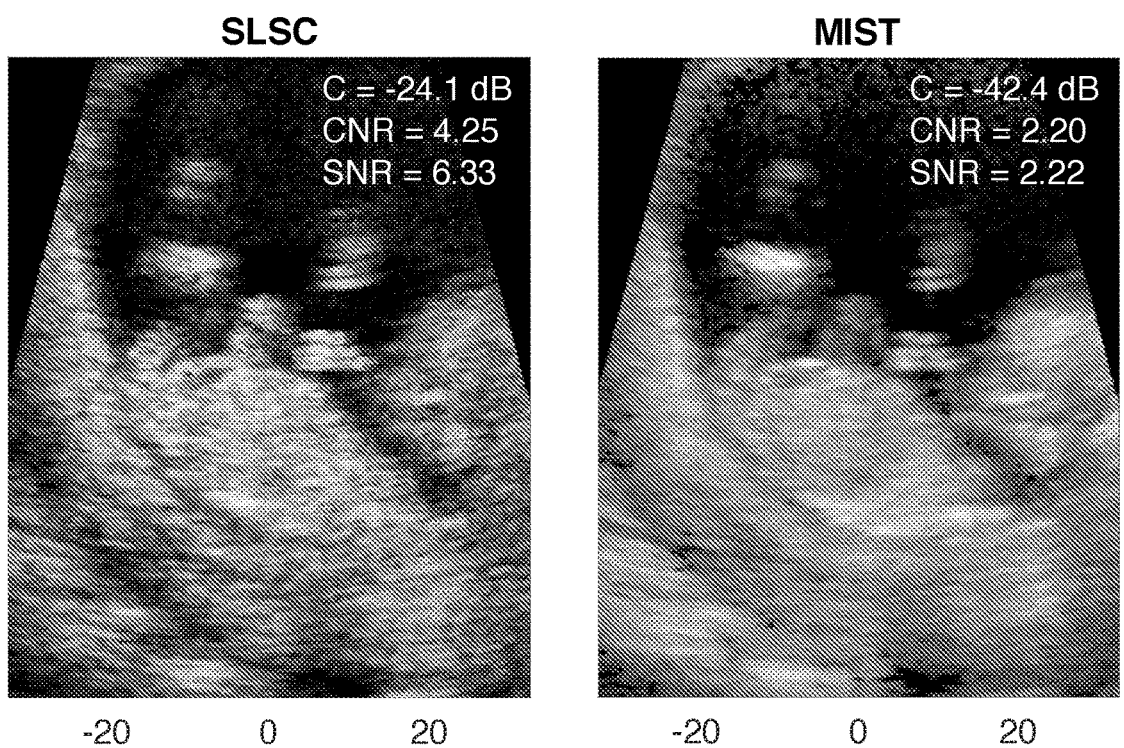
FIG. 25A  FIG. 25B  FIG. 25C  FIG. 25D

METHODS, SYSTEMS AND COMPUTER PROGRAM PRODUCTS FOR ULTRASOUND IMAGING USING COHERENCE CONTRIBUTION

FIELD OF THE INVENTION

The present invention relates to ultrasound imaging and analysis, and in particular, to methods, systems and computer program products for ultrasound imaging using coherence contribution estimates of ultrasound data.

BACKGROUND

Ultrasound imaging has many medical applications, including diagnostic imaging and non-diagnostic imaging, for example, to guide and inform other medical procedures. Conventional B-mode imaging is a two-dimensional ultrasound imaging composed of dots of variable brightness representing the amplitude of ultrasound echoes.

Ultrasound imaging systems have utilized an amount of coherence to adapt the echo signals received by the ultrasound transducer elements. For example, U.S. Pat. No. 7,744,532 discusses that beamforming, image forming or image processing parameters are varied as a function of a coherence factor to improve detail resolution, contrast resolution, dynamic range or signal-to-noise ratio (SNR). For example, a beamforming parameter such as the transmit or receive aperture size, apodization type or delay is selected to provide maximum coherence.

SUMMARY OF EMBODIMENTS OF THE INVENTION

In some embodiments, an ultrasound system for imaging a target is provided. The system includes a plurality of transducer elements; at least one transmitter configured to excite at least one of the transducer elements to emit ultrasound energy to the target; a plurality of samplers configured to sample echo signals received by at least some of the plurality of transducer elements, the echo signals comprising acoustic echoes received from the target responsive to the ultrasound energy; a coherence calculator configured to calculate a plurality of coherence values, each of the coherence values corresponding to a measure of similarity between at least two sample echo signals; an estimator configured to estimate a coherence contribution estimate, the coherence contribution estimate comprising an estimate of a contribution of at least one coherence model to the plurality of coherence values; and an image generator configured to map a plurality of coherence contribution estimates from the estimator to respective image locations corresponding to locations in the target and to generate an image of the target based on the coherence contribution estimates.

BRIEF DESCRIPTION OF THE DRAWINGS

The accompanying drawings, which are incorporated in and constitute a part of the specification, illustrate embodiments of the invention and, together with the description, serve to explain principles of the invention.

FIGS. 19A-19H are images and graphs generated by a MIST estimator of simulated targets according to some embodiments. FIGS. 19A-19C illustrate a conventional B-mode image (FIG. 19A) as compared to the mainlobe estimate (FIG. 19B) and sidelobe estimate (FIG. 19C) for a point, and FIGS. 19E-19G illustrate a conventional B-mode image (FIG. 19E) as compared to the mainlobe estimate (FIG. 19F) and sidelobe estimate (FIG. 19G) for of anechoic cyst target. FIGS. 19D and 19H are graphs of 1-D lateral profiles at 50 mm depth for a point (FIG. 19D) and an anechoic cyst target (FIG. 19H), where the y-axis has been split to display the full range of the lateral profiles.

FIGS. 22A-22B are sample images of the edge phantom with a speckle generating and an anechoic region (−∞dB contrast).

FIG. 22C is a graph of averaged lateral profiles of B-Mode and MIST images for each set of phantom simulations.

FIGS. 23A-23C and FIGS. 23F-23H are images of approximately matched B-Mode images (FIGS. 23A and 23F) and MIST images using a single sample estimate (0λ) (FIGS. 23B and 23G) and axial averaging of the covariance matrix over a wavelength (1λ) (FIGS. 23C and 23H). FIGS. 23A-23C are simulation images and FIGS. 23F-23H are phantom images. FIG. 23E is the CNR graph for the simulation.

FIG. 24A-23D are in vivo liver images comparing B-Mode (FIG. 24A), receive spatial compounding (3 apertures, 50% overlap) (FIG. 24B), SLSC (Q=5%, 1λ axial kernel) (FIG. 24C), and MIST (1λ axial kernel) (FIG. 24D).

FIGS. 25A-25D are in vivo fetal images comparing B-mode (FIG. 25A), receive spatial compounding (3 apertures, 50% overlap) (FIG. 25B), SLSC (Q=5%, 1λ axial kernel) (FIG. 25C), and MIST (1λ axial kernel) (FIG. 25D).

DETAILED DESCRIPTION OF EMBODIMENTS OF THE INVENTION

Figure 1:
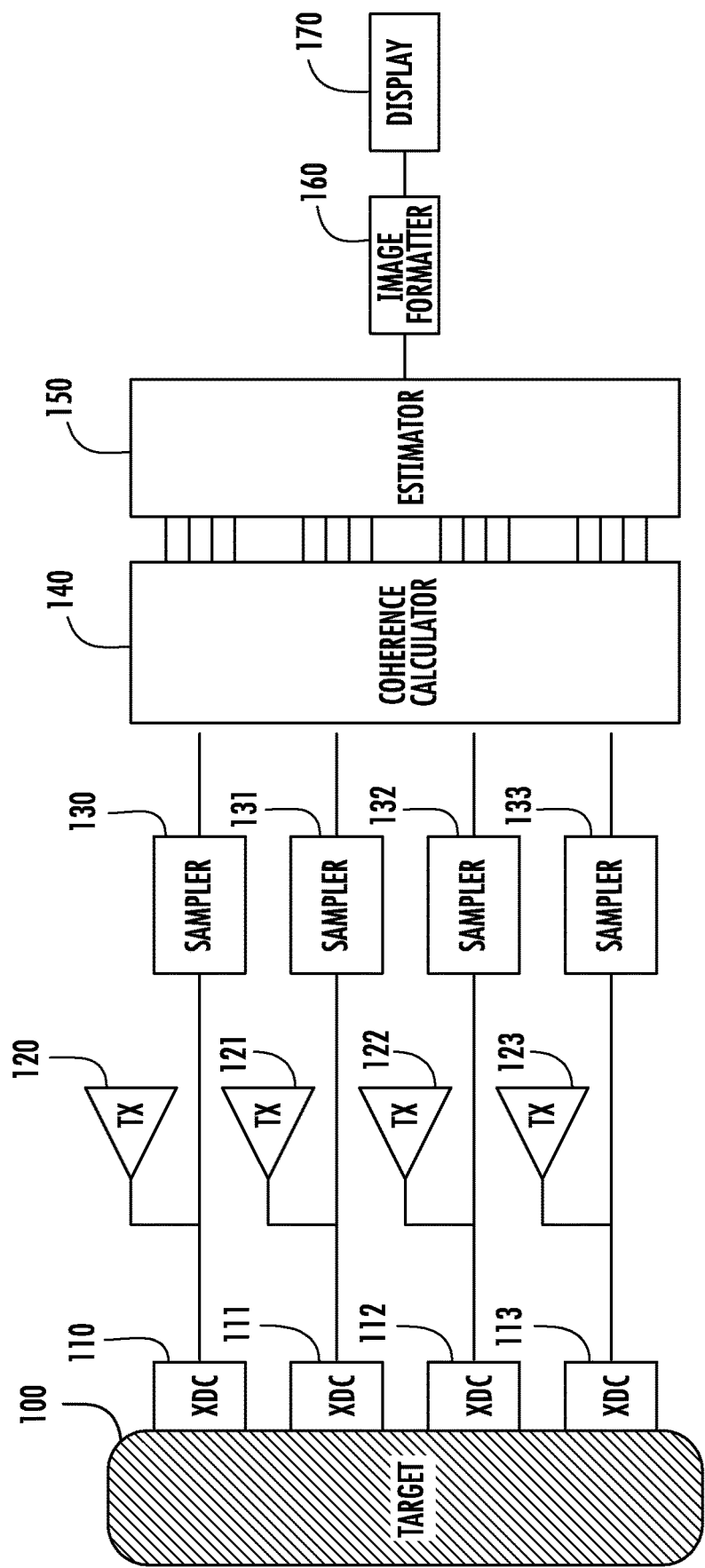
FIGS. 1-7 are block diagrams illustrating systems, methods and computer program products according to some embodiments.

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. For example, the term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

The present invention is described below with reference to block diagrams and/or flowchart illustrations of methods, apparatus (systems) and/or computer program products according to embodiments of the invention. It is understood that each block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, the present invention may be embodied in hardware and/or in software (including firmware, resident software, micro-code, etc.). Furthermore, embodiments of the present invention may take the form of a computer program product on a computer-usable or computer-readable non-transient storage medium having computer-usable or computer-readable program code embodied in the medium for use by or in connection with an instruction execution system.

The computer-usable or computer-readable medium may be, for example but not limited to, an electronic, optical, electromagnetic, infrared, or semiconductor system, apparatus, or device. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM).

Embodiments according to the present invention are described herein with reference to the term "tissue." It will be understood that the term tissue can include biological materials, such as, blood, organs, vessels, and other biological objects found in a body. It will be further understood that embodiments according to the present invention may be applicable to humans as well as other species. Embodiments according to the present invention may also be utilized to image objects other than tissue.

It will be understood that the scope of the present invention includes, for example, one dimensional (1D) ultrasound imaging (e.g., M-Mode imaging with repeated firings along a single line, which are displayed as an image on a screen), two dimensional (2D) ultrasound imaging and 3D (or volumetric) ultrasound imaging. In addition, the components of the ultrasound imaging described herein may be packaged as a single unit or packaged separately and interconnected to provide the functions described herein.

FIG. 1 is a block diagram of a system according to some embodiments. As illustrated in FIG. 1, the system includes a plurality of transducer elements 110-113 (labeled as "XDC") for interrogating a target 100. The transducer elements 110-113 are connected to a plurality of transmitters 120-123 (labeled as TX). In some embodiments, the transducer elements incorporate a piezoelectric material that converts electrical energy to acoustic (ultrasonic) energy and vice versa. The transmitters 120-123 excite at least one of the transducer elements 110-113 so that the excited transducer elements 110-113 emit ultrasound energy into the target 100. The ultrasound energy reflects from structures within the target 100 and the returned echoes are converted from ultrasound energy to electrical signals by the transducer elements 110-113. These echo signals are sampled by the samplers 130-133. The sampled signals are employed by the coherence calculator 140 to calculate a plurality of coherence values, each of which corresponds to a measure of similarity between at least two sampled echo signals. The coherence values computed by the coherence calculator 140 are used by the estimator 150 in order to estimate a coherence contribution estimate comprising an estimate of a contribution of at least one coherence model to the plurality of coherence values. The coherence contribution estimate is used by the image generator 160 to map coherence contribution estimates to image locations corresponding to locations in the target. Finally, the map of coherence contribution estimates produced by the image generator is presented in the display 170.

In some embodiments, the estimator 150 is configured to generate estimated contributions of at least one coherence model to the plurality of coherence values using a least squares estimation or maximum likelihood estimation. Additional estimation methods may be used, including but not limited to minimum mean square error (MMSE), maximum posteriori (MAP), minimum variance unbiased (MVUB/MVUE) and Bayes estimators.

The image generator 160 may be configured to generate the image of the target based on the estimated contributions in an absence of processing beamsummed data.

The coherence contribution estimate may be calculated according to various techniques. The coherence contribution estimate may be the covariance of the received signals and/or the normalized correlation of the received signals. The coherence contribution estimate between any two received signals may be the phase difference between those received signals.

Various ultrasound imaging techniques may be used. For example, the transmitters may be configured to form a shaped beam within the target. The transducer elements may form various configurations, such as one of a linear array, a curved array, a curvilinear array, a 1.25D array, a 1.5D array, a 1.75D array, a 2D array, or an annular array. In some embodiments, not all of the transducer elements may be sampled, i.e., the transducer elements may form a sparsely sampled array. In some embodiments, the transducer elements incorporate elements of varying sizes.

In some embodiments, the coherence calculator computes the coherences between all possible pairs of sampled signals or between a subset of possible pairs of sampled signals. In some embodiments, the signals received from a plurality of portions of the transducer array are delayed and summed to yield sub-aperture signals corresponding to the portions of the array, and the coherence calculator computes the coherences of the sub-aperture signals.

The estimator may estimate coherence using various techniques. For example, the estimator may process the coherence averaged from multiple spatial locations. The estimator may process the coherence averaged from multiple signal bandwidths. The coherence contribution estimate from the region of interest in the target may be estimated from multiple coherences from multiple acquisitions from the same spatial location within the target, but utilizing different transmitter configurations.

Various transmitter configurations may be used. In some embodiments, the transmitter configurations correspond to transmission from different portions of the transducer array. The transmitter configurations may utilize different phasing and/or weighting of the transducer array elements.

It should be understood that any suitable number of transducers, transmitters, and/or samplers may be used. It should be understood that the various elements of the ultrasound system may be provided on one device or processor or circuit, or that the elements of the system may be separated into different processors or circuits, and moreover, the functions of the various elements shown do not necessarily reside in the same processor or circuit. FIGS. 2-9 illustrate various non-limiting examples of configurations of systems according to embodiments of the invention; however, one of skill in the art would understand that additional configurations are within the scope of the invention.

Figure 2:
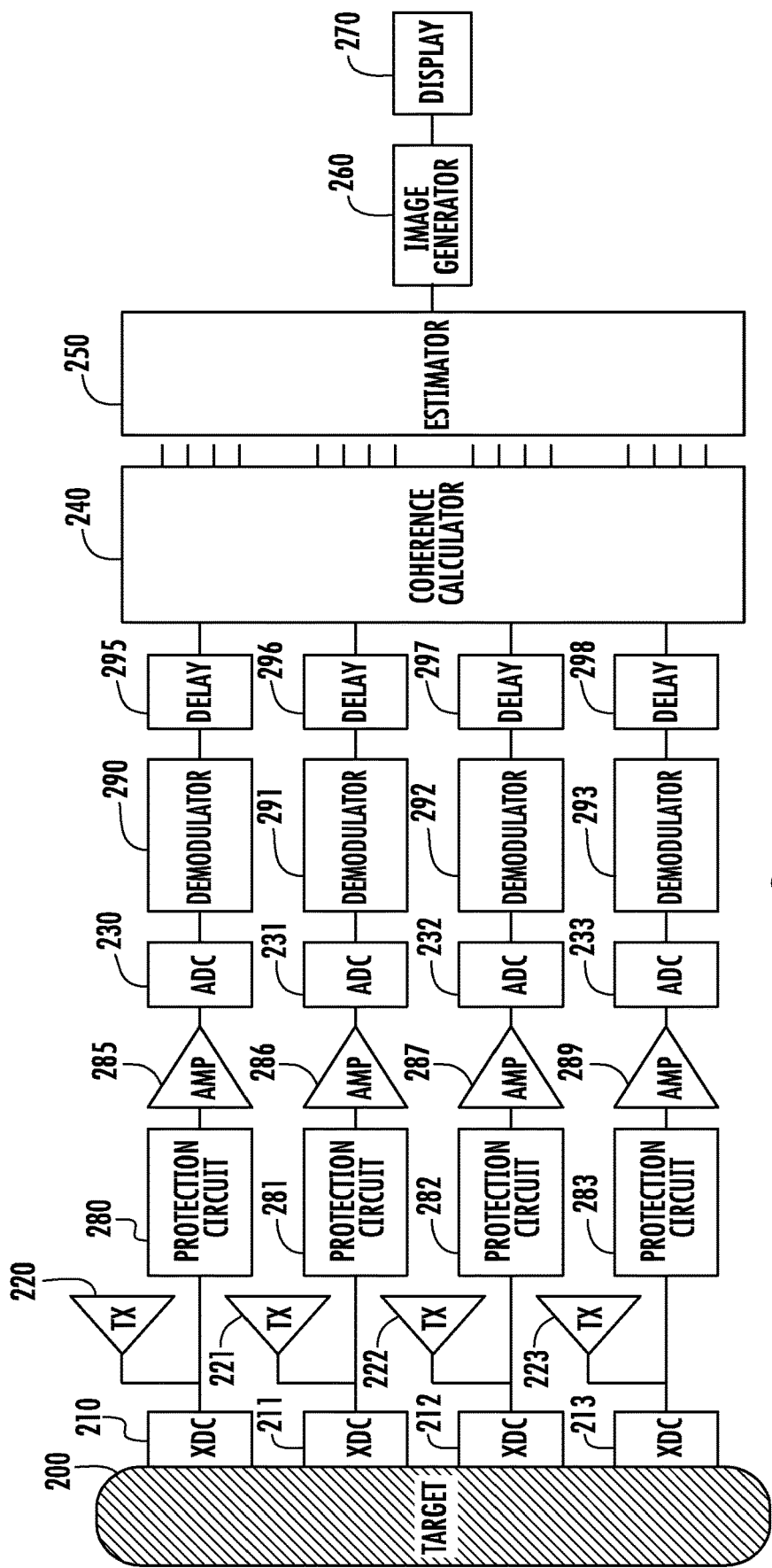

FIG. 2 is a block diagram of another example embodiment of the present disclosure. In the interest of brevity, like numbers in FIG. 2 refer to like elements in FIG. 1. This example shows four transducer elements 210-213, but those knowledgeable in the field of ultrasound imaging will realize that larger numbers of transducer elements can be readily employed in some embodiments. Commercial ultrasound scanners often use binary multiples of transducer elements. Common transducer element counts are 64, 128, and 192 elements. In some embodiments, the system incorporates receive protection circuitry to enable at least one transmit circuit to address at least one array element that is also addressed by at least one sample. FIG. 2 illustrates each transducer element 210-213 being wired to single corresponding transmitters 220-223 and single corresponding receive circuits [incorporating protection circuit 280-283, amplifiers 285-289 (labeled "AMP"), and analog to digital converters 230-233 (labeled "ADC")]. Those knowledgeable in the field of ultrasound imaging will appreciate that imaging systems are often designed to employ multiplexers between the transducer elements and/or transmitter and receive circuits so that different transducer elements may be mapped to the same transmitters and receive circuits under different conditions. One common application of this approach is in the use of so-called linear arrays in which an acoustically active aperture is electronically swept along a larger transducer array. A number of companies have developed compact transmitters specifically for ultrasound imaging applications. Notable examples include the HV7351 and HV7350 manufactured by Microchip. Protection circuits can consist of high voltage analog switches such as the Microchip HV2808, or transmit/receive switches such as the Microchip MD0105. A variety of integrated circuits have been designed to function effectively as amplifiers in ultrasound receive channels. Commonly used components include the AD8334 manufactured by Analog Devices and the MAX 2037 manufactured by Maxim Integrated. Analog to digital converters suitable for ultrasound imaging systems include the Analog Devices AD9637. Texas Instruments produces a single chip, the AFE5818 that integrates an amplifier and analog to digital controller. The example of FIG. 2 also includes a set of demodulators 290-293 which act to convert the real Radio Frequency (RF) echo signals into complex signals. Complex signals can be advantageous for certain types of processing, as will be shown below, and have the advantage of requiring a lower sampling rate to avoid artifacts. While FIG. 2 shows the demodulator after the ADC, implying that the demodulation is performed on the sampled data, those knowledgeable of ultrasound will recognize that demodulation can also be performed in the analog domain, prior to digitization. Delays 295-298 act to delay the received echo signals to focus at a specific range of interest. In typical ultrasound imaging systems these delays are continuously updated so that the focus tracks the transmitted pulse as it travels into the target.

Figure 3:
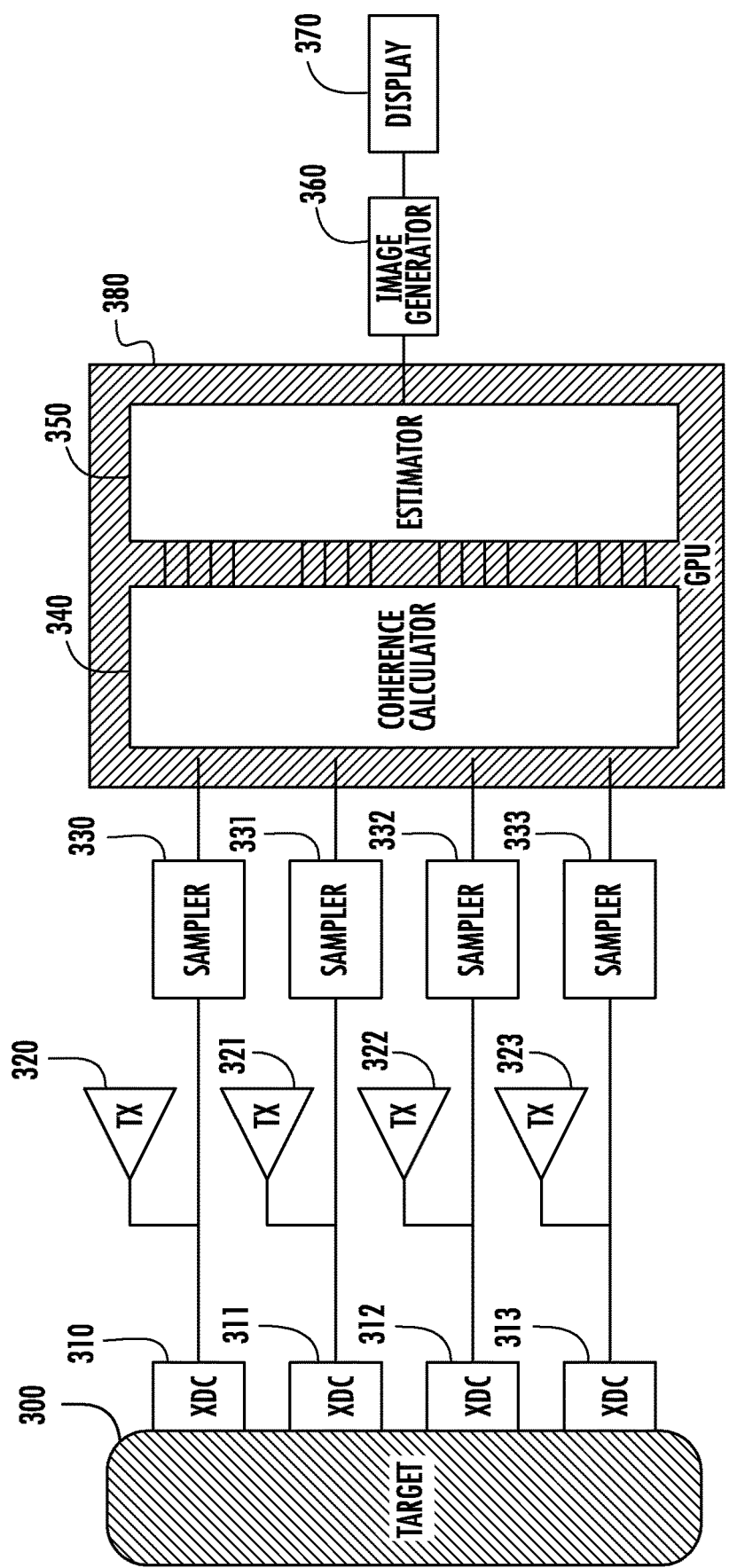
Figure 4:
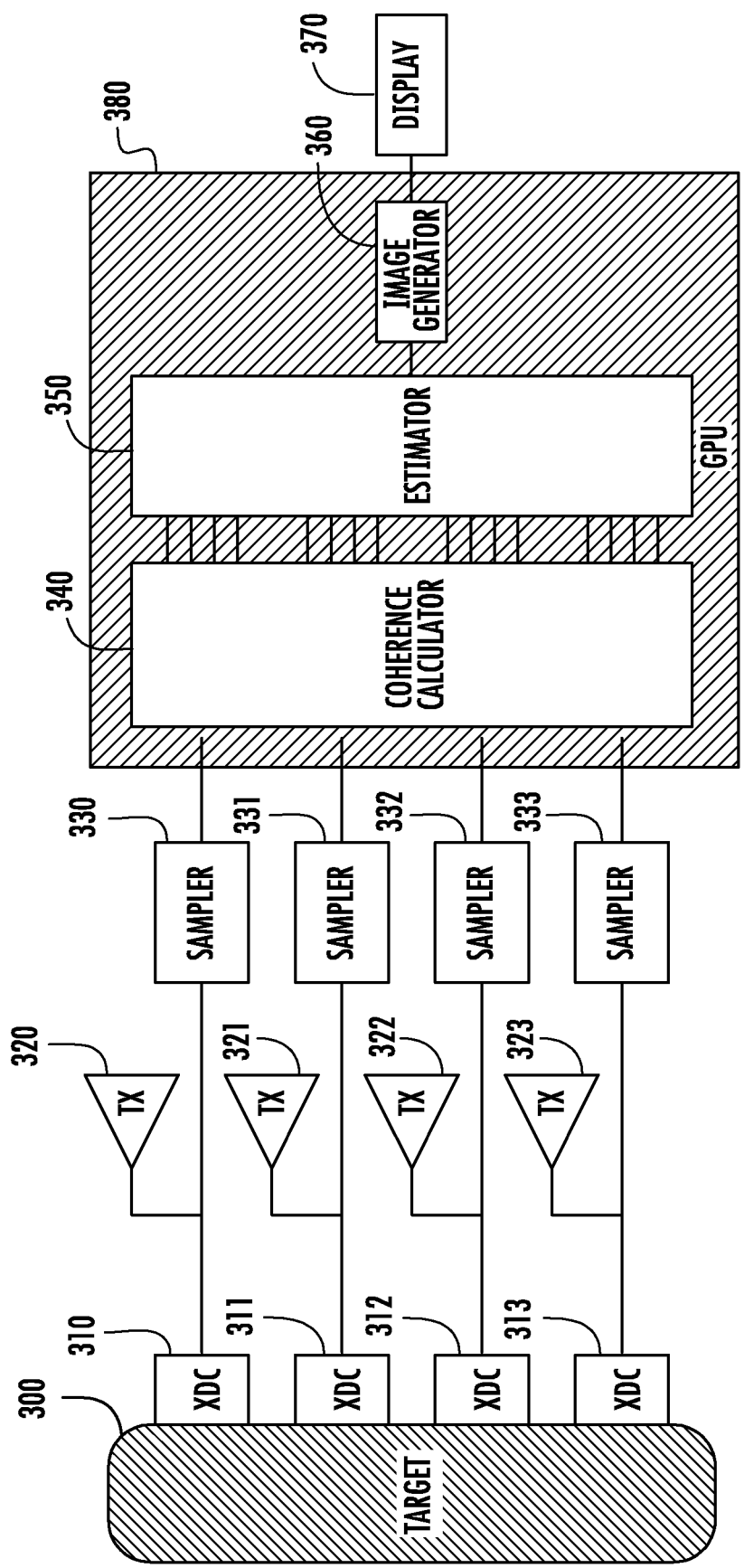

In the interest of brevity, like numbers in FIGS. 3-9 also refer to like elements in FIG. 1. FIG. 3 illustrates that the coherence calculator 340 and the estimator 350 are provided on a graphics processing unit (GPU) 380. FIG. 4 illustrates that the coherence calculator 440, estimator 450 and image generator 460 may be provided on the GPU 480.

Figure 5:
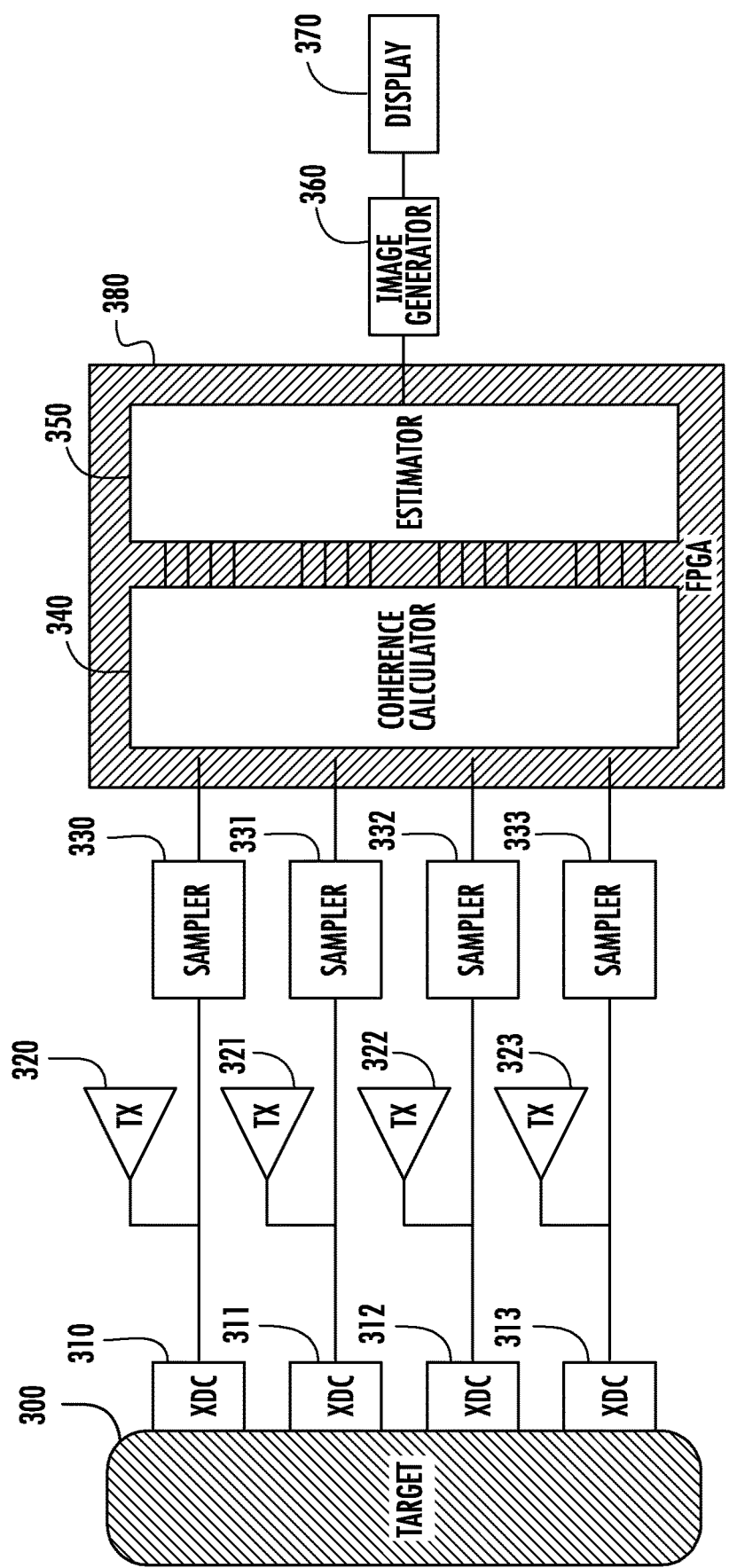

It should be understood that any suitable processor or circuit may be used to perform the operations described herein. For example, as shown in FIG. 5, a field programmable gate array (FPGA) 580 may be used to provide the coherence calculator 540 and the estimator 550.

Figure 6:
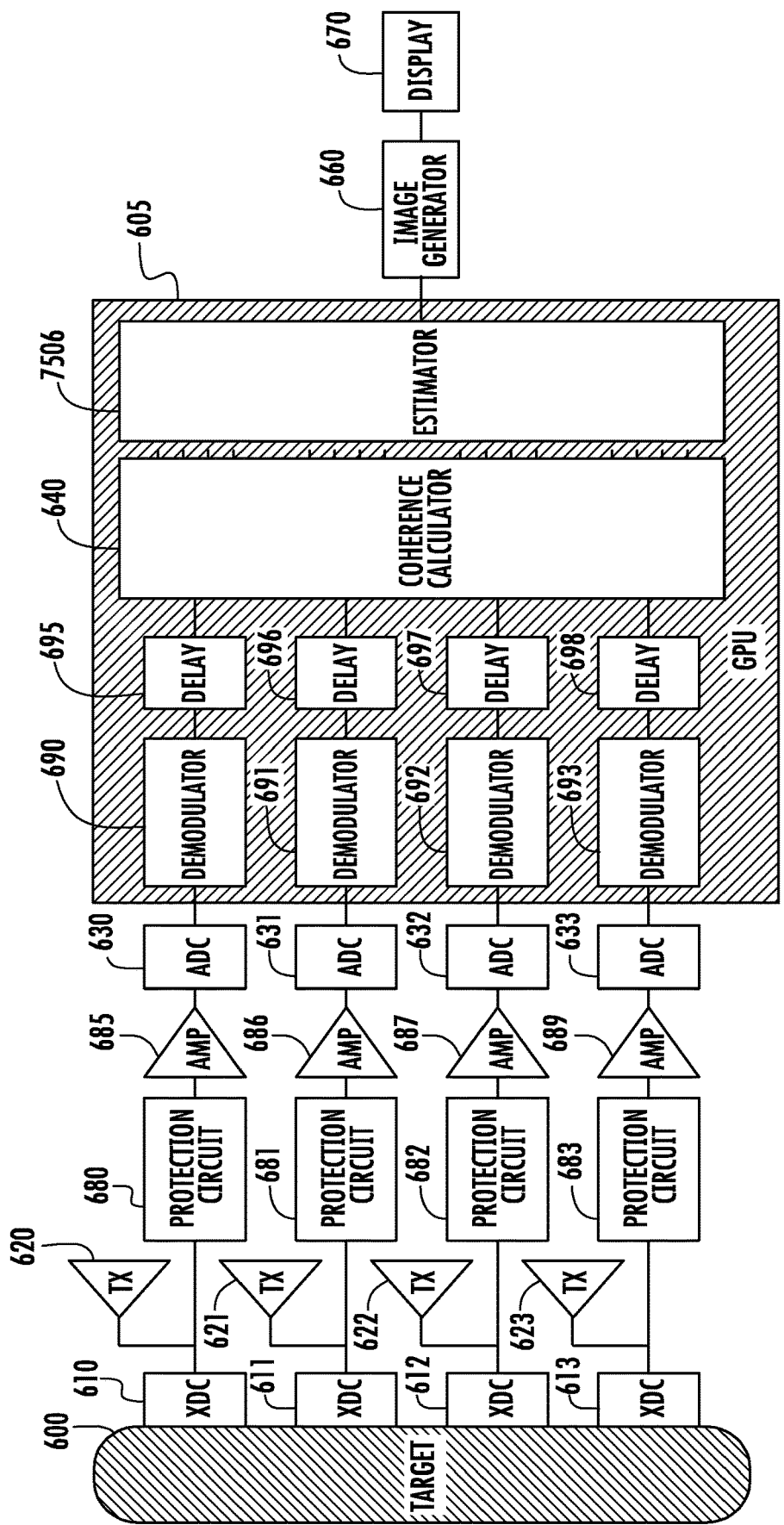

As shown in FIG. 6, a GPU 605 may be used to provide the demodulators 690-693, delays 695-698, coherence calculator 640, estimator 650 and image generator 660.

Figure 7:
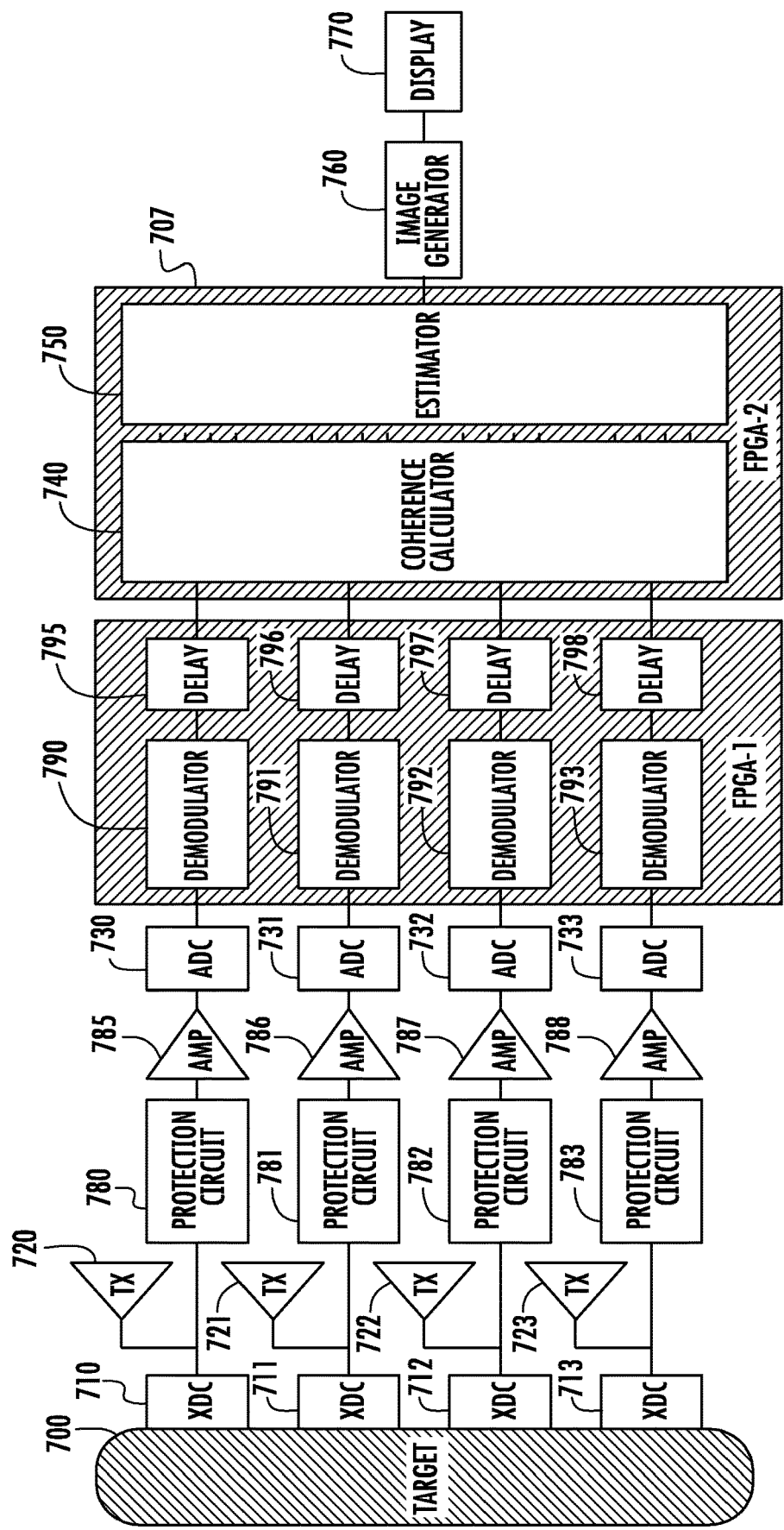

As shown in FIG. 7, an FPGA is used to provide the demodulators 790-793 and the delays 795-798, and another FPGA is used to provide the coherence calculator 740 and estimator 750.

Figure 8:
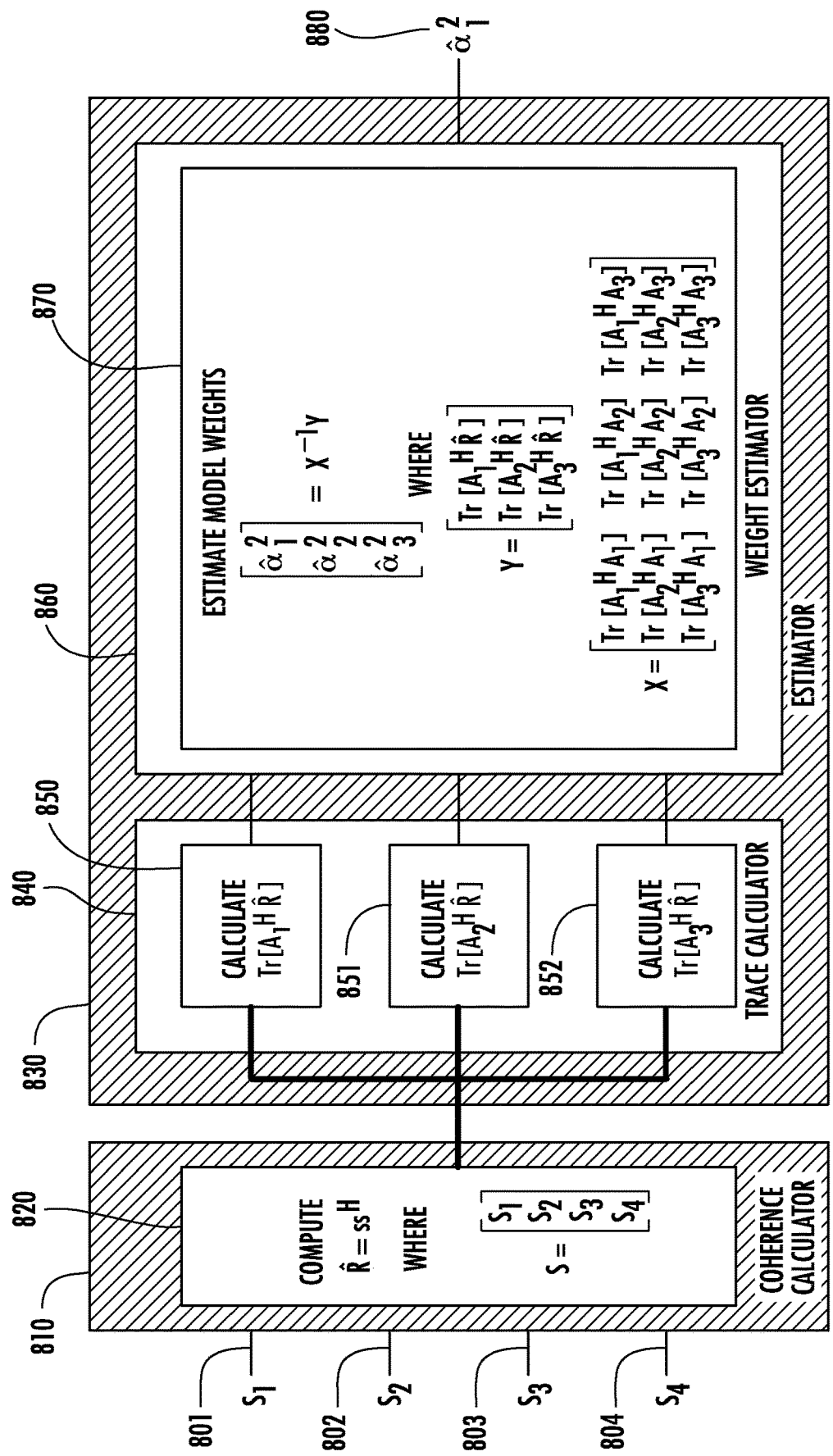
FIG. 8 is a block diagram of the coherence calculator and an estimator of FIGS. 1-7.

FIG. 8 illustrates various operations performed on the signals $s_1$-$s_4$ 801-804 in the systems of FIGS. 1-7. The operations 820 of the coherence calculator 810, the operations 850-852 of the trace calculator 840, and the operations 870 of the weight estimator 860 of the estimator 830 are described in additional detail herein.

Figure 9:
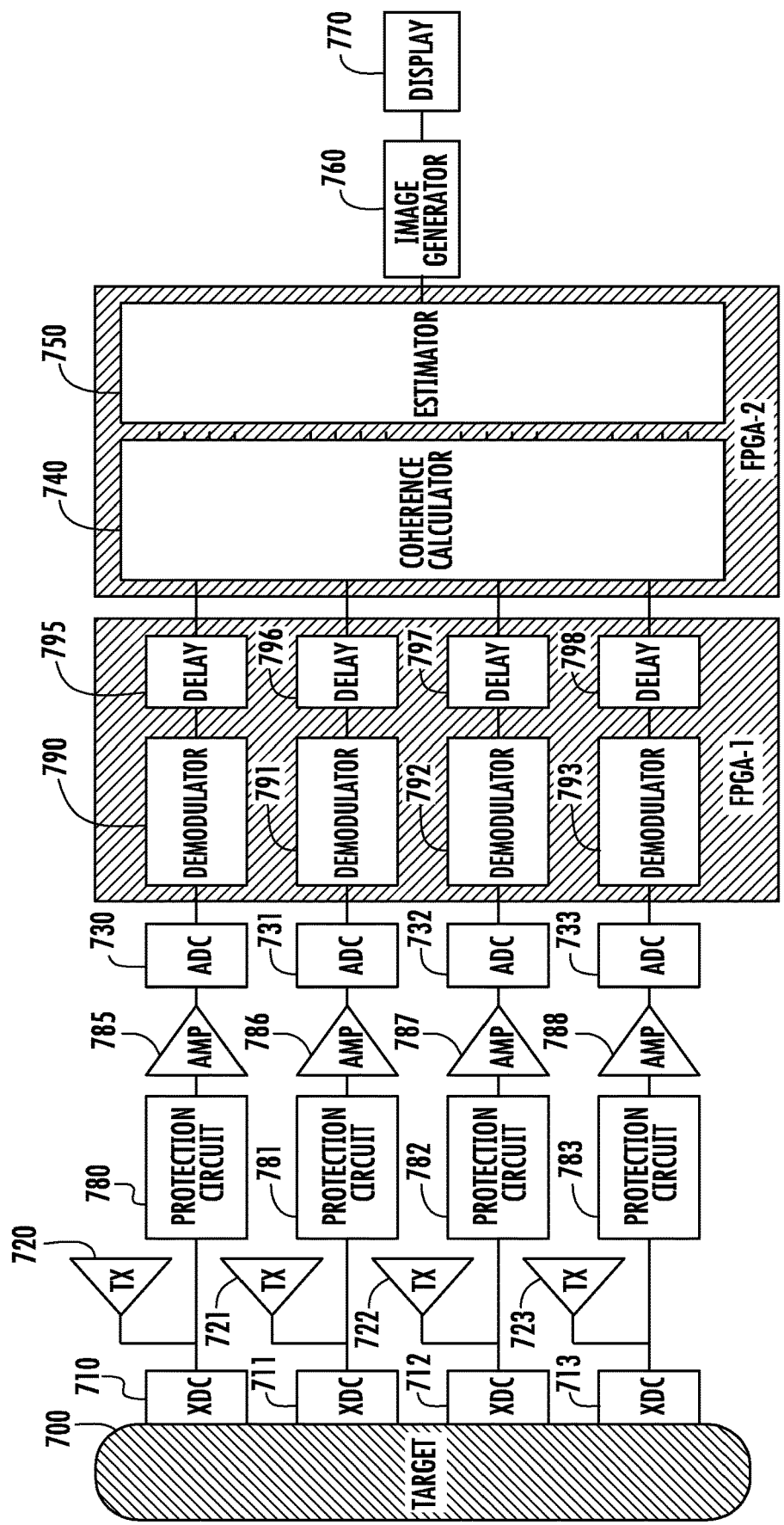
FIG. 9 is a block diagram illustrating systems, methods and computer program products according to some embodiments.

FIG. 9 illustrates a system according to some embodiments in which the demodulators 990-993 and delays 995-998 are provided on an FPGA 905, and the coherence calculator 940 is in communication with a trace calculator 952 on another FPGA 907, and a weight estimator 954 and image generator 960 are provided on a GPU 909. Various functions of the trace calculator 952 and weight estimator 954 are described in more detail herein.

Figure 10:
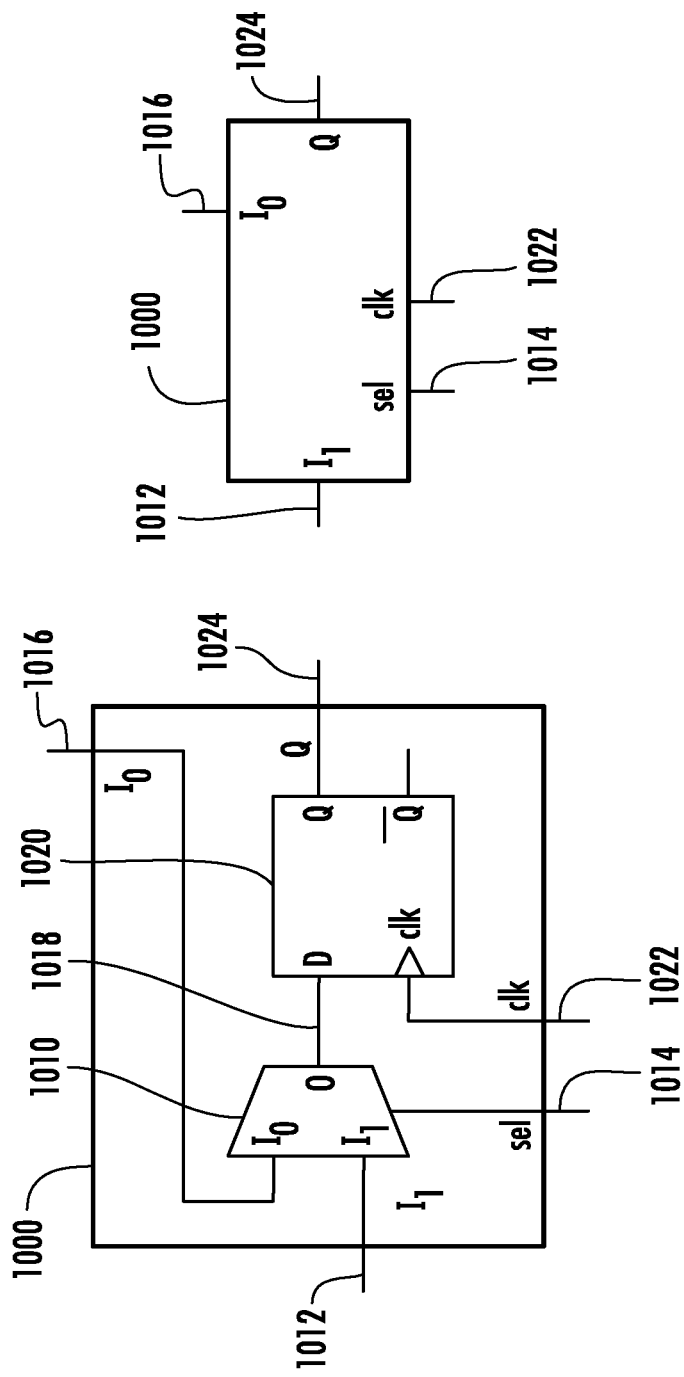
FIG. 10 illustrates a representative logic cell that is used in an embodiment of the coherence calculator and trace calculator presented in FIG. 8.

FIG. 10 presents a representative logic cell that is used in an embodiment of the coherence calculator and trace calculator presented in FIG. 8. The logic cell 1000 includes a digital multiplexer 1010 and a D Flip-Flop 1020. The multiplexer and flip-flop are well known digital components that are available in almost all commercially available Field Programmable Gate Arrays (FPGAs). Well known FPGA manufacturers include Xilinx and Intel. The multiplexer presents either signal $I_0$ 1016 or $I_1$ 1012 to the D input 1018 of the flip-flop. The multiplexer output maps to signal $I_0$ when sel 1014 is low and to signal $I_1$ when sel is high. Upon each rising edge of clk 1022 the D input 1018 of the flip-flop is presented at the Q output 1024. The left panel of FIG. 10 shows a detailed view of the logic cell, while the right panel shows a higher level view of the same component.

Figure 11:
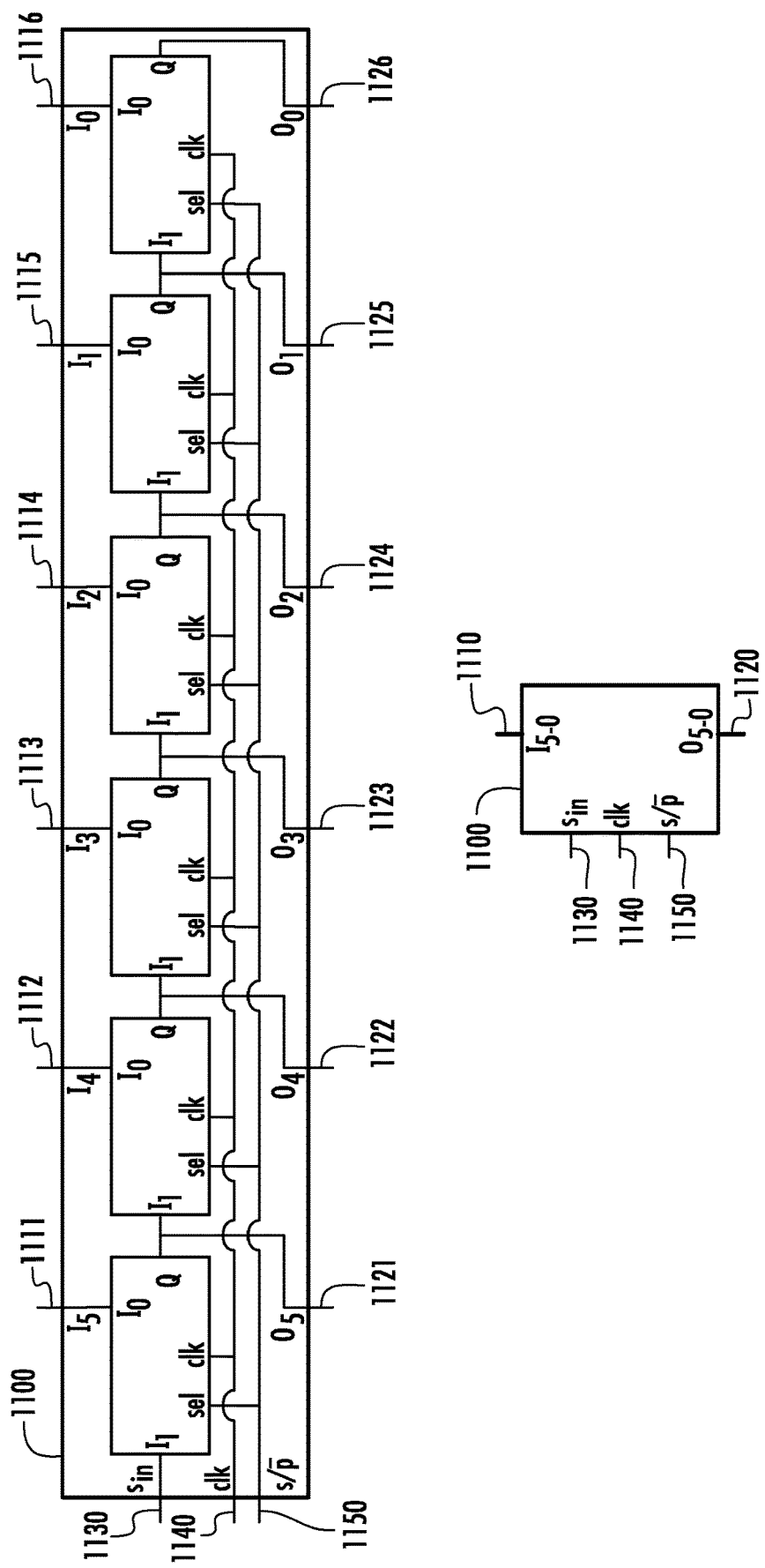
FIG. 11 illustrates a 6 bit register that is built from the logic cell presented in FIG. 10 and that is used in an embodiment of the coherence calculator and trace calculator presented in FIG. 8.

FIG. 11 presents a 6 bit register that is built from the logic cell presented in FIG. 10 and that is used in an embodiment of the coherence calculator and trace calculator presented in FIG. 8. The register 1100 can be loaded serially through $s_{in}$ 1130 or in parallel through $I_{5-0}$ 1111-1116. While this embodiment uses only 6 bits, an experienced designer will appreciate that this basic design can be extended to more bits as needed. For typical ultrasound imaging systems data is sampled at 12 or 14 bits. The register of FIG. 11 outputs bits in parallel through $O_{5-0}$ 1121-1126. The operation of the register is controlled by the signals clk 1140 and s/p 1150. If the s/p signal is high, then on the rising edge of the clk signal the $s_{in}$ value will be loaded into the first flip-flop and the output of each flip-flop will be loaded into the next, downstream flip-flop. In this manner a 6-bit word can be loaded serially into the register. If the s/p signal is low then on the rising edge of clk the input values $I_{5-0}$ will be loaded into the flip-flops in parallel. This allows a 6-bit register to be loaded in parallel. The top panel of FIG. 11 shows a detailed view of the 6-bit register, while the bottom panel shows a simplified view of the same circuit.

Figure 12:
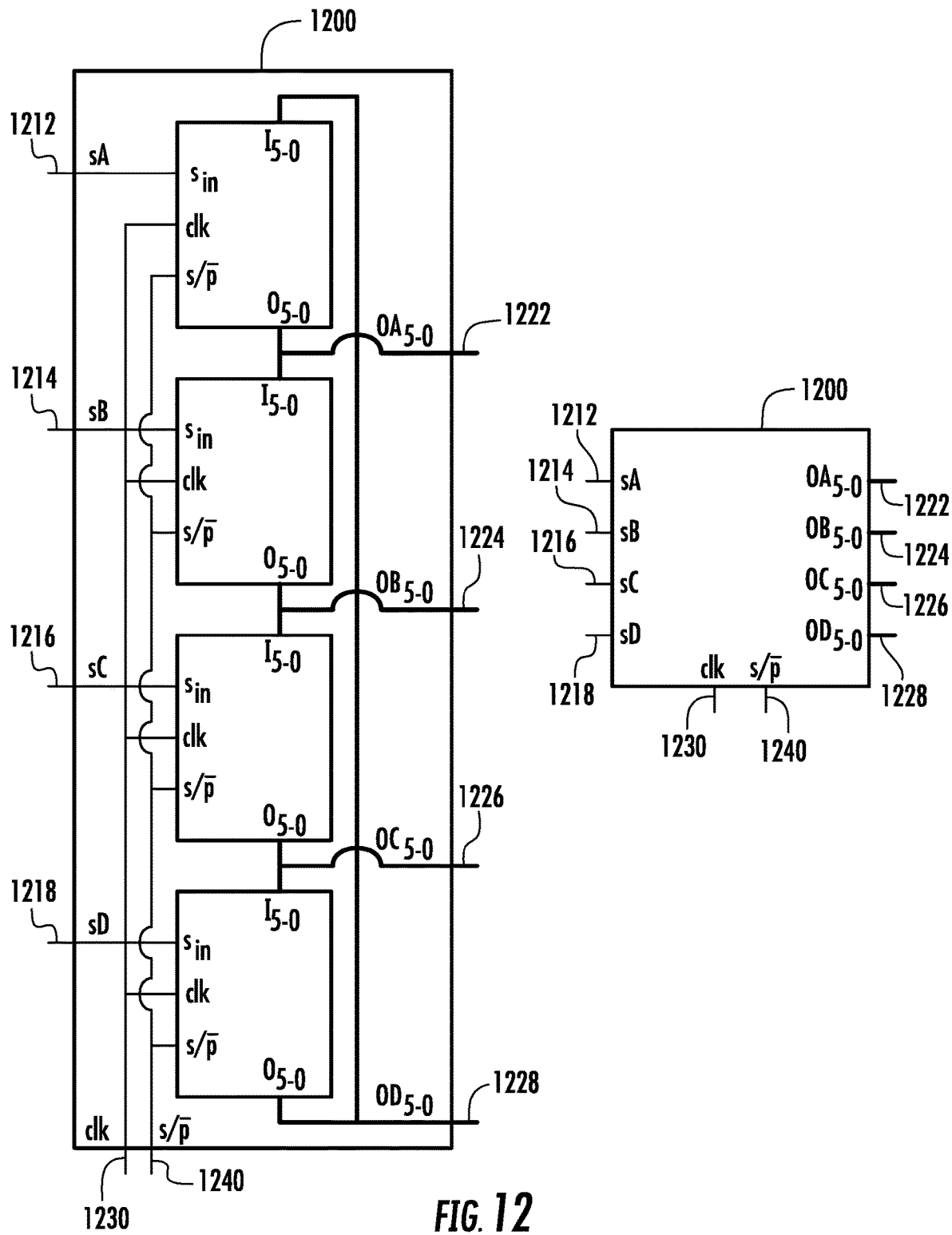
FIG. 12 illustrates a 4 word circularly wired register bank.

FIG. 12 presents a 4 word circularly wired register bank. Each register in the bank has its own serial input 1212-1218 and its own 6-bit wide parallel output 1222-1228. All registers are controlled by common clk 1230 and s/p 1240 signals. When s/p is high, a rising edge on clk will cause all of the $s_{in}$ to be loaded into their respective registers while shifting bits within the registers from left to right. Alternatively, when s/p is low, a rising edge on clk will shift the word in each register into the register below it, except that the word from the lowest register will shift into the uppermost register. It is this behavior that causes this circuit to be called a circularly wired register bank. The example of FIG. 12 shows four registers in order to map one register to each of the four receive channels in the example embodiments. For a more typical ultrasound system with 64 channels it would be preferable to use 64 registers in this design. Alternative embodiments are possible that trade multiple parallel registers for faster clock cycling. The left panel of FIG. 12 shows a detailed view of the circularly wired register bank, while the right panel shows a simplified view of the same circuit.

Figure 13:
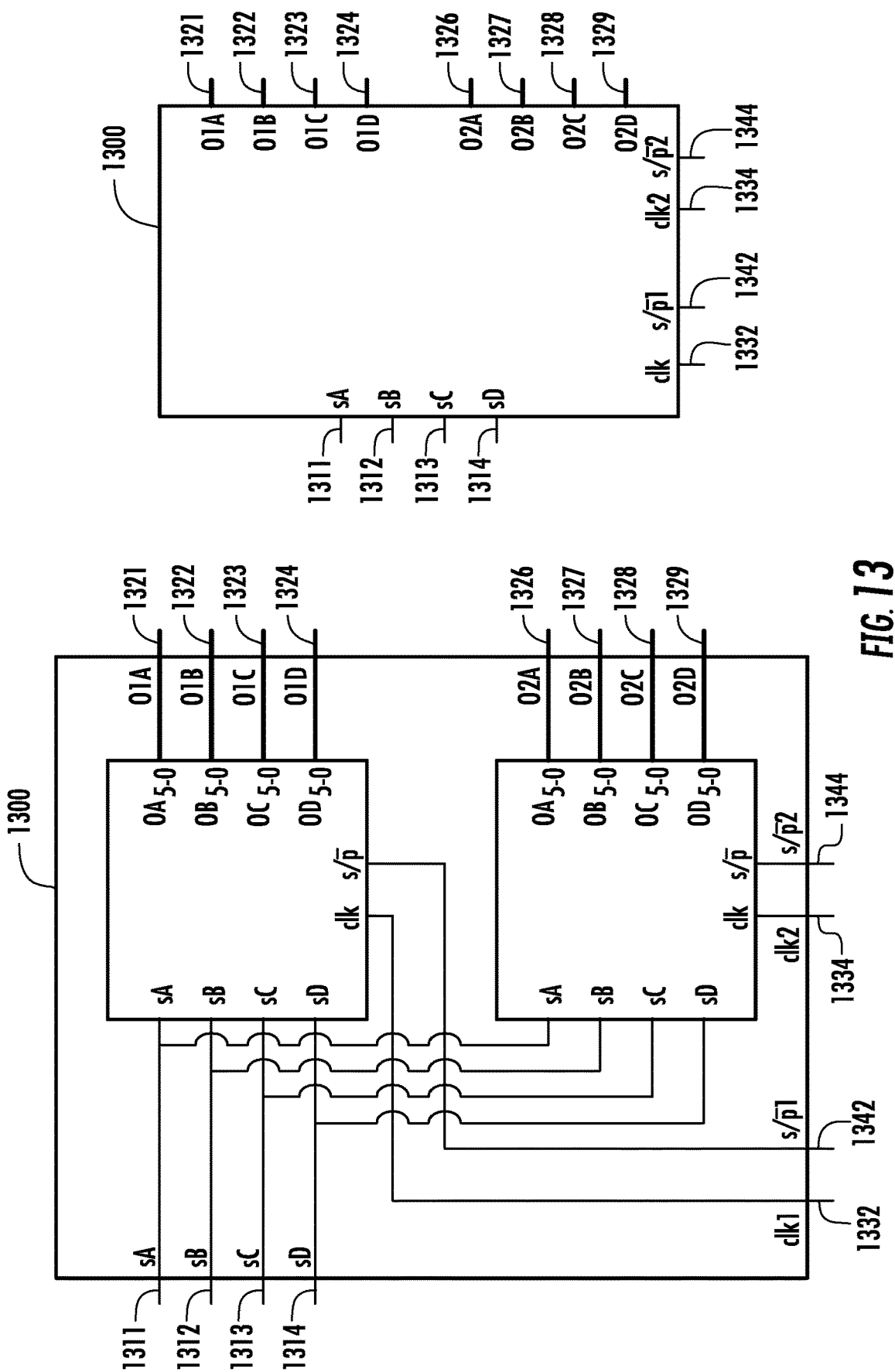
FIG. 13 illustrates a double register bank formed by combining two of the previously described circularly wired register banks.
Figure 14A:
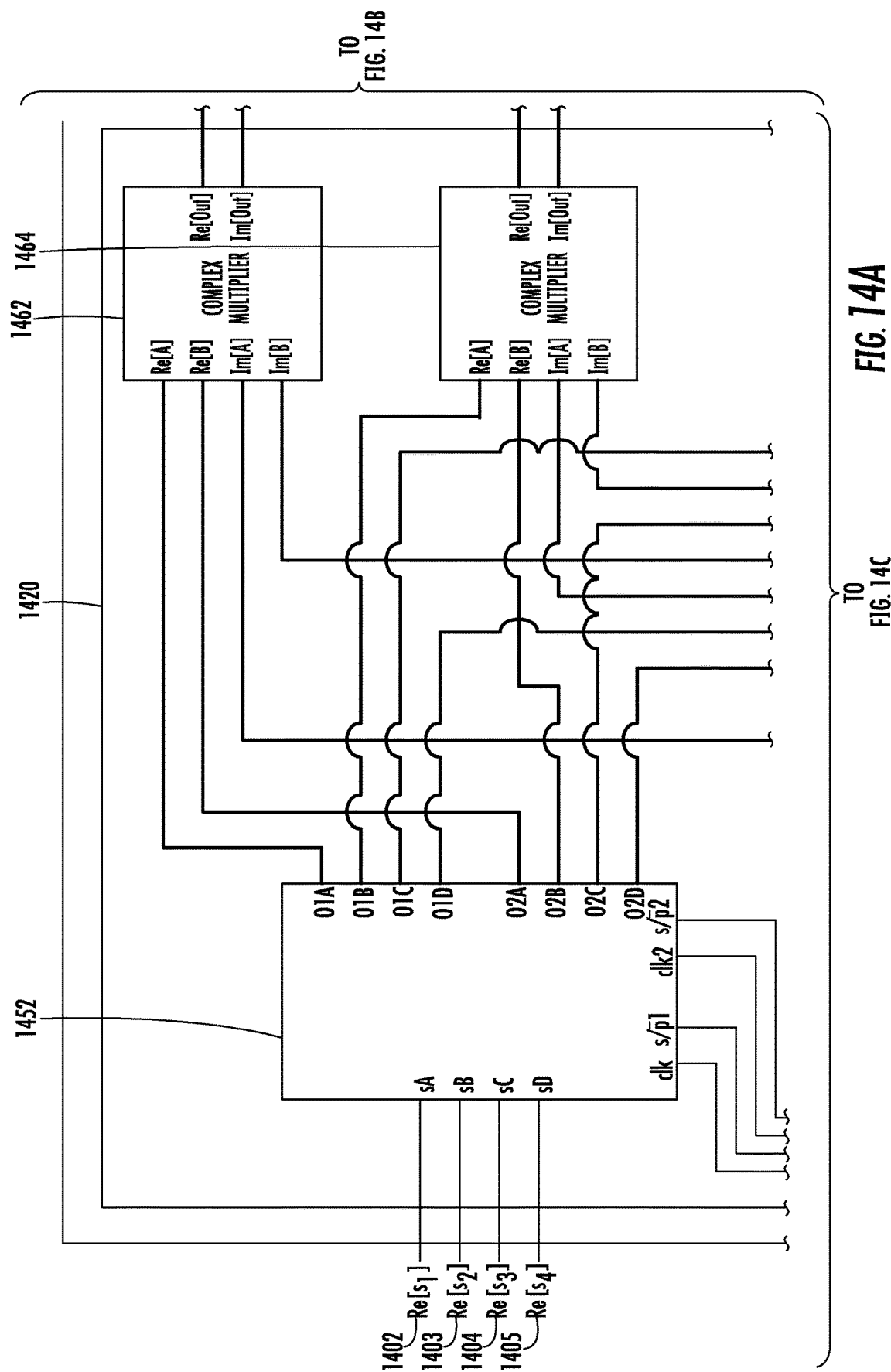
FIGS. 14A-D illustrate a circuit incorporating a coherence calculator and a single trace calculator according to some embodiments.
Figure 14B:
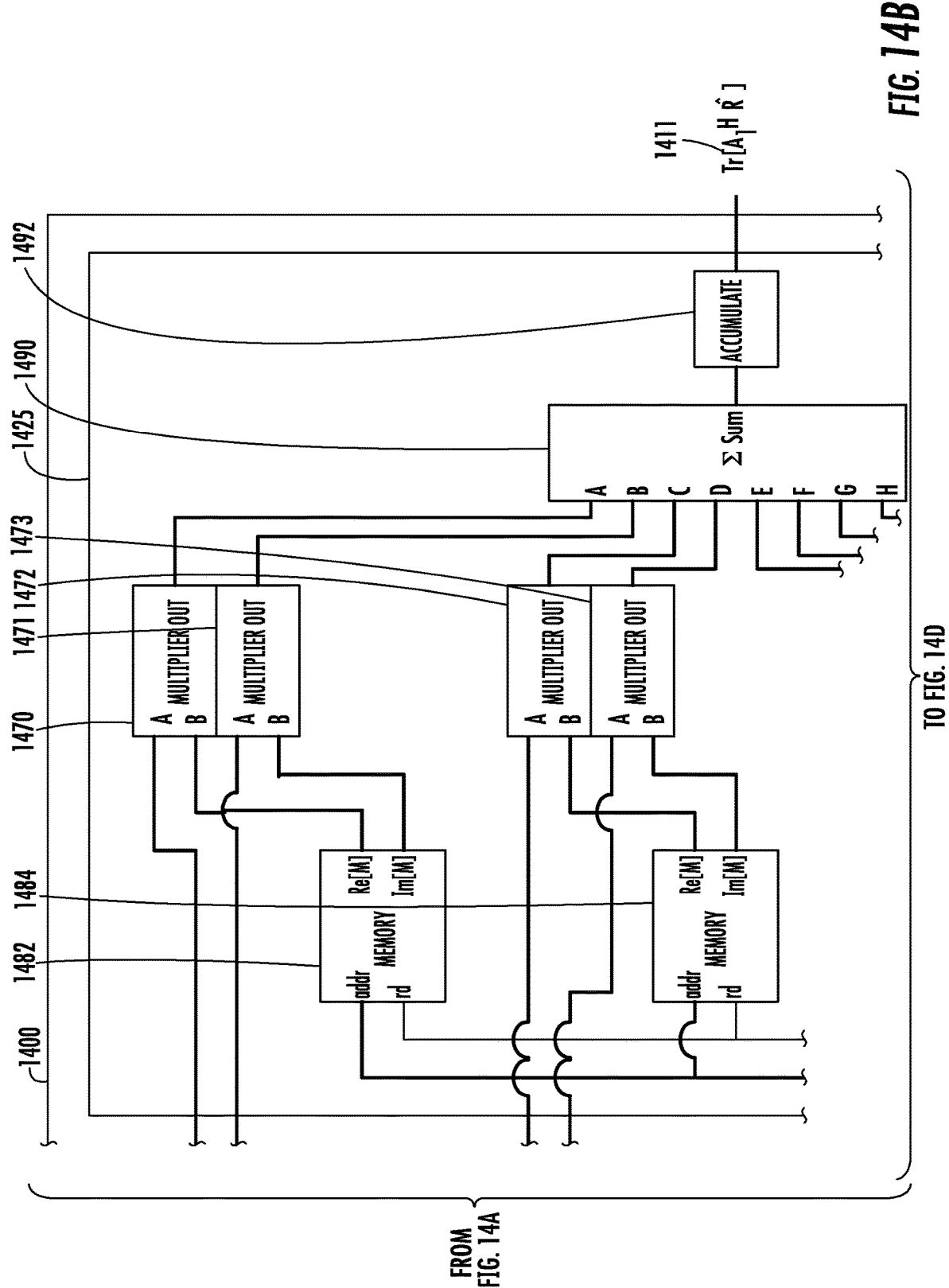
Figure 14C:
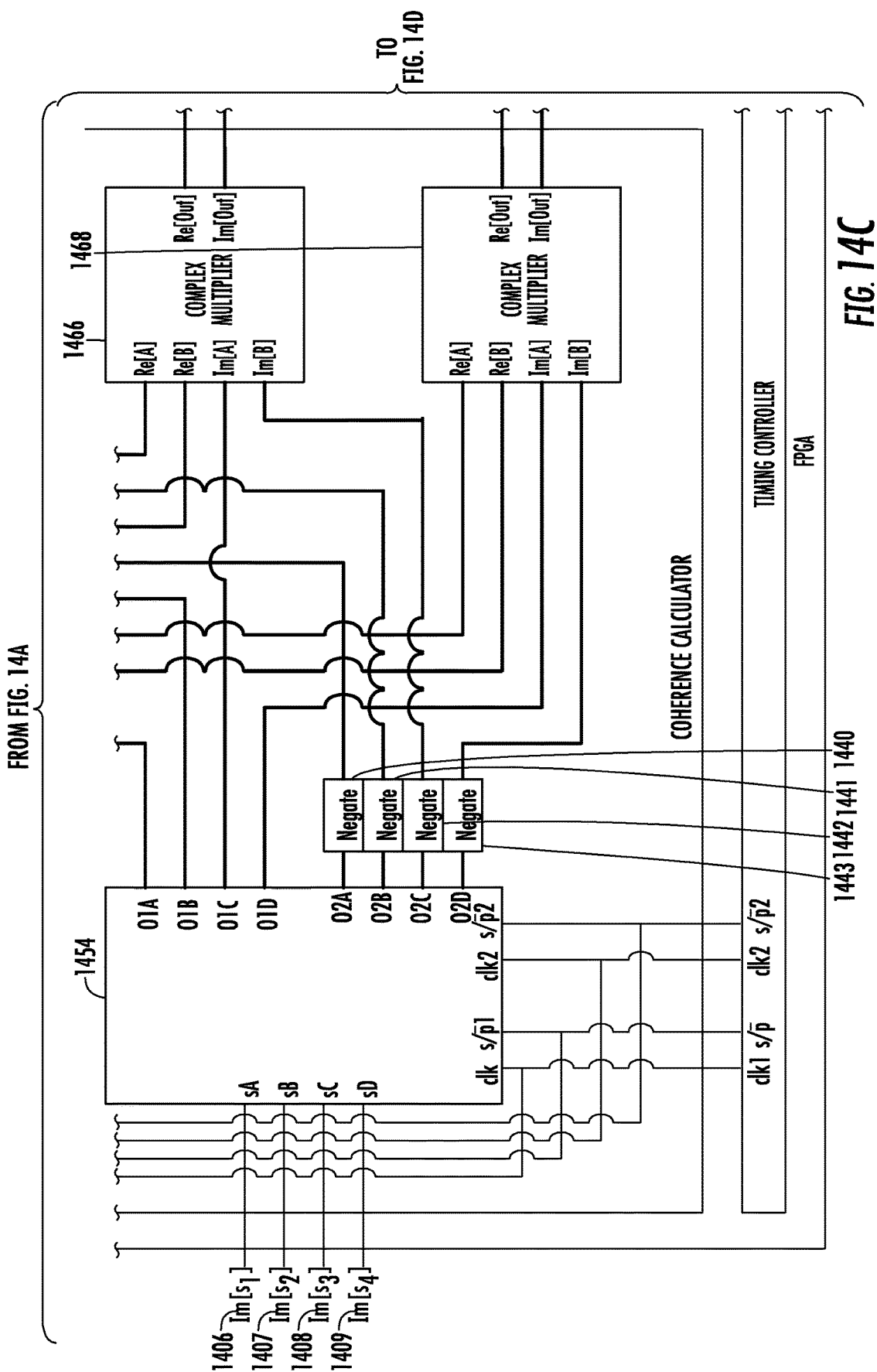
Figure 14D:
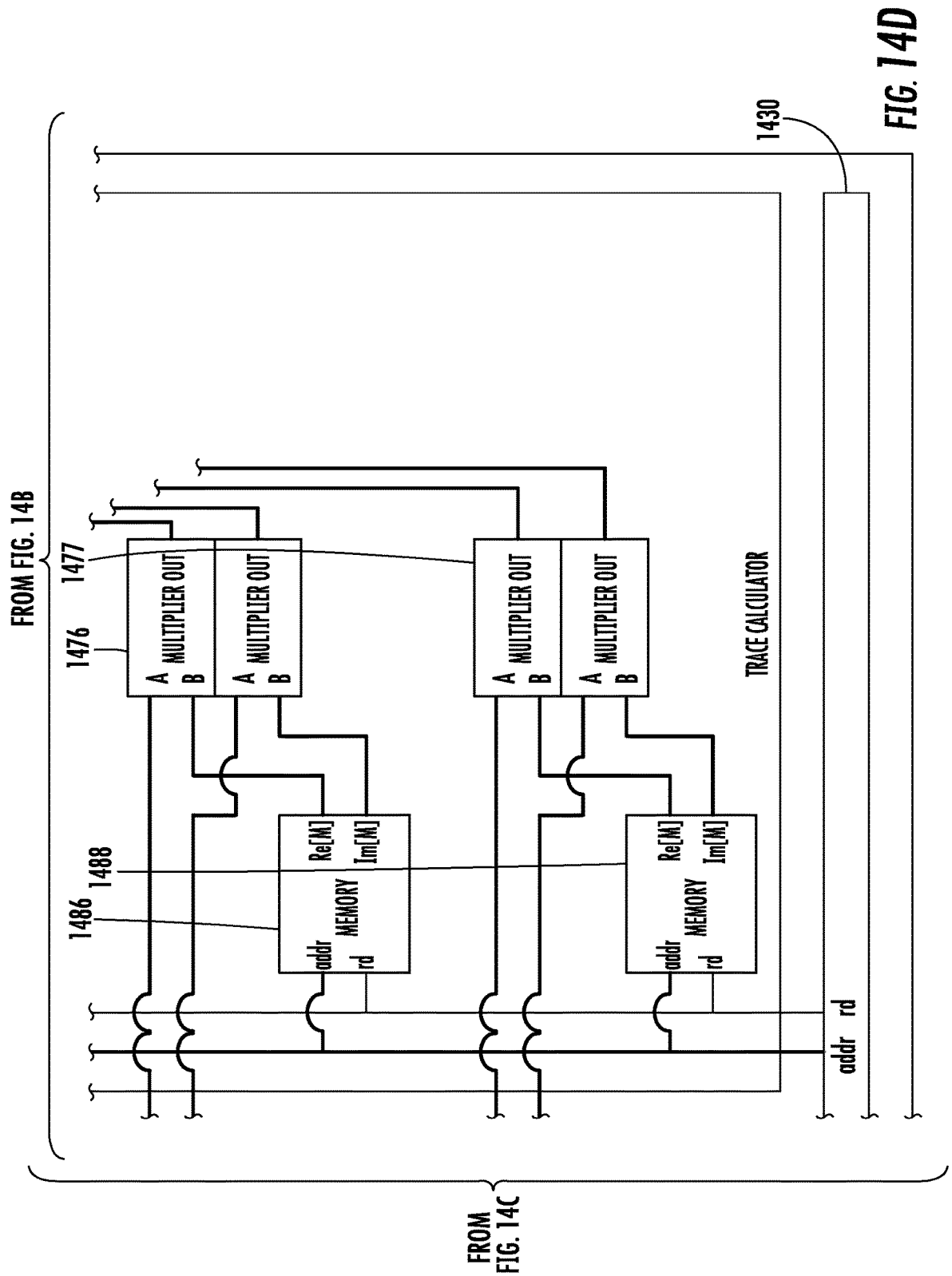

FIG. 13 presents a double register bank formed by combining two of the previously described circularly wired register banks. Both register banks receive the same serial data sA 1311, sB 1312, sC 1313, and sD 1314. Each bank is controlled by separate clk signals 1332 and 1334 and separate s/p signals 1342 and 1344. Each bank also has its own set of 4-word, 6-bit wide parallel outputs. The top register outputs O1A-O1D 1321-1324 while the second register outputs O2A-O2D 1326-1329. This design allows one set of data to be shifted through its register while the other is held in position. The left panel of FIG. 13 shows a detailed view of the double register bank, while the right panel shows a simplified view of the same circuit.

FIGS. 14A-D present a circuit incorporating a coherence calculator 1430 and a single trace calculator 1440. This design is intended to represent a single, easily presented embodiment of the present disclosure. Alternative embodiments might incorporate multiple trace calculators. In one embodiment described herein, a total of three trace calculators would be employed to estimate the contribution to coherence of noise, target regions along the look-direction (mainlobe contributions), and target regions away from the look-direction (sidelobe contributions). The coherence calculator presented here accepts a total of 8 serial signals corresponding to the real 1402-1405 and imaginary 1406-1409 components of received echo signals. The presented design incorporates two double registers, one of which 1452 holds real data, and the other of which 1454 holds imaginary data. The outputs of the double registers are wired to a four complex multipliers 1462, 1464, 1466, and 1468. These registers and multipliers are configured to compute the complex covariances of the input echo data. The top multiplier computes:

$$(Re[s1]+i*Im[s1])(Re[sj]-i*Im[sj])$$

Where s1 is the signal from the $1^{st}$ transducer element, sj is the signal from the $j^{th}$ transducer element, Re[x] is the real component of signal x, and Im[x] is the imaginary component of signal x. The jth signal is selected by employing the circularly wired register bank to shift data across the array. Note that if each sample is shifted once then the data from channel 1 align with channel 2, 2 with 3, 3 with 4, and 4 with 1. This means that three of four multipliers will compute covariance values for a one element shift, while one multiplier computes a covariance value for a three element shift. This matter can be easily managed in the trace calculator by working with signal models that incorporate the expected shifts.

Note that the "Negate" component 1440-1443 is used to change the invert the sign of the imaginary component of the $j^{th}$ signal. This step may be necessary as the covariance between two complex signals is computed by multiplying the first signal by the complex conjugate of the second signal. The complex conjugate is equivalent to the negated sign of the imaginary component. The "Negate" operator can be applied in a number of ways, depending upon the way in which samples are encoded digitally. The simplest approach is to use signed binary coding, in which case negating a signal is performed by simply inverting the sign bit.

The coherence calculator sequentially outputs the portions of the covariance matrix to the trace calculator. Each portion of the covariance matrix (in this embodiment) consists of four complex values corresponding to each of four element pairs. As shown elsewhere, the fact that both the covariance matrix and the models are Hermitian significantly simplifies the mathematics. The model function is distributed across a set of memory banks 1482, 1484, 1486, and 1488 each of which holds real and imaginary model components for the shifts expected to be associated with that memory bank. The outputs of the memory banks are multiplied by the covariance estimates using simple (not complex) multipliers 1470-1477. The outputs of the multipliers are summed by summer 1490 and these summed values are accumulated by accumulator 1492 across the full set of element shifts. In the case of this example there will be a total of four shifts. For each shift a total of four covariance values were calculated so that with a total of four shifts the total of sixteen covariances are output. These sixteen values correspond to each of the covariance values in the covariance matrix.

Figure 15:
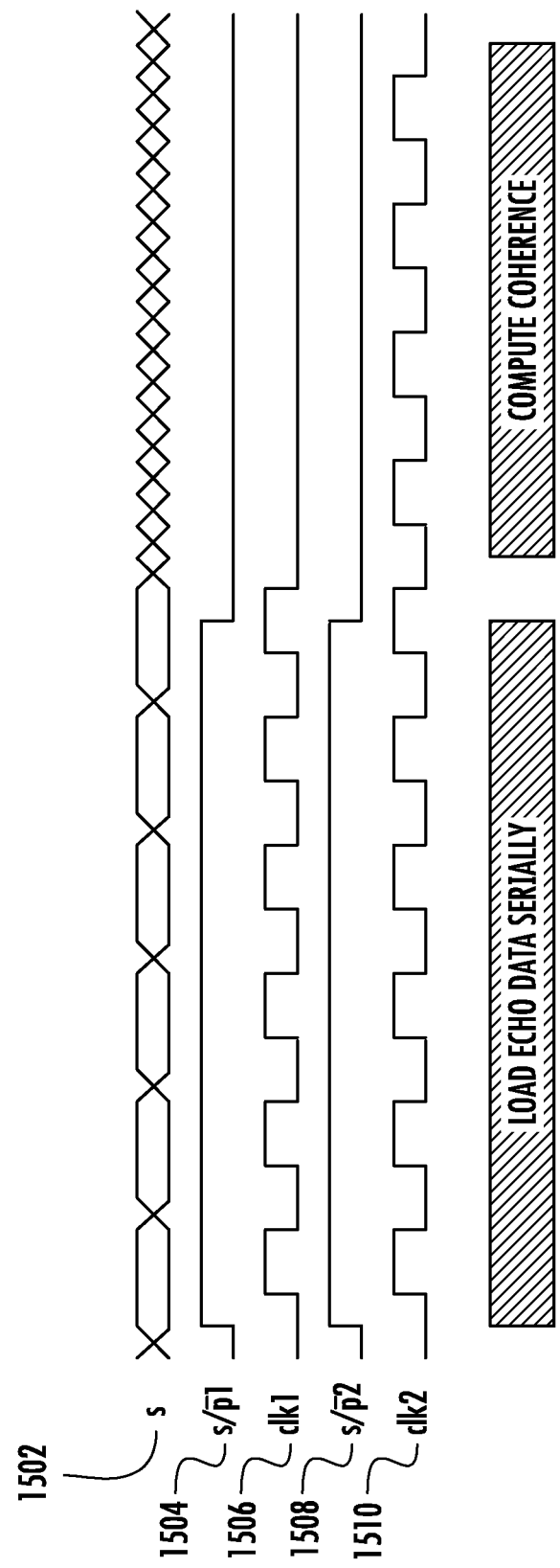
FIG. 15 is a diagram of an example set of control signals according to some embodiments.

The loading of data and shifting of the circularly wired registers is controlled by controlled 1430. An example set of control signals for the controlled are presented in FIG. 15. Serial input data 1502 is latched in the registers by clk1 1506 and clk2 1510 when s/p1 1504 and s/p2508 are high. Note that a total of six rising edges are used to latch in each of the six data bits on these channels. After the registers are fully loaded signal clk2 cycles in order to shift the parallel data through the registers. The outputs are assumed to be multiplied immediately as the data is output, but of course a detailed implementation would latch this data and use another clock signal to trigger the multipliers, memories, summer, and accumulator. Memory addresses (also not shown) would be used to cycle through the model values corresponding to each shift value. The output trace value is used to estimate the contribution of the model to the measured coherence.

The embodiment of FIGS. 14A-D and 15 is intended to illustrate a functional design at a high level. Those experienced in digital hardware will appreciate that improvements can be made through simple modifications. For example, signal integrity can generally be improved by adding latching between circuit stages. Latches would require additional signals in order to control the latches and maintain proper signal timing. These modifications will be readily apparent to those experienced in digital design.

Ultrasound imaging systems will likely use well more than four channels. An example system might contain 64 receive channels. A 64 receive channel system would require 64 complex multipliers (equivalent to 4×64=256 real multipliers) to implement the coherence calculator. An additional 64×2 multipliers would be required for each trace calculator. If we assume three models, then a total of 10×64=640 real multipliers would be required to implement the disclosed invention. This design could be implemented in the Xilinx XC7A200T FPGA, which includes 740 DSP slices, each of which incorporates a multiplier. Other, more complex FPGAs could be used for more complex designs. However, any suitable number of channels may be used.

Estimators

In some embodiments, the estimator 150 in FIG. 1 may be a maximum likelihood estimator. In some embodiments, a maximum likelihood estimator may be used to estimate the contributions of two coherence models. It should be understood that the following example is a nonlimiting exemplary embodiment. For example, the contributions of more than two coherence models may be used.

The probability density model for a multivariate, zero-mean, complex Gaussian is given by (Van Trees, Detection Estimation and Modulation Theory Part I, Wiley, 2013):

$$p_{x|\theta}(x|\theta) = \frac{1}{\pi^N |K(\theta)|} \exp\{-x^H K^{-1}(\theta)x\}\} \quad (1)$$

where x is the N×1 input data, the covariance $K(\theta)$ is a known function of an unknown parameter vector $\theta$, and the conjugate transpose is represented by H. The log-likelihood function is given by:

$$l(\theta,x) = -\ln|K(\theta)| - x^H K^{-1}(\theta)x \quad (2)$$

We define a system with two constituent N×N input covariance models A and B, with respective weights $w_A$ and $w_B$. Let a third matrix, C, denote the weighted superposition of A and B, such that:

$$C = \delta A + B \quad (3)$$

Additionally, we define our model covariance matrix $K(\theta)$ such that:

$$K(\theta) = \alpha C \quad (4)$$

$$K(\theta) = \alpha(\delta A + B) \quad (5)$$

where $\theta = [\alpha, \delta]$, and $K(\theta) = K(\alpha, \delta)$. The matrix weights are given by $w_A = \alpha\delta$ and $w_B = \alpha$, where $\delta = w_A/w_B$. Substituting (4) into (2):

$$l(x,\theta) = -\ln|\alpha C| - x^H(\alpha C)^{-1} x \quad (6)$$

Given:

$$|\alpha C| = \alpha^N |C| \quad (7)$$

$$(\alpha C)^{-1} = \frac{1}{\alpha} C^{-1} \quad (8)$$

We can derive the following:

$$l(x, K(\alpha, \delta)) = -\ln(\alpha^N |C|) - x^H \left(\frac{1}{\alpha} C^{-1}\right) x \quad (9)$$

$$l(x, K(\alpha, \delta)) = -\ln \alpha^N - \ln|C| - \frac{1}{\alpha}(x^H C^{-1} x) \quad (10)$$

$$l(x, K(\alpha, \delta)) = -N \ln \alpha - \ln|C| - \frac{1}{\alpha}(x^H C^{-1} x) \quad (11)$$

We seek the values of $\alpha$ and $\delta$ to maximize our likelihood function: $l(x, K(\alpha, \delta))$, yielding the following estimator:

$$[\hat{\alpha}_{ml}, \hat{\delta}_{ml}] = \arg \max_{\alpha, \delta} \{l(x, K(\alpha, \delta))\} \quad (12)$$

To analytically calculate the maximum corresponding to $\alpha$ we take the derivative of the likelihood function in (12) with respect to $\alpha$.

$$\frac{\partial l(x, K(\alpha, \delta))}{\partial \alpha} = -\frac{N}{\alpha} + \frac{1}{\alpha^2}(x^H C^{-1} x) \quad (13)$$

Setting (13) equal to zero:

$$0 = -\frac{N}{\alpha} + \frac{1}{\alpha^2}(x^H C^{-1} x) \quad (14)$$

$$\frac{N}{\alpha} = \frac{1}{\alpha^2}(x^H C^{-1} x) \quad (15)$$

We can analytically derive the estimate of $\alpha$:

$$\hat{\alpha}_{ml} = \frac{1}{N}(x^H C^{-1} x) \quad (16)$$

Substituting (16) into (11), our likelihood function reduces to:

$$l(x, K(\hat{\alpha}_{ml}, \delta)) = -N \ln \hat{\alpha}_{ml} - \ln|C| - \frac{1}{\frac{1}{N}(x^H C^{-1} x)}(x^H C^{-1} x) \quad (17)$$

$$l(x, K(\hat{\alpha}_{ml}, \delta)) = -N \ln \hat{\alpha}_{ml} - \ln|C| - N \quad (18)$$

Such that the estimator is reduced to a single variable:

$$\hat{\delta}_{ml} = \arg \max_\delta \{l(x, K(\hat{\alpha}_{ml}, \delta))\} \quad (19)$$

Given a model $K(\theta) = \alpha(\delta A + B)$, the estimate of a can be calculated analytically from the input data x and the estimate of $\delta$ can be determined numerically from a 1-D search for the maximum value of (19). Thus, a two-parameter estimation problem with weights $w_A = \alpha\delta$ and $w_B = \alpha$ can be determined from a 1-D maximum likelihood search.

Coherence Models

We claim a realization in which the coherence is measured from one or more regions of the target and the coherence model(s) used to calculate pixel values is derived from those measured coherence(s). The measured coherence could also be acquired at various times and under differing transmit beam parameters. The coherence models may be updated with subsequent transmit firings.

The imaging system could include one or more control parameters that modify the features of the coherence model. The control parameters could be adjusted by the scanner operator or automatically adjusted using image quality feedback parameters. Example features that may be modified include the coherence length, windowing of the coherence models, adjusting the spatial regions of interest that define the coherence models, and changing the number of regions of interest and number of coherence models.

The coherence or similarity function could be calculated in myriad ways. Mathematical methods of estimating coherence, or similarity, include normalized correlation, covariance, sum-absolute difference, sum-squared difference, phase-based estimators such as those described by Loupas (Loupas et. al., "An axial velocity estimator for ultrasound blood flow imaging, based on a full evaluation of the Doppler equation by means of a two-dimensional autocorrelation approach," *IEEE Trans. Ultrason. Ferroelect. Freq. Control*, vol. 42, pp. 672-688, 1995) and Kasai (Kasai et. al., "Real-time two-dimensional blood flow imaging using an autocorrelation technique," *IEEE Trans. Son. Ultrason.*, vol. 32, pp. 458-464, 1985), estimators using L1, L2 or higher norms, and others. The coherence function could also be calculated with angular coherence (Li & Dahl, "Angular coherence in ultrasound imaging: theory and applications,"

*The Journal of the Acoustical Society of America*, vol. 141, no. 3, 2017). One or more coherence models may be selected based on an adaptive coherence estimation.

Some realizations of the method could use specialized transmit pressure waveforms, with coherence measurements performed on echoes from either individual realizations or combinations of these transmitted waveforms. Examples of specialized waveforms include limited diffraction beams (J. Liu, "2D and 3D high frame rate imaging with limited diffraction beams," *IEEE Trans. Ultrason. Ferroelect., Freq. Control*, vol. 44, no. 4, 1997), X-waves (Liu and Greenleaf, "Nondiffracting X-waves-exact solutions to free space scalar wave equation and their finite aperture realizations," *IEEE Trans. Ultrason. Ferroelect. Freq. Control*, vol. 39, no. 1, 1992), Bessel beams (Durnin et. al., "Diffraction-free beams," *Phys. Rev. Lett.*, vol. 58, no. 15, 1987), beams generated with apodized transmit apertures, beams with apodization or phasing intended to create multiple mainlobes or boosted sidelobes or grating lobes, and other transmit waveforms.

The method could calculate coherence estimates from echoes at the fundamental frequency, harmonic frequencies, or combinations of the fundamental and harmonic frequencies. Harmonic echoes could be generated by using pulse inversion, filtering, or other amplitude modulation methods.

The method could be combined with advanced beamforming methods, such as Multi-covariate Imaging of Subresolution Targets (MIST) (Morgan et al., "Multi-covariate imaging of sub-resolution targets," *IEEE Trans. Med. Imag.*, vol. 38, no. 7, pp. 1690-1700), coded excitation (Chiao and Hao, "Coded excitation for diagnostic ultrasound: a system developer's perspective," 2003 *IEEE Ultrasonics Symposium*, vol. 1, pp. 437-448), Hadamard coding (R. Y. Chiao, L. J. Thomas, S. D. Silverstein, "Sparse array imaging with spatially-encoded transmits", *Proc. IEEE Ultrason. Symp.*, pp. 1679-1682, October 1997), REFoCUS (Bottenus, N., "Recovery of the complete data set from focused transmit beams," *IEEE Trans. Ultrason. Ferroelect. Freq. Control*, vol. 65, no. 1, 2018), synthetic transmit and/or receive aperture methods (Karaman et. al., "Synthetic aperture imaging for small scale systems," *IEEE Trans. Ultrason. Ferroelect. Freq. Control*, vol. 42, no. 3, 1995, Bae & Jeong, "A study of synthetic aperture imaging with virtual source methods in B-mode ultrasound imaging systems," *IEEE Trans. Ultrason. Ferroelect., Freq. Control*, vol. 47, no. 6, 2000), and similar methods.

The coherence estimates could be formed using radio-frequency or I/Q echo data.

The method could use a wide range or transducer array geometries, including linear, phased, curvilinear, curved, convex, annular and concave arrays. Those arrays could be 1D, 1.25D, 1.5D, 1.75D (Wildes et. al., "Elevation performance of 1.25D and 1.5D transducer arrays," *IEEE Trans. Ultrason. Ferroelect., Freq. Control*, vol. 44, no. 5, 1997), or 2-D matrix arrays. These arrays could be fully sampled, sparse or minimally redundant designs (Karaman et. al. "Minimally redundant 2-D array designs for 3-D medical ultrasound imaging," *IEEE Trans. Med. Imag.*, vol. 28, no. 7, 2009).

This method could be used with signals from subapertures of array elements which have been delayed and summed (Savord and Soloman, "Fully sampled matrix transducer for real-time 3D ultrasonic imaging," 2003 *IEEE International Ultrasonics Symposium*, vol. 1, pp. 945-953, 2003).

The coherence contributions could be estimated using myriad estimator methods, including least squares, maximum likelihood, minimum mean square error, maximum a posteriori, minimum variance unbiased, and Bayes estimators.

The coherence models could be determined from myriad sources, including numerical simulations, models predicted by analytic or theoretical expressions in the literature (Mallart & Fink, "The van cittert-zernike theorem in pulse-echo measurements," *The Journal of the Acoustical Society of America*, vol. 90, no. 5, 1991, and Long et. al., "Lag-one coherence as an image quality metric," *IEEE Trans. Ultrason., Ferroelect., Freq. Control*, vol. 65, no. 10, 2018), and Morgan et al., "Speckle coherence of piecewise-stationary stochastic targets," *The Journal of the Acoustical Society of America*, vol. 146, no. 3, 2019), and a priori or in situ measurements of coherence."

The coherence models may vary throughout the spatial field of view, such as a depth-dependent coherence model to account for the effects of the limited depth of field associated with transmit focusing, receive aperture growth, or an angle-dependent model to account for the effects of steering. Coherence models may be spatially varied to account for different transmit configurations used to interrogate regions of interest in the target.

Covariance models may describe myriad signal, clutter, or noise models. Signal models may include the predicted covariance of backscatter from diffuse targets, either spatially homogeneous or spatially inhomogeneous. Signal models may also include covariances from a number of spatial regions of interest within the target, including the main lobe, side lobes or grating lobes of a focused ultrasound beam. Clutter and noise models may describe incoherent components (such as an identity covariance matrix) (Pinton et. al., "Sources of image degradation in fundamental and harmonic ultrasound imaging using nonlinear, full-wave simulations," *IEEE Trans. Ultrason. Ferroelect. Freq. Control*, vol. 58, no. 4, 2011, and Long et. al., "Lag-one coherence as an image quality metric," *IEEE Trans. Ultrason., Ferroelect., Freq. Control*, vol. 65, no. 10, 2018), or partially coherent components with limited spatial coherence at short lags. Clutter models may also describe off-axis targets or aberrating sources (Walker and Trahey, "Speckle coherence and implications for adaptive imaging," *The Journal of the Acoustical Society of America*, vol. 101, no. 4, pp. 1847-1858, 1997).

This method could be used in myriad applications involving spatial compounding, including receive spatial compounding, transmit spatial compounding (with electronically or mechanically translating transmit aperture or multiple transmit pulses), or a combination of transmit and receive spatial compounding (Shattuck and von Ramm, "Compound scanning with a phased array," *Ultrasonic Imaging*, vol. 4, no. 2, 1982, and Trahey et. al., "Speckle pattern correlation with lateral aperture translation: experimental results and implications for spatial compounding," *IEEE Trans. Ultrason., Ferroelect., Freq. Control*, vol. 33, no. 3, 1986).

This method could be used with frequency compounding (Trahey et. al., "A quantitative approach to speckle reduction via frequency compounding," *Ultrasonic Imaging*, vol. 8, no. 3, 1986). Coherence contributions could be estimated from sub-bands of frequencies within the pulse bandwidth, and averaged, summed, or otherwise combined.

This method may be used with repeated transmit events. Multiple transmissions at varying focal depths may be performed, and coherence estimates obtained from echoes received from each transmission may be combined. Transmit events in the same look direction may be repeated with varying apodization schemes or specialized waveforms. Transmit events may also be repeated with varying frequency.

The coherence calculator may calculate a number of covariances, including the complete covariance matrix, a sparse covariance matrix, or a covariance matrix in which long lags are not calculated.

The coherence calculator may involve averaging or otherwise combining of the coherence estimate in depth, azimuth, or time. In the case of spatial averaging, the calculator may employ a moving average for the coherence estimate to reduce redundant calculations. Coherence estimates across spatial regions may be weighted or windowed based on proximity to the point or region of interest. Temporal averaging of the coherence estimates may involve a persistence factor.

The coherence model may be a spatial covariance model, an angular covariance model and/or a noise model.

The coherence calculator and/or estimator may include analog, digital, or a combination of analog and digital circuitry and hardware for mathematical operations.

This method may be used to characterize the properties of biological tissues or other materials, including sound speed, attenuation, and density.

Trace Calculator

Some embodiments of the present invention incorporate a "trace calculator" as shown in FIGS. 14A-D. Mathematically the "trace calculator" computes the following expression:

$$Tr[A^H \hat{R}] \quad (1)$$

Where $A^H$ is Hermitian Transpose of the model component and $\hat{R}$ is the covariance estimated from the received signal. (Note that this example considers only a single model component, however the approach described here is equally valid for cases with multiple model components.) Equation (1) can be rewritten as:

$$Tr[A^H \hat{R}] = \sum_{i=1}^{N} \sum_{j=1}^{N} conj[A_{ij}] \hat{R}_{ij} \quad (2)$$

Where the subscript notation indicates the indices into the array elements and the conj operator indicates the complex conjugate operation. We can gain insights into this expression by considering the real and imaginary components of the constituent elements, as shown below:

$$Tr[A^H \hat{R}] = \sum_{i=1}^{N} \sum_{j=1}^{N} (\text{Re}[A_{ij}] - j*\text{Im}[A_{ij}])(\text{Re}[\hat{R}_{ij}] + j*\text{Im}[\hat{R}_{ij}]) \quad (3)$$

This expression is simpler than it first appears. The model matrix and the estimated covariance matrix are both Hermitian matrices; that is they exhibit conjugate symmetry. For a Hermitian matrix A, $$A_{ij} = conj[A_{ji}] \quad (4)$$

Which can be expressed in terms of real and imaginary components as:

$$\text{Re}[A_{ij}] + j*\text{Im}[A_{ij}] = \text{Re}[A_{ji}] - j*\text{Im}[A_{ji}] \quad (5)$$

For the main diagonal Hermitian matrices are always purely real:

$$A_{ii} = \text{Re}[A_{ii}] \quad (6)$$

Equation (3) can be broken into constituent components as follows:

$$Tr[A^H \hat{R}] = \sum_{i=1}^{N} conj[A_{ii}] \hat{R}_{ii} + \sum_{i=1}^{N-1} \sum_{j=i+1}^{N} (conj[A_{ij}] \hat{R}_{ij} + conj[A_{ji}] \hat{R}_{ji}) \quad (7)$$

Expanding terms in equation (7) yields:

$$Tr[A^H \hat{R}] = \sum_{i=1}^{N} A_{ii} \hat{R}_{ii} + \sum_{i=1}^{N-1} \sum_{j=i+1}^{N} \left( \begin{array}{l} (\text{Re}[A_{ij}] - j*\text{Im}[A_{ij}])(\text{Re}[\hat{R}_{ij}] + j*\text{Im}[\hat{R}_{ij}]) + \\ (\text{Re}[A_{ji}] - j*\text{Im}[A_{ji}])(\text{Re}[\hat{R}_{ji}] + j*\text{Im}[\hat{R}_{ji}]) \end{array} \right) \quad (8)$$

Substituting equations (5) and (6) into (8) yields:

$$Tr[A^H \hat{R}] = \sum_{i=1}^{N} A_{ii} \hat{R}_{ii} + \sum_{i=1}^{N-1} \sum_{j=i+1}^{N} \left( \begin{array}{l} (\text{Re}[A_{ij}] - j*\text{Im}[A_{ij}])(\text{Re}[\hat{R}_{ij}] + j*\text{Im}[\hat{R}_{ij}]) + \\ (\text{Re}[A_{ji}] + j*Im[A_{ji}])(\text{Re}[\hat{R}_{ji}] - j*Im[\hat{R}_{ji}]) \end{array} \right) \quad (9)$$

Simplifying (9) yields:

$$Tr[A^H \hat{R}] = \sum_{i=1}^{N} \text{Re}[A_{ii}] \text{Re}[\hat{R}_{ii}] | \sum_{i=1}^{N-1} \sum_{j=i+1}^{N} (2 \text{Re}[A_{ij}] \text{Re}[\hat{R}_{ij}]) | 2\text{Im}[A_{ij}] \text{Im}[\hat{R}_{ij}]) \quad (10)$$

Regrouping terms yields:

$$Tr[A^H \hat{R}] = \sum_{i=1}^{N} \sum_{j=1}^{N} (\text{Re}[A_{ij}] \text{Re}[\hat{R}_{ij}] + \text{Im}[A_{ij}] \text{Im}[\hat{R}_{ij}]) \quad (11)$$

Equation (11) shows that because both the model and the covariance estimate are Hermitian, the trace can be computed by simply multiplying and summing the real components and the imaginary components of the two matrices. This significantly simplifies the required mathematics to be employed in a programmable system (such as a GPU) or the hardware multipliers and adders employed in a hardware system such as an FPGA.

It should be apparent from the above derivation that the symmetry of the model and estimated covariance matrices allows further simplification. Although this simplification is not employed in the design of FIGS. 14A-D, one of ordinary skill in digital hardware design will be able to modify the design to take advantage of this symmetry.

Combined "Deterministic" and "Stochastic" Targets

For most biological targets it is appropriate to model the scattering field as a combination of distributed, unresolvable scatterers. These situations can be effectively modeled as "stochastic" targets, the statistical properties of which can be modeled using the coherence models previously described. In some cases however the scattering field may include one or more distinct targets that are potentially resolvable. We can consider these scattering fields to consist of discrete "deterministic" targets and distributed, unresolvable "stochastic" targets. This section derives a model for these "combined" targets and describes a method by which their contributions can be estimated.

We model the received signal as a 1×N complex vector:

$$r \quad (1)$$

where N is the number of elements in the receive array. We are interested in finding a least squares solution for both the deterministic component of the received signal and the stochastic component of the received signal. We model the stochastic signal as the received signal minus a deterministic component:

$$s = r - \beta B \quad (2)$$

where s is a 1×N complex vector, β is a 1×$N_B$ complex vector (where $N_B$ is the number of modeled deterministic components), and B is a $N_B$×N complex array with each row being a single modeled deterministic component. We estimate the covariance of the stochastic signal component by taking the conjugate outer product of the stochastic component:

$$S = s^H s \quad (3)$$

The error matrix between the covariance and a model covariance is:

$$E = S - \Sigma_{i=1}^{N_A} \alpha_i^2 A_i \quad (4)$$

where $\alpha_i^2$ is a positive real scalar, and $A_i$ is a N×N Hermitian symmetric matrix. The error can be quantified by computing the squared Frobenius norm of the error matrix from equation (4).

$$\|E\|_F^2 = Tr(EE^H) \quad (5)$$

where Tr is the trace operator. Substituting (4) into (5) yields:

$$\|E\|_F^2 = Tr\left(\left(S - \sum_{i=1}^{N_A} \alpha_i^2 A_i\right)\left(S - \sum_{j=1}^{N_A} \alpha_j^2 S_j\right)^H\right) \quad (6)$$

expanding (6) yields:

$$\|E\|_F^2 = \quad (7)$$
$$Tr\left(SS^H - S\left(\sum_{j=1}^{N_A} \alpha_j^2 A_j\right)^H - \left(\sum_{i=1}^{N_A} \alpha_i^2 A_i\right)S^H + \left(\sum_{i=1}^{N_A} \alpha_i^2 A_i\right)\left(\sum_{j=1}^{N_A} \alpha_j^2 A_j\right)^H\right)$$

$$\|E\|_F^2 = Tr\left(SS^H - \sum_{j=1}^{N_A} \alpha_j^2 SA_j^H - \sum_{i=1}^{N_A} \alpha_i^2 A_i S^H + \left(\sum_{i=1}^{N_A} \sum_{j=1}^{N_A} \alpha_i^2 \alpha_j^2 A_i A_j^H\right)\right) \quad (8)$$

$$\|E\|_F^2 = Tr(SS^H) - Tr\left(\sum_{j=1}^{N_A} \alpha_j^2 SA_j^H\right) - \quad (9)$$
$$Tr\left(\sum_{i=1}^{N_A} \alpha_i^2 A_i S^H\right) + Tr\left(\sum_{i=1}^{N_A} \sum_{j=1}^{N_A} \alpha_i^2 \alpha_j^2 A_i A_j^H\right)$$

since $A_i$ is a real matrix, $A_i = A_i^H$ and (9) can be rearranged to yield:

$$\|E\|_F^2 = Tr(SS^H) - \sum_{j=1}^{N_A} \alpha_j^2 \, Tr(SA_j^H) - \quad (10)$$
$$\sum_{i=1}^{N_A} \alpha_i^2 Tr(A_i S^H) + \sum_{i=1}^{N_A} \sum_{j=1}^{N_A} \alpha_i^2 \alpha_j^2 \, Tr(A_i A_j^H)$$

Since S and $A_i$ are Hermitian symmetric, $Tr(SA_i^H) = Tr(A_i S^H)$, (10) can be rearranged to yield:

$$\|E\|_F^2 = Tr(SS^H) - 2\sum_{j=1}^{N_A} \alpha_j^2 \, Tr(A_i S^H) + \sum_{i=1}^{N_A} \sum_{j=1}^{N_A} \alpha_i^2 \alpha_j^2 Tr(A_i A_j^H) \quad (11)$$

where:

$$S = s^H s = (r - \beta B)^H (r - \beta B) \quad (12)$$

Equation 11 can be minimized numerically to yield estimates of β (the weights of the $N_B$ "deterministic" targets) and the various $\alpha_i^2$ (the weights of the $N_A$ stochastic targets).

Alternatively, the weights can be found by solving a set of simultaneous equations formed by taking the derivatives of (11) with regard to the "stochastic" and "deterministic" weights and setting them equal to zero.

Adjustment of Echo Data Using Weighted Estimates of Coherence Models

As described above, ultrasound images may be generated based on the weights of the coherence models directly. However, in some embodiments the estimated weights of the coherence models may be used to modify or adjust the echo data itself, and an image may be generated based on the echo data as modified by estimated weights of the coherence models. Example embodiments of coherence model modified echo data are provided below.

In some embodiments, the echo signals could be modified by use of a filter. That is, the image generator described herein may be replaced with or include a "filter generator." The filter generator may modify the echo signals using the coherence models as described herein, and the modified or filtered echo signals may be processed, for example, according to standard echo signal processing as described below and/or the tissue may be characterized based on echo signal processing techniques described below.

A Wiener filter is one embodiment of a modification of the echo data. Other methods are possible, including Kalman, least squares, or other linear or nonlinear, time variant or invariant, or finite or infinite impulse response filters.

Some embodiments may use the coherence contribution estimates to filter the echo signals to isolate echo signals corresponding to a coherence model of interest, or to remove echo or noise signals corresponding to coherence models not of interest. The coherence models used to design the filter may be any of the models listed in the specifications. A sample Wiener filter embodiment is presented in the specifications.

The filter parameters could be determined based on measured data, or "adaptively determined". The coherence models may be adaptively determined from measured echo data. The estimated contributions of the adaptively-determined coherence models may be determined by the estimator, and the contributions of the adaptively-determined coherence models may be used as parameters in the Wiener filter. The adaptively-determined coherence models, coherence model contribution estimations, and Wiener filter parameters may vary as a function of location in the image.

The modified echo signals may be used for myriad applications either in their filtered form or as the beamsum of the filtered echo signals:

Conventional imaging

Doppler ultrasound or flow estimation

Speckle tracking (Bohs, Laurence N., and Gregg E. Trahey. "A novel method for angle independent ultrasonic imaging of blood flow and tissue motion." IEEE Transactions on Biomedical Engineering 38.3 (1991): 280-286), Elastography or strain imaging (Ophir, Jonathan, et al. "Elastography: ultrasonic estimation and imaging of the elastic properties of tissues." Proceedings of the Institution of Mechanical Engineers, Part H: Journal of Engineering in Medicine 213.3 (1999): 203-233.)

Displacement estimation (Pinton, Gianmarco F., Jeremy J. Dahl, and Gregg E. Trahey. "Rapid tracking of small displacements with ultrasound." IEEE transactions on ultrasonic, ferroelectrics, and frequency control 53.6 (2006): 1103-1117.)

Acoustic radiation force-based methods intended for imaging or quantitative measurements (Nightingale, Kathryn R., et al. "On the feasibility of remote palpation using acoustic radiation force." The Journal of the Acoustical Society of America 110.1 (2001): 625-634., or Sarvazyan, Armen P., et al. "Shear wave elasticity imaging: a new ultrasonic technology of medical diagnostics." Ultrasound in medicine & biology 24.9 (1998): 1419-1435.)

Phase or aberration correction (Flax, S. W., and Matthew O'Donnell. "Phase-aberration correction using signals from point reflectors and diffuse scatterers: Basic principles." IEEE transactions on ultrasonics, ferroelectrics, and frequency control 35.6 (1988): 758-767.)

Tissue characterization (Linzer, Melvin, and Stephen J. Norton. "Ultrasonic tissue characterization." Annual review of biophysics and bioengineering 11.1 (1982): 303-329.)

Wiener Filtering of Channel Echo Data

The following example calculation may be used to adjust echo data using weighted estimates of coherence models according to some embodiments.

Consider our observed signal y to be a sum of constituents originating from a signal of interest, a, a signal not of interest, b, and a noise term, n, weighted by scalars $\alpha$, $\beta$, and $\gamma$, respectively. Vectors y, a, b, and it are of shape N×1.

$$y = \alpha a + \beta b + \gamma n \quad (1)$$

We define a N×1 signal of interest, x, as the weighted contribution of the region of interest, a, to the measured data $$x = \alpha a \quad (2)$$

We define an estimator to estimate the signal of interest $\hat{x}$ as a linear function of the observation y:

$$\hat{x} = Ky \quad (3)$$

where K is a N×N matrix that minimizes the mean-squared error between $\hat{x}$ and the linear estimate Ky. Using the principle of orthogonality (Scharf, Statistical Signal Processing: Detection, Estimation, and Time-Series Analysis, Addison-Wesley, 1991) we assume the estimator satisfies the following condition:

$$\langle (x - Ky)y^H \rangle = 0 \quad (4)$$

where $\langle \rangle$ is the expected value operator and H is the Hermitian transpose. Expanding terms, we have:

$$\langle xy^H \rangle - \langle Kyy^H \rangle = 0 \quad (5)$$

We define the covariance $xy^H$ as:

$$R_{xy} = \langle xy^H \rangle \quad (6)$$

and the covariance $yy^H$ as:

$$R_{yy} = \langle yy^H \rangle \quad (7)$$

Substituting (6) and (7) into (5):

$$R_{xy} - KR_{yy} = 0 \quad (8)$$

$$K = R_{xy} R_{yy}^{-1} \quad (9)$$

where the estimated signal of interest $\hat{x}$ is given by (3). We then solve for the covariances $R_{xy}$ and $R_{yy}$ using the definitions in (1) and (2).

Substituting (1) and (2) into (6), and expanding terms $$R_{xy} = \langle (\alpha a)(\alpha a + \beta b + \gamma n)^H \rangle \quad (10)$$

$$R_{xy} = \langle \alpha^2 aa^H + \alpha\beta ab^H + \alpha\gamma an^H \rangle \quad (11)$$

Exchanging the order of summation and expected value:

$$R_{xy} = \langle \alpha^2 aa^H \rangle + \langle \alpha\beta ab^H \rangle + \langle \alpha\gamma an^H \rangle \quad (12)$$

$$R_{xy} = \langle \alpha^2 aa^H \rangle + \langle \alpha\beta ab^H \rangle + \langle \alpha\gamma an^H \rangle \quad (13)$$

The signal constituents are assumed uncorrelated, such that $\langle ab^H \rangle = \langle an^H \rangle = 0$. Therefore, the expected cross covariance $R_{xy}$ is given by:

$$R_{xy} = \alpha^2 \langle aa^H \rangle \quad (14)$$

where the covariance of the signal of interest a can be defined as $R_a = \langle aa^H \rangle$, such that $$R_{xy} = \alpha R_a \quad (15)$$

Similarly, the covariance $R_{yy}$ can be solved by substituting (1) into (7), and expanding terms:

$$R_{yy} = \langle (\alpha a + \beta b + \gamma n)(\alpha a + \beta b + \gamma n)^H \rangle \quad (16)$$

$$R_{yy} = \langle \alpha^2 aa^H + \alpha\beta ab^H + \alpha\gamma an^H + \beta\alpha ba^H + \beta^2 bb^H + \beta\gamma bn^H + \gamma\alpha na^H + \gamma\beta nb^H + \gamma^2 nn^H \rangle \quad (17)$$

Exchanging the order of summation and expected value:

$$R_{yy} = \langle \alpha^2 aa^H \rangle + \langle \alpha\beta ab^H \rangle + \langle \alpha\gamma an^H \rangle + \langle \beta\alpha ba^H \rangle + \langle \beta^2 bb^H \rangle + \langle \beta\gamma bn^H \rangle + \langle \gamma\alpha na^H \rangle + \langle \gamma\beta nb^H \rangle + \langle \gamma^2 nn^H \rangle \#(18)$$

$$R_{yy} = \alpha^2 \langle aa^H \rangle + \alpha\beta \langle ab^H \rangle + \alpha\gamma \langle an^H \rangle + \beta\alpha \langle ba^H \rangle + \beta^2 \langle bb^H \rangle + \beta\gamma \langle bn^H \rangle + \gamma\alpha \langle na^H \rangle + \gamma\beta \langle nb^H \rangle + \gamma^2 \langle nn^H \rangle \#(19)$$

Assuming the signal constituents are uncorrelated, $\langle ab^H \rangle = \langle an^H \rangle = \langle ba^H \rangle = \langle bn^H \rangle = \langle na^H \rangle = \langle nb^H \rangle = 0$, (19) reduces to:

$$R_{yy} = \alpha^2 \langle aa^H \rangle + \beta^2 \langle bb^H \rangle + \gamma^2 \langle nn^H \rangle \quad (20)$$

where the covariance of the signal not of interest b and the noise n can be defined as $R_b = \langle bb^H \rangle$ and $R_n = \langle nn^H \rangle$ such that:

$$R_{yy} = \alpha^2 R_a + \beta^2 R_b + \gamma^2 R_n \quad (21)$$

Substituting (15) and (21) into (9), $$K = (\alpha^2 R_a)(\alpha^2 R_a + \beta^2 R_b + \gamma^2 R_n)^{-1} \quad (22)$$

The filtered echo data estimate $\hat{x}$ is given by:

$$\hat{x} = (\alpha^2 R_a)(\alpha^2 R_a + \beta^2 R_b + \gamma^2 R_n)^{-1} y \quad (23)$$

(23)

where $\alpha^2$, $\beta^2$, and $\gamma^2$ are the variances estimates of the contributions of covariance matrices $R_a$, $R_b$, and $R_n$ to the observed covariance matrix $\hat{R}_y = yy^H$. In one embodiment, these variance estimates are calculated by a least squares minimization:

$$[\alpha^2, \beta^2, \gamma^2] = \arg\min_{\alpha^2, \beta^2, \gamma^2} \| \hat{R}_{yy} - \alpha^2 R_a - \beta^2 R_b - \gamma^2 R_n \|_F^2 \quad (24)$$

where F represents the Frobenius norm.

Embodiments of the present invention are now illustrated with the following non-limiting examples.

INTRODUCTION

A. Coherence of Diffuse Scattering Targets

Coherence in imaging describes the similarity of two points in a wavefield across space and/or time. Many imaging modalities employ coherent processing techniques, which involve the measurement of both the amplitude and phase of the received signal. These methods typically seek to constructively align signal phase on transmission and/or reception to spatially localize energy and improve the signal-to-noise ratio (SNR) of the measurement. Examples of coherent imaging modalities include radar, sonar, ultrasound, stellar interferometry, and monochromatic laser imaging.

Across modalities, many imaging targets contain a combination of deterministic and stochastic components. Deterministic targets are characterized by nonrandom features or boundaries directly resolvable by the imaging system. Stochastic or diffuse targets, however, are described by random, unresolvable microstructure which is rough on the scale of the wavelength. Common examples include biological tissues in medical ultrasound, ground glass diffusers in laser optics, and coarse terrain or vegetative cover on the Earth's surface in radar.

Unlike deterministic targets, stochastic targets are best characterized by average statistical properties. These are typically modeled as statistically stationary and spatially incoherent with uniform scattering strength,[1-4] though more complex models have also sought to incorporate a small but finite coherence length,[4,5] or higher-order structure, such as periodicity, polarization effects, or non-Gaussian scatterer distributions.[6-8] Under coherent radiation, random interference of waves scattered from diffuse targets leads to a granular speckle pattern in the observed image.[2-4,9,10]

Given the prevalence of diffuse targets across applications, the study of speckle has garnered much attention in the imaging literature. Early observations of the speckle phenomenon were documented in the 19th-century physics literature,[11,12] however, modern statistical analysis began in the 1960s with the advent of laser optics.[13-17] The first-order statistics of speckle have been well-characterized, drawing many parallels with the classical analysis of thermal light.[2,4,5,9,18,19] Second-order statistics involving coherence—often quantified in terms of covariance, correlation, or mutual intensity—are described by the van Cittert-Zernike (VCZ) theorem, which provides a mathematical framework expressing the propagation of spatial coherence from an incoherent source distribution.[4,20-22]

The VCZ theorem was first applied to the study of speckle by Goodman, who demonstrated an equivalence between the propagation of mutual intensity from an incoherent optical source and from laser light scattered by rough surfaces.[5] This insight was further extended to pulse-echo ultrasound by Mallart and Fink,[23] who described backscatter from diffuse targets as an incoherent acoustic source, relating the incident energy to the covariance of the backscattered pressure field. Coherence yields myriad insights into the design and analysis of ultrasound imaging systems.[23-31] Many imaging methods employ insights from spatial coherence in the beamforming process, and have shown improvements in image quality over conventional methods.[32-39]

Across modalities, the most common model of diffuse targets assumes stationary statistics with uniform scattering strength. While this model is attractive for analytical calculations (including the derivation of the classical VCZ theorem), it fails to account for local variations in scattering strength common across imaging applications. Under this model, the second-order statistics predicted by the VCZ theorem are a function of the entire source distribution. While nonhomogeneity of the scattering function and changes in the incident energy profile will alter the covariance function,[23,40] the current model does not provide a framework to spatially decompose the covariance into contributions from particular regions of interest.

In this example, we describe the target distribution as piecewise-stationary, in which scattering strength may vary as a function of absolute position. We apply the VCZ theorem to piecewise-stationary targets to demonstrate that the spatial covariance of the received echo data is the linear superposition of covariances from distinct spatial regions. We derive the mathematical basis of this decomposition from first principles, and validate the results through simulation studies demonstrating superposition and scaling over various depths and transmit apodizations, and in the presence of noise. We discuss the implications of this decomposition for imaging applications, and frame this description in the context of existing covariance models in the literature. To our knowledge, the decomposition of covariance into contributions from distinct spatial regions has not been presented elsewhere in the literature.

While the validation studies are specific to ultrasound, the physical insights presented in this work are generally applicable to coherent imaging applications involving stochastic targets. These insights provide the basis for a recently described estimation-based ultrasound image formation method, Multi-covariate Imaging of Sub-resolution Targets (MIST), which images the statistical properties of stochastic targets by estimating on-axis contributions to the ultrasonic echo data.[39]

B. Coherence-Based Imaging in Medical Ultrasound

The conventional approach to beamforming in diagnostic ultrasound imaging relies on a simple geometric model. Using the expected time of flight of acoustic waves in the field, delay-and-sum methods are employed to coherently combine echoes received at the array elements, providing a basis to spatially map the scattering strength of the imaging target. This fundamental paradigm of clinical ultrasound image formation has remained unchanged for many years.

With the advent of software-based processing of ultrasound echo data, many alternatives to the traditional delay-and-sum approach have been proposed to improve image quality over conventional B-Mode imaging. Many of these beamforming methods employ aperture domain spatial coherence as a contrast mechanism. In some cases, beam-summed data are weighted by a spatial coherence metric, as in the Generalized Coherence Factor[34] and Phase Coherence Factor[35]. Other methods directly map pixel brightness to measures of coherence. In short-lag spatial coherence (SLSC) imaging,[36] pixel brightness is determined directly by the spatial coherence of received echoes, integrated up to a maximum lag in the receive aperture. The filtered-delay multiply and sum beamformer (F-DMAS) employs a pair-wise multiplication and square root operation before summation, showing high sensitivity to spatial coherence.[37,38]

Another popular approach is to minimize incoherent noise through a constrained optimization problem. Various implementations of the minimum variance distortionless response (MVDR) beamformer[57,58] have been adapted to diagnostic ultrasound,[59-63] demonstrating reduced sidelobe levels and improved lateral resolution. Wiener filtering has also been applied to the beamforming process,[64] and combined with coherence- and MVDR-based processing.[65,66] Other approaches include aperture domain model image reconstruction (ADMIRE)[67] to model and remove the effects of multipath scattering in the aperture domain, and frequency-space prediction filtering (FXPF)[68] to filter out aperture domain incoherence using an autoregressive model.

Many of the above methods have been shown to improve image quality over conventional B-mode. However, to the extent that the above methods use spatial coherence as a mechanism to distinguish signal and noise, most rely on a general classification scheme to distinguish coherent and incoherent portions of the signal. SLSC and other methods take an ad hoc approach to image formation, only loosely based on a statistical model of ultrasound backscatter, and do not use the entire two-dimensional covariance matrix in the image formation process, thus discarding statistical information which could be used to improve image quality.

In this paper, we apply a piecewise-stationary model to diffuse, sub-resolution targets, in which the covariance of backscattered echoes is the linear superposition of constituents from distinct spatial regions. Under this framework, we derive and validate an estimation-based imaging method to quantify and isolate the contributions of distinct components to the received echo data covariance. We have dubbed this method Multi-covariate Imaging of Sub-resolution Targets, or MIST.

We hypothesize this approach to image formation is fundamentally better-suited to the diffuse scattering environments nearly universal in medical ultrasound imaging than conventional beamforming methods.

This paper is organized as follows. In Section II, we review the relevant theory of spatial covariance in medical ultrasound, and derive a mathematical framework to estimate the constituent components of the covariance matrix. Data acquisition methods are presented in Section III. Simulation, experimental and in vivo data are presented and discussed in Sections IV and V, respectively. Conclusions are presented in Section VI.

II. Theory

A. Pulse-Echo Response of Ultrasonic Imaging Systems

In scalar diffraction theory, the Huygens-Fresnel principle states that a source function can be represented as an integral over a continuum of spherical radiators. For a monochromatic, two-dimensional complex aperture function, $A(X_a, f)$, located at depth $z=0$, the one-way sensitivity pattern $P(X_s, z, f)$ is described by the Rayleigh-Sommerfeld diffraction integral[41]

$$P(X_s, z, f) = \frac{1}{j\lambda} \int\int_{-\infty}^{\infty} A(X_a, f) \frac{e^{jkr_{as}}}{r_{as}} \cos(\theta) \, dX_a \qquad (1)$$

where the coordinates of the source an aperture planes are given by $X_s = [x_s, y_s]^T$ and $X_a = [x_a, y_a]^T$, respectively. The frequency is given by f, the wavelength by $\lambda$, and the wavenumber by $$k = \frac{2\pi}{\lambda}.$$

The term $\cos(\theta)$ is the angle between the outward normal vector $\bar{n}$ and $\bar{r}_{as}$, where $\bar{r}_{as}$ is the vector from the aperture plane $(X_a, 0)$ to the source plane $(X_s, z)$ with length $r_{as}$. Assuming $r_{as}$ is much greater than the wavelength, and using the Fresnel approximation for the distance $r_{as}$, Eq. (1) can be simplified to the generalized Fresnel diffraction integral[41]:

$$P(X_s, z, f) = \frac{e^{jkz} e^{jk(X_s' X_s)/zz}}{j\lambda z} \int\int_{-\infty}^{\infty} \left\{ A(X_a, f) e^{\frac{jkX_a' X_a}{zz}} \right\} e^{\frac{-2\pi j X_s' X_a}{\lambda z}} dX_a \qquad (2)$$

where a prime represents the transpose operation. Equation (2) is recognized as the scaled Fourier transform of the product of the complex aperture function and a quadrative phase term, evaluated at spatial frequencies $$(f_x, f_y,) = \left(\frac{x_s}{\lambda s}, \frac{y_s}{\lambda s}\right).$$

The Fresnel datiaction integral reduces the spherical wavefronts in Eq. (1) to a quadratic model.

In the case of a focused transmitting aperture, Eq. (2) can be expanded as:

$$P(X_s, z, f) = \frac{e^{jkz} e^{jk(X_s' X_s)/zz}}{j\lambda z} \int\int_{-\infty}^{\infty} \left\{ A(X_a, f) e^{\frac{jkX_a' X_a}{z}(z^{-1} - z_f^{-1})} \right\} e^{\frac{-2\pi j X_s' X_a}{\lambda z}} dX_a \qquad (3)$$

in which the quadratic phase term becomes a function of both the source plane depth z and the focal depth $z_f$. When the source plane is selected as $z = z_f$, the phase term is reduced to unity. This result is characterized by the Fraunhofer diffraction integral[41]

$$P(X_s, z, f) = \frac{e^{jkz} e^{jk(X_s' X_s)/zz}}{j\lambda z} \int\int_{-\infty}^{\infty} A(X_a, f) e^{\frac{-2\pi j X_s' X_a}{\lambda z}} dX_a \qquad (4)$$

which is simply the scaled, two-dimensional Fourier transform of the aperture function, valid at the focal plane of a focused aperture, or in the far field of an unfocused aperture. Equation (4) describes a simple Fourier relationship between (1) the transmitting aperture function and the pressure distribution at the focus or, equivalently, (2) the receiving aperture function and its one-way sensitivity pattern.

B. Spatial Covariance in Medical Ultrasound

1. Theory

The van Cittert-Zernike theorem describes the spatial covariance of a propagating wavefield from an incoherence source. This is characterized by a Fourier transform relationship between an incoherent source distribution and the measured spatial covariance between points $X_1$ and $X_2$ in an observation plane, evaluated at spatial frequency $$\frac{\Delta X}{\lambda s},$$

where $\Delta X = (X_1 - X_2)$, $\lambda$ is the wavelength, and z is the distance between the source and observation planes.[4]

In pulse-echo ultrasound, backscatter from diffuse targets under coherent insonification can be considered a secondary, incoherent source, with intensity distribution equal to the squared magnitude of the product of the transmit beam amplitude (P) and the target function $(\chi)$.[23] The VCZ theorem predicts a Fourier relationship between the measured spatial covariance (R) and the source intensity distribution, given by:

$$R(\Delta X_a, z, f) = \int\int_{-\infty}^{\infty} |P(X_s, z, f) \chi(X_s, z, f)|^2 e^{\frac{-2\pi j X_s' \Delta X_a}{\lambda z}} dX_s \qquad (5)$$

where the scattering function is characterized by unresolvable, randomly distributed microstructure, with backscatter amplitude described by complex, circular Gaussian statistics.[3] Assuming $\chi$ to be spatially incoherent and statistically stationary, the autocorrelation of the scattering function at a fixed depth z is given by:[23]

$$\langle \chi(X_1,z,f)\chi^*(X_2,z,f) \rangle = \chi_0(f)\delta(X_1-X_2) \quad (6)$$

where $\delta(X)$ is a two-dimensional delta function. Under this assumption, the spatial covariance of the received echoes is proportional to the Fourier transform of the two-dimensional transmit beam intensity.

$$R(\Delta X_\alpha,z,f) \propto \mathfrak{F}\,(P(X_s,z,f)P^*(X_s,z,f)) \quad (7)$$

which is the well-known result of the VCZ theorem. At the focal plane of a focused transmitting aperture, this reduces to the scaled autocorrelation of the transmitting aperture function. For a conventional linear array with rectangular apodization, the predicted spatial covariance at the transmit focus is described by a triangle function, which linearly decreases in amplitude as element separation (or lag) increases to the full extent of the transmitting aperture.

2. Measurement

In practice, spatial covariance is estimated from discretely sampled array data. The estimated covariance of two zero-mean signals is defined as:

$$\hat{R}_{ij}[t] = x_i[t]x_j^*[t] \quad (8)$$

where $x_i[t]$ and $x_j^*[t]$ are the complex signal at time sample t, received at elements i and j, respectively, after quadrature demodulation and focusing time delays have been applied. The complex conjugate operation is given by an asterisk.

For an M-channel array, this generalizes to the outer product of the array data vector.

$$\hat{R}[t] = x[t]x^H[t] \quad (9)$$

Where $\hat{R}[t]$ is the M×M covariance matrix (with entries $\hat{R}_{ij}[t]$) at time sample t, and x[t] is the M×1 vector of complex array data at time sample t. The conjugate transpose operation is given by the superscript H.

To remove the effects of signal amplitude on the coherence estimate, the spatial covariance can also be normalized to calculate the spatial correlation. The spatial correlation of two signals $x_i[t]$ and $x_j[t]$ is represented by:

$$\hat{p}_{i,j}[t] = \frac{\hat{R}_{i,j}[t]}{\sqrt{\hat{R}_{i,i}[t]\hat{R}_{j,j}[t]}} \quad (10)$$

in which $\hat{p}_{i,j}[t]$ is the correlation coefficient of the complex signals received at elements i and j at time sample t. The M×M correlation matrix with entries $\hat{p}_{i,j}[t]$ is given by $\hat{p}[t]$.

While the covariance and correlation measurements in Eqs. (8) and (10) represent M×M matrices, measurements across all (i,j) pairs with common element separation (or lag) are often averaged to generate a one-dimensional (1-D) function, given by:

$$\hat{R}_{1-D}[t;m] = \frac{1}{M-m}\sum_{i=1,j=i+m}^{M} \hat{R}_{i,j}[t] \quad (11)$$

and $$\hat{p}_{1-D}[t;m] = \frac{1}{M-m}\sum_{i=1,j=i+m}^{M} \frac{\hat{R}_{i,j}[t]}{\sqrt{\hat{R}_{i,i}[t]\hat{R}_{j,j}[t]}} \quad (12)$$

where $\hat{R}_{1-D}$ and $\hat{p}_{1-D}$ denote the 1-D covariance and correlation, respectively, given as a function of time sample t and lag m.

C. Spatial Covariance of Piecewise-Stationary Stochastic Targets

1. Theory

Medical ultrasound systems typically operate in pulse-echo mode, such that the total system response is calculated as the product of the one-way responses on transmit and receive. For a complex target distribution $\chi(X_s,z,f)$, the received echo signal s(z,f) can be calculated by[42]

$$s(z,f) = \iint_S P_T(X_s,z,f)P_R(X_s,z,f)\chi(X_s,z,f)dX_s \quad (13)$$

where $P_T(X_s,z,f)$ is defined as transmit pressure distribution, and $P_R(X_s,z,f)$ is defined as one-way receive system response, calculated using Eq. (2). The imaging frequency is given by f and depth by z. The integration surface S is defined as the plane orthogonal to the transducer axis at depth z. Equation (13) provides a means to calculate the received echo signal given arbitrary aperture and scattering functions.

The following analysis considers the monochromatic case at an arbitrary depth z, and is not limited to the focal region of the transducer. For simplicity, the frequency (f) and depth (z) have been removed from the notation, such that s=s(z,f), $P(X_s)=P(X_s,z,f)$, and $\chi(X_s)=\chi(X_s,z,f)$.

From Eq. (13), the echo signal received at a single element i can be calculated as $$s_i = \iint_S P_T(X_s)P_{R_i}(X_s)\chi(X_s)dX_s \quad (14)$$

where $s_i$ is the complex pulse echo signal received at element i, and $P_{R_i}$ is the one-way receive system response at element i.

We consider the case where the total system output at element i is composed of both the complex pulse echo signal ($s_i$) and additive noise ($n_i$), such that $x_i = s_i + n_i$. The covariance of the received signals at elements i and j is then given by $$R_{ij} = \langle x_i x_j^* \rangle = \langle (s_i+n_i)(s_j+n_j)^* \rangle \quad (15)$$

where $\langle \cdot \rangle$ is the expected value operator. Assuming the signal and noise are uncorrelated, Eq. (15) can be expanded as:

$$R_{ij} = \langle s_i s_j^* \rangle + \langle n_i n_j^* \rangle \quad (16)$$

We then define the signal and noise covariance terms as:

$$A_{ij} = \langle s_i s_j^* \rangle \quad (17)$$

and $$N_{ij} = \langle n_i n_j^* \rangle \quad (18)$$

respectively, such as the expected covariance is given by:

$$R_{ij} = A_{ij} + N_{ij} \quad (19)$$

We first consider the covariance of the pulse-echo signal. Substituting Eq. (14) into Eq. (17), this is given by $$A_{ij} = \langle \iint_S P_T(X_1)P_{R_i}(X_1)\chi(X_1)dX_1 \iint_S P_T^*(X_2)P_{R_j}^{-1}(X_2)\chi^1(X_s)dX_2 \rangle \quad (20)$$

Rearranging the order of integration and expected value yields:

$$A_{ij} = \iint_S \iint_S P_T(X_1)P_{R_i}(X_1)P_T^1(X_2)P_{R_j}^1(X_2)\langle \chi(X_1)\chi^*(X_2) \rangle dX_1 dX_2 \quad (21)$$

The autocorrelation of an incoherent scattering function with stationary statistics is given by Eq. (6). Here, we relax the assumption of stationarity to a piecewise-stationary model, and allow the scattering strength to vary as a function of absolute position, such that the autocorrelation of the target function is given by:[73]

$$\langle \chi(X_1)\chi^*(X_2)\rangle = \chi_0(X_1)\chi_0(X_2)\delta(X_1-X_2) \quad (22)$$

where $\chi_0(X)$ is the spatially-varying scattering strength of the target region. Substituting Eq. (22) into Eq. (21), the covariance is given by:

$$A_{ij}=\iint_S \int_S P_T(X_1)P_{R_i}(X_1)P_T^1(X_2)P_{R_j}^1(X_2)\chi_0(X_1)\chi_0(X_2)\delta(X_1-X_2)dX_1dX_2 \quad (23)$$

Using the sifting property of the delta function, one of the ranges of integration can be eliminated to yield:

$$A_{ij}=\iint_S P_T(X_1)P_{R_i}(X_1)P_T^1(X_2)P_{R_j}^1(X_2)\chi_0^2(X_s)dX_s \quad (24)$$

The integration region S can then be broken up into K separate spatial regions $S_k$. Under the piecewise-stationary definition of the target function, we assume the scattering strength $\chi_O^2(X_s)$ to be constant across each region $S_k$. Equation (24) can then be represented by a summation over K spatial regions.

$$A_{ij}=\Sigma_{k=1}^K \iint_{S_k} P_T(X_1)P_{R_i}(X_1)P_T^1(X_2)P_{R_j}^1(X_2)\chi_{0,k}^2 dX_s \quad (25)$$

where the constant value of $\chi_0(X_s)$ in region $S_k$ is given by $\chi_{0,k}^2$, which represents the variance in region $S_k$. The $\chi_{0,k}^2$ term can be pulled out of the integral:

$$A_{ij}=\Sigma_{k=1}^K \chi_{0,k}^2 \iint_{S_k} P_T(X_1)P_{R_i}(X_1)P_T^1(X_2)P_{R_j}^1(X_2)dX_s \quad (26)$$

We then define the covariance of echoes from region $S_k$ received at elements i and j as:

$$A_{ij}^{(k)}=\iint_{S_k} P_T(X_1)P_{R_i}(X_1)P_T^1(X_2)P_{R_j}^1(X_2)dX_s \quad (27)$$

such that the Eq. (26) can be represented as:

$$A_{ij}=\Sigma_{k=1}^K \chi_{0,k}^2 A_{ij}^{(k)} \quad (28)$$

Equation (28) implies that the covariance of the complex signals received at channels i and j can be expressed as a weighted superposition of constituent covariance components $A_{ij}^{(k)}$ from K spatially independent regions $S_k$.

Figure 16A:
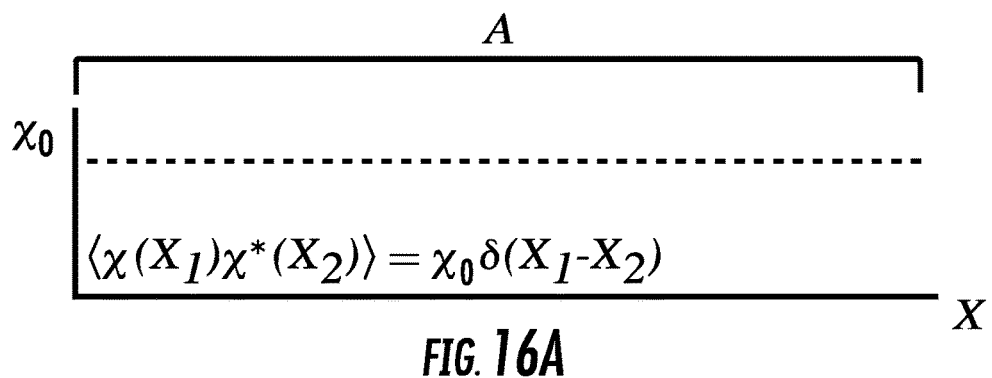
FIGS. 16A-16B are graphs illustrating a 3-parameter model of a spatially incoherent, stationary scattering target (FIG. 16A) and a piecewise-stationary scattering target (FIG. 16B).
Figure 16B:
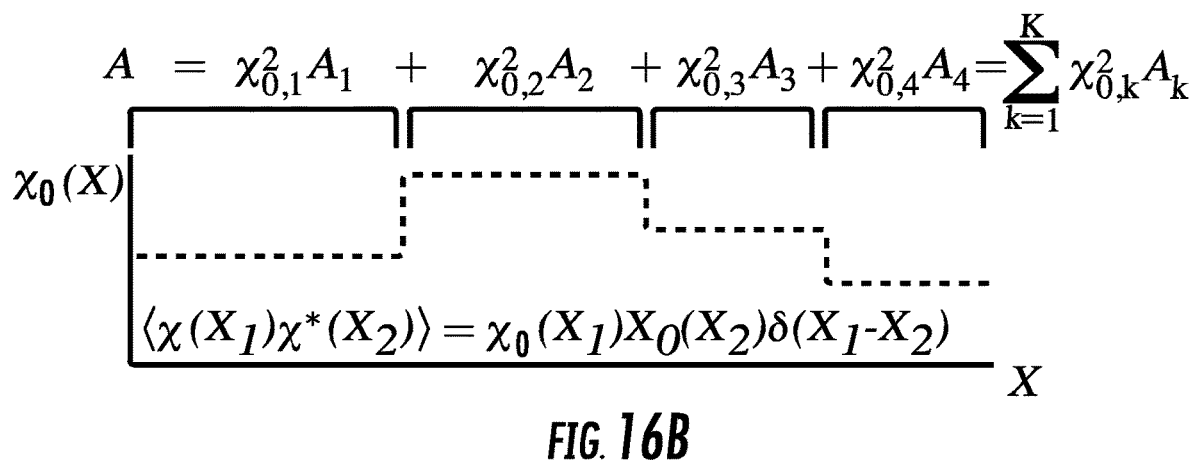

Defining the full pulse echo data vector as $s=[s_1, s_2, \ldots, s_M]^T$, and $s_k$ as the subset of echoes from region $S_k$, it can be shown that Eq. (28) generalizes to the full covariance matrix $A=\langle ss^H\rangle$ $$A=\Sigma_{k=1}^K \chi_{0,k}^2 A_k \quad (29)$$

where $A=\langle s_k s_k^H\rangle$ is the M×M covariance matrix of echoes from spatial region $S_k$. The full pulse echo data covariance A is the superposition of K echo covariance matrices $A_k$, weighted by variances $\chi_{0,k}^2$. This result, and the relationship to the scattering target models of Eqs (6) and (22) are shown in FIGS. 16A-16B.

We now consider the covariance of the noise term. Assuming L uncorrelated sources of additive noise, Eq. (18) can be similarly represented by a superposition of covariances, $$N=\Sigma_{l=1}^L \beta_l^2 N_l \quad (30)$$

where $N=\langle n_l n_l^H\rangle$ is the M×M covariance matrix of additive noise source $n_1$, and N is the superposition of L additive noise covariance matrices $N_1$, weighted by variances $\beta_l^2$. Example additive noise sources may include thermal noise and superimposed wavefronts due to multipath or off-axis scattering.

Based on the spatial decompositions of Eqs. (29) and (30), we consider the M×1 vector of receive aperture data x as a weighted superposition of pulse-echo signal vectors $s_k$ and additive noise vectors $n_1$, given by:

$$x=\Sigma_{k=1}^K \chi_{0,k} s_k + \Sigma_{l=1}^L \beta_l n_l \quad (31)$$

The M×M covariance matrix is given by $$R=\langle xx^H\rangle \quad (32)$$

Substituting (31) into (32), the covariance is given by:

$$R=\langle (\Sigma_{k=1}^K \chi_{0,k} s_k + \Sigma_{l=1}^L \beta_l n_l)(\Sigma_{k=1}^K \chi_{0,k} s_k + \Sigma_{l=1}^L \beta_l n_l)^H\rangle \quad (33)$$

Assuming the pulse echo signal $s_k$ and noise $n_l$ are uncorrelated, the cross terms vanish, yielding the generalized from of Eq. (19) [via Eqs. (29) and (30)].

$$R=\langle \Sigma_{k=1}^K \chi_{0,k}^2 s_k s_k^H\rangle + \langle \Sigma_{l=1}^L \beta_l^2 n_l n_l^H\rangle \quad (34a)$$

$$R=\Sigma_{k=1}^K \chi_{O,k}^2 A_k + \Sigma_{l=1}^L \beta_l^2 N_l \quad (34b)$$

$$R=A+N \quad (34c)$$

By combining terms, Eq. (34) can be represented as the superposition of P spatial and additive noise covariances. This result is given by[73]:

$$R=\Sigma_{p=1}^P \alpha_p^2 R_p \quad (35)$$

where $R_p$, is the set of all $A_k$ and $N_l$, $\alpha_p^2$ is the set of all $\chi_{0,k}^2$ and $\beta_l^2$, and P=K+L. Equation (35) implies the measured covariance matrix R can be represented as the superposition of P constitutive covariances $R_p$ of echo data from K spatial regions $S_k$ and L additive noise components.

2. Example Application: Medical Ultrasound

Figure 17A:
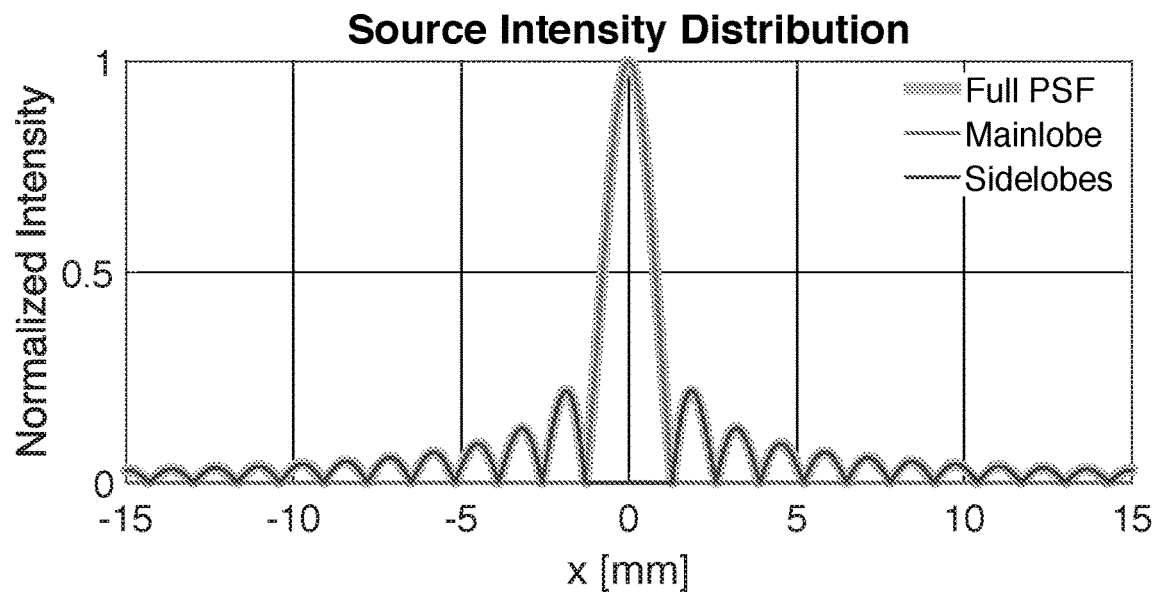
FIG. 17A is a graph of the source intensity.
Figure 17B:
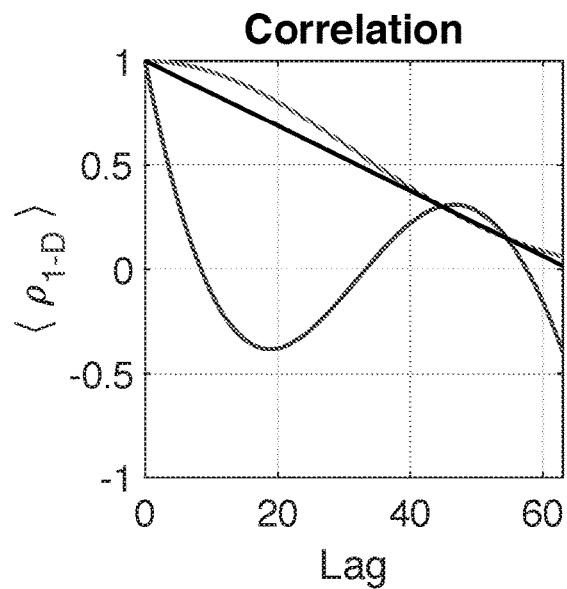
FIG. 17B is a graph of the correlation.
Figure 17C:
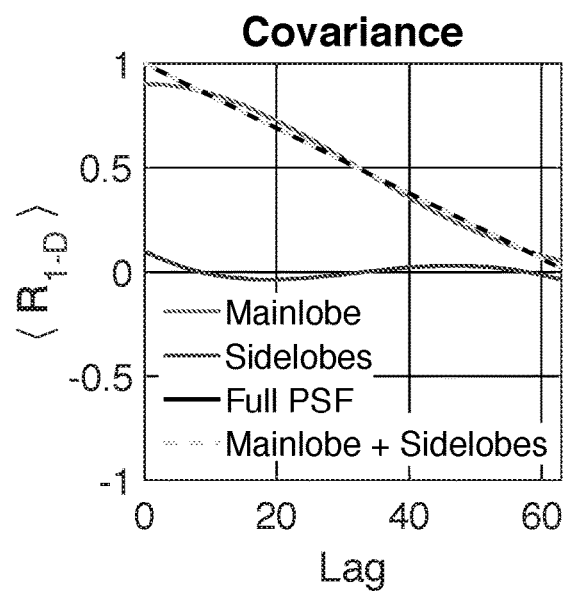
FIG. 17C is a graph of the covariance curves predicted at the focus for a narrowband array with rectangular transmit apodization.

In medical ultrasound, the total spatial region S is given by the transmit intensity distribution. Restricting the analysis to the one-dimensional case, a simple theoretical example is presented in FIGS. 17A-17B. FIG. 17A is a graph of the source intensity, FIG. 17B is a graph of the correlation, and FIG. 17C is a graph of the covariance curves predicted at the focus for a narrowband array with rectangular transmit apodization.

The transmit intensity distribution for a 3 MHz, 1.92 cm, 64-element linear array with rectangular apodization is shown at the top. Assuming a uniform, diffuse target, this is given by a sinc² function at the focus.

If the source distribution is then segmented into two components—chosen here as the mainlobe and sidelobe regions, respectively, delimited by the first zero crossing of the sinc² function—the predicted covariance and correlation from each distinct region can be determined numerically. These results are plotted at the bottom of FIG. 17, in which the covariances have been normalized to the maximum value of the covariance of the full point spread function (PSF) curve. The mainlobe and sidelobe components show distinct curves, which superimpose in the covariance domain to recover the triangle function from the full sinc² intensity distribution.

These results are validated in Ref. 73 across imaging depths, transmit apodizations, and in the presence of random noise using simulated ultrasonic echo data.

D. Estimation of the Constitutive Components

The estimated data covariance matrix from an M-channel array at time sample t is given by:

$$\hat{R}[t]=x[t]x^H[t] \quad (36)$$

where $\hat{R}[t]$ represents the M×M covariance matrix and x[t] is the M×1 vector of complex, time-delayed array data. The conjugate transpose operation is given by $(^H)$. In practice, the covariance matrix R is difficult to estimate from a point measurement at a single depth. Spatial averaging can be used to improve the conditioning of the estimate, given by:

$$\hat{R}[t] = \frac{1}{T} \sum_{\tau=-T/2}^{T/2} x[t+\tau] x^H[t+\tau] \tag{37}$$

where T is a small axial window, or kernel, over which $\hat{R}$ is averaged, typically on the order of a wavelength. The following derivation refers to a covariance estimate at a single sample. Accordingly, the sample index t has been removed for simplicity in notation, such that $\hat{R}=\hat{R}[t]$.

Consistent with Eq. (35), we consider the true data covariance matrix R to be a combination of constituent covariance models, denoted here by $A_i$, weighted by scalar variances $\alpha_i^2$:

$$R = \Sigma_{i=1}^{P} \alpha_i^2 A_i + N \tag{38}$$

Where N is a noise matrix to model the uncertainty in the observation. R, $A_i$, and IV are of shape M×M. The number of constituent models is given by P. The covariance R and the model matrices $A_i$ are assumed Hermitian symmetric.

A loss function is defined to minimize the squared error over the variances $\alpha_i^2$:

$$\epsilon = \|\hat{R} - \Sigma_{i=1}^{P} \alpha_i^2 A_i\|_F^2 \tag{39}$$

Where the Frobenius norm is represented by $(_F)$. Additionally, let $\alpha^2$ be the P×1 vector of variances:

$$\alpha^2 = [\alpha_1^2 \alpha_2^2, \ldots \alpha_P^2]^T \tag{40}$$

The least squares estimator is then defined as:

$$\hat{\alpha}_{ls}^2 = \arg\min_{\alpha^2} \|\hat{R} - \Sigma_{i=1}^{P} \alpha_i^2 A_i\|_F^2 \tag{41}$$

The variance estimates are then calculated as the $\alpha^2$ vector for which the gradient of the loss function is equal to zero ($\nabla_{\alpha^2}\epsilon = 0$). A brief derivation is presented below.

The loss function is first expanded using the definition of the Frobenius norm:[69-71]

$$\epsilon = Tr[(\hat{R} - \Sigma_{i=1}^{P} \alpha_i^2 A_i)^H (\hat{R} - \Sigma_{j=1}^{P} \alpha_j^2 A_j)] \tag{42}$$

where Tr is the trace operator and the conjugate transpose operation is represented by $(^H)$. The inner terms can be expanded as:

$$\epsilon = Tr[\hat{R}^H \hat{R} - \hat{R}^H (\Sigma_{j=1}^{P} \alpha_j^2 A_j) - (\Sigma_{i=1}^{P} \alpha_i^2 A_i^H) \hat{R} + (\Sigma_{i=1}^{P} \alpha_i^2 A_i^H)(\Sigma_{j=1}^{P} \alpha_j^2 A_j)] \tag{43}$$

Given $Tr[A+B] = Tr[A] + Tr[B]$, and $Tr[\alpha^2 A] = \alpha^2 Tr[A]$ [24], and rearranging the order of summation, Eq. (43) can be represented as:

$$\epsilon = Tr[\hat{R}^H \hat{R}] - \Sigma_{j=1}^{P} \alpha_j^2 Tr[\hat{R}_H A_j] - \Sigma_{i=1}^{P} \alpha_i^2 Tr[A_i^H \hat{R}] + \Sigma_{i=1}^{P} \alpha_i^2 \alpha_j^2 Tr[A_i^H A_j] \tag{44}$$

Assuming Hermitian symmetry of and $\hat{R}$ and $A_i$, $Tr[\hat{R}^H A_i] = Tr[A_i^H \hat{R}]$ can be used to reduce Eq. (44) to:

$$\epsilon = Tr[\hat{R}^H \hat{R}] - 2\Sigma_{i=1}^{P} \alpha_i^2 Tr[A_i^H \hat{R}] + \Sigma_{i=1}^{P} \Sigma_{j=1}^{P} \alpha_i^2 \alpha_j^2 Tr[A_i^H A_j] \tag{45}$$

Taking the derivative with respect to the individual weight $\alpha_k^2$:

$$\frac{\partial \epsilon}{\partial \alpha_k^2} = -2Tr[A_k^H \hat{R}] + \sum_{j=1}^{P} \alpha_j^2 Tr[A_k^H A_j] + \sum_{i=1}^{P} \alpha_i^2 Tr[A_i^H A_k] \tag{46}$$

Given the Hermitian symmetry of $A_i$, $Tr[A_i^H A_k] = Tr[A_k^H A_i]$ can be used to yield:

$$\frac{\partial \epsilon}{\partial \alpha_k^2} = -2Tr[A_k^H \hat{R}] + \alpha_i^2 Tr[A_i^H A_k] \tag{47}$$

Setting Eq. (47) equal to zero:

$$0 = -Tr[A_k^H \hat{R}] + \Sigma_{i=1}^{P} \alpha_i^2 Tr[A_i^H A_k] \tag{48}$$

The derivative can then be generalized with respect to the P×1 vector of component weights $\alpha^2$, such that:

$$\nabla_{\alpha^2} \epsilon = \left[ \frac{\partial \epsilon}{\partial \alpha_1^2}, \frac{\partial \epsilon}{\partial \alpha_2^2}, \ldots, \frac{\partial \epsilon}{\partial \alpha_P^2} \right]^T \tag{49}$$

where $\nabla_{\alpha^2}$ represents the gradient with respect to the unknown parameter vector $\alpha^2$. Letting X be the P×P Hermitian symmetric matrix of $Tr[A_i^H A_k]$, $$X = \begin{bmatrix} Tr[A_1^H A_1] & Tr[A_1^H A_2] & \cdots & Tr[A_1^H A_P] \\ Tr[A_2^H A_1] & Tr[A_2^H A_2] & \cdots & Tr[A_2^H A_P] \\ \vdots & \vdots & \ddots & \vdots \\ Tr[A_P^H A_1] & Tr[A_P^H A_2] & \cdots & Tr[A_P^H A_P] \end{bmatrix} \tag{50}$$

and Y be the P×1 vector $Tr[A_i^H \hat{R}]$ $$Y = \begin{bmatrix} Tr[A_1^H \hat{R}] \\ Tr[A_2^H \hat{R}] \\ \vdots \\ Tr[A_P^H \hat{R}] \end{bmatrix} \tag{51}$$

the generalized version of Eq. (47) is given by:

$$\nabla_{\alpha^2} \epsilon = -2Y + 2X\alpha^2 \tag{52}$$

Setting Eq (52) equal to zero, the weights of the constitutive components can be estimated as:

$$\hat{\alpha}_{ls}^2 = \sqrt{X^{-1}Y} \tag{53}$$

Where $\hat{\alpha}_{ls}^2$ defines the magnitude estimates of the contribution of each covariance constituent $A_i$ for each pixel in the image.

E. Application to Imaging

1. Selection of Constituent Covariance Models

From Eq. (35), the source intensity distribution can be segmented into a number of spatial regions of interest which contribute distinct components to the estimated covariance matrix. While these spatial regions can be chosen arbitrarily, for the purposes of imaging, an intuitive choice of spatial regions corresponds to the mainlobe and sidelobes of the predicted narrowband point spread function.

Additionally, a noise covariance model can also be defined. Acoustic clutter due to electronic noise and reverberation has been shown to be largely incoherent, with a coherence function well-approximated by delta-function at lag zero[30,31,45], or an identity matrix in the covariance domain. Given this noise model, a third constitutive covariance component corresponding to an identity matrix can be incorporated into the estimator formulation.

The mainlobe and sidelobe formulations, with and without the incoherent noise, are referred to as the 2- and 3-parameter MIST models, respectively. The 3-parameter model is shown in FIGS. 16A-16B. In particular, FIG. 16A illustrates a spatially incoherent, atationary scattering target with constant scattering variance. The covariance A incorporates echoes from the entire target region, consistent with the scattering target model.[23] FIG. 16B illustrates a piecewise-stationary scattered target. The covariance A represents a weighted superposition of covariances from each locally homogeneous component of the target region.

2. Image Formation

The variance estimates of Eq. (53) can yield negative values of $\hat{\alpha}_{ls}^2$ which have no physical meaning, as variances are necessarily positive. In practice, a non-negative least squares optimization is performed to calculate the weights, given by[72]:

$$\hat{\alpha}_{ls}^2 = arg\ min_{\alpha^2} \|X\alpha^2 - Y\|_F^2 \text{ subject to } \alpha^2 \geq O. \quad (54)$$

Additionally, X is generally assumed invertible, which is determined by the orthogonality of the model matrices $A_i$. While the constituent covariance matrices presented in FIGS. 16A-16B are sufficiently separable, other covariance models may require diagonal loading the improve the matrix conditioning.

The variance estimates $\hat{\alpha}_{ls}^2 = \hat{\alpha}_{ls}^2(x,z)$ are calculated for each pixel location in the image, where x and z are the azimuthal and axial coordinates, respectively. The value of each pixel is calculated from a single model of interest, typically the mainlobe covariance estimate. The pixel value is given by: $|\alpha_i(x,z)| = \sqrt{\alpha_i^2(x,z)}$, where i is the index of the desired constituent component, and the square root gives an estimate of magnitude. The spatial map of magnitude estimates is logarithmically compressed before display.

Figure 18A:
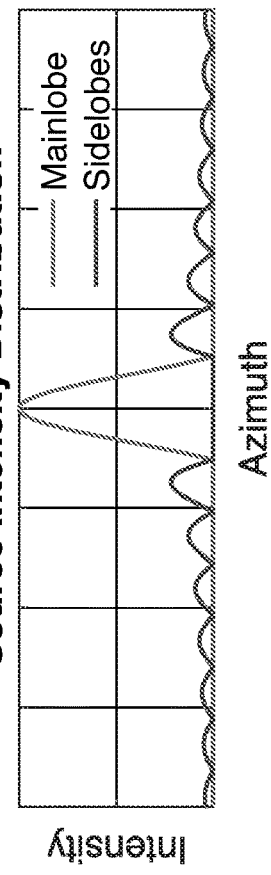
FIGS. 18A-18C are graphs illustrating an estimator framework using three constituent models, including the source intensity distribution (FIG. 18A), the constituent covariance components (FIG. 18B) and the covariance (FIG. 18C).
Figure 18B:
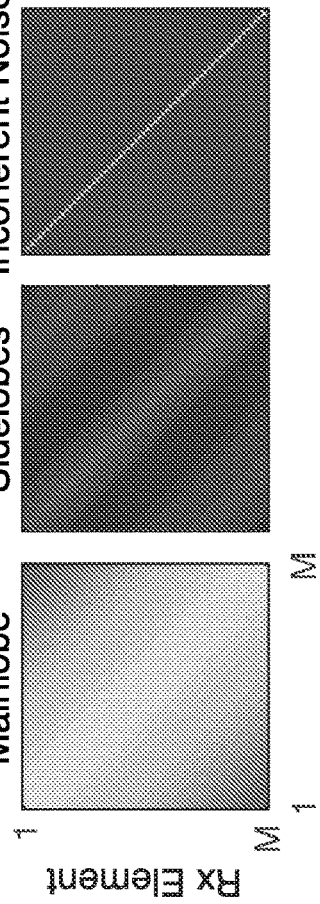
Figure 18C:
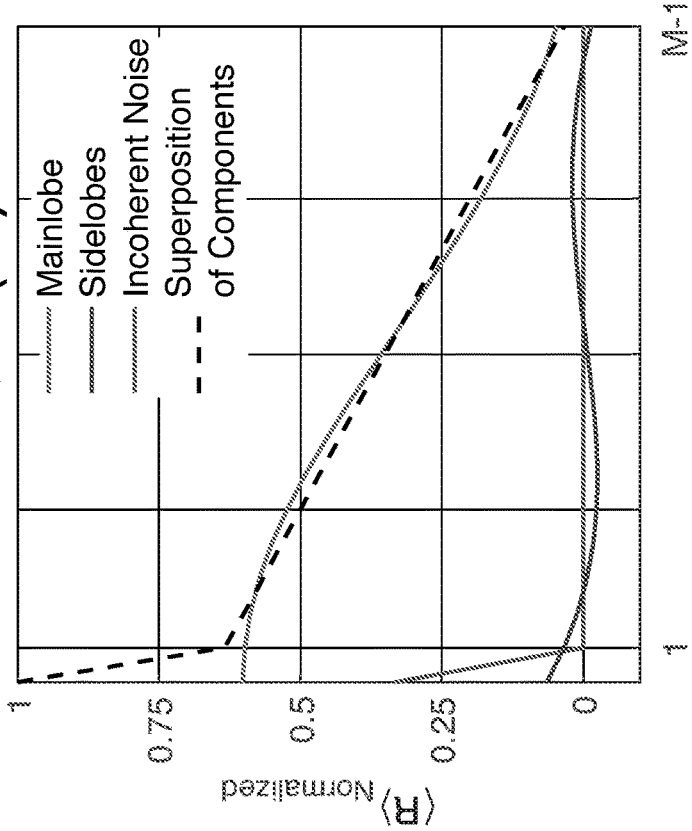

FIGS. 18A-18C are graphs illustrating an estimator framework using three constituent models, including the source intensity distribution (FIG. 18A), the constituent covariance components (FIG. 18B) and the covariance (FIG. 18C). The predicted intensity distribution for a narrowband array is segmented into distinct mainlobe and sidelobe spatial regions. A third covariance model corresponding to incoherent noise is represented by an identity matrix. The mainlobe, sidelobe, and incoherent noise covariance matrices are plotted at bottom, and a 1-D plot showing the average along the diagonal of each matrix is shown at right, with the superposition of the three components plotted in the dashed line.

FIGS. 19A-19H are images and graphs generated by a MIST estimator of simulated targets according to some embodiments. FIGS. 19A-19C illustrate a conventional B-mode image (FIG. 19A) as compared to the mainlobe estimate (FIG. 19B) and sidelobe estimate (FIG. 19C) for a point, and FIGS. 19E-19G illustrate a conventional B-mode image (FIG. 19E) as compared to the mainlobe estimate (FIG. 19F) and sidelobe estimate (FIG. 19G) for of anechoic cyst target. FIGS. 19D and 1911 are graphs of 1-D lateral profiles at 50 mm depth for a point (FIG. 19D) and an anechoic cyst target (FIG. 19H), where the y-axis has been split to display the full range of the lateral profiles.

Figures 20A, 20B, 20C, 20D:
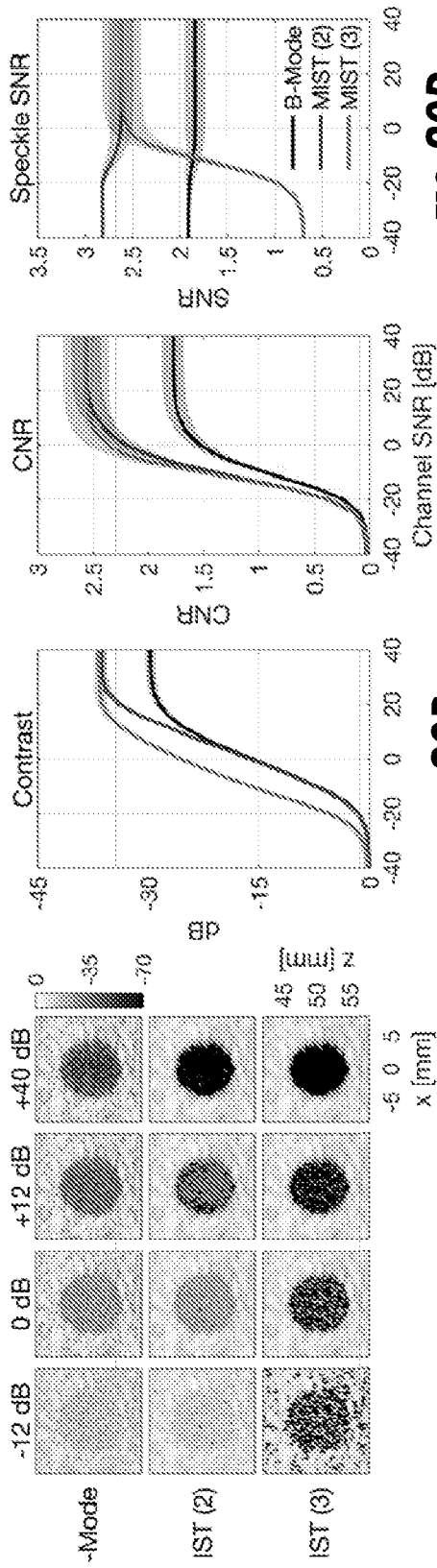
FIG. 20A is a series of images for a B-Mode image (top row) compared to the 2-parameter (mainlobe+sidelobe) (middle row) and 3-parameter (mainlobe+sidelobe+incoherent noise) (bottom row) MIST model across a range of channel signal-to-noise ratios for a 1 cm anechoic target for sample images at selected SNRs.
FIGS. 20B-20D are graphs of the Contrast (FIG. 20B), CNR (FIG. 20C), and speckle SNR (FIG. 20D), which are plotted against channel SNR.

FIG. 20A is a series of images for a B-Mode image (top row) compared to the 2-parameter (mainlobe+sidelobe) (middle row) and 3-parameter (mainlobe+sidelobe+incoherent noise) (bottom row) MIST model across a range of channel signal-to-noise ratios for a 1 cm anechoic target for sample images at selected SNRs. FIGS. 20B-20D are graphs of the Contrast (FIG. 20B), CNR (FIG. 20C), and speckle SNR (FIG. 20D), which are plotted against channel SNR.

Figure 21A:
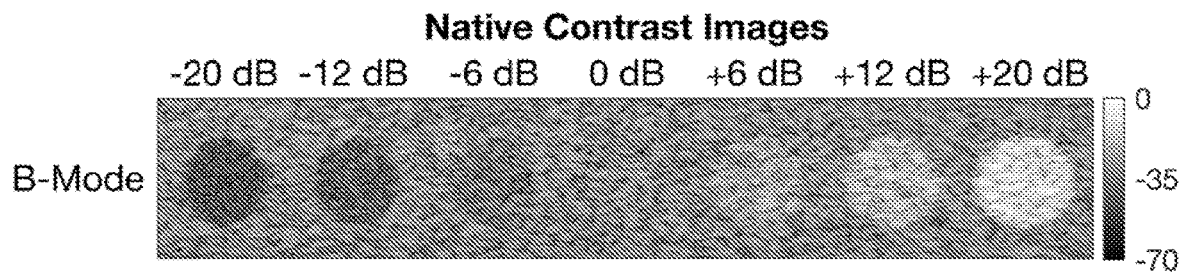
FIGS. 21A-21B illustrate a comparison of B-mode (FIG. 21A) and MIST (FIG. 21B) images across targets of varying native contrast at a channel SNR of 0 dB.
Figure 21B:
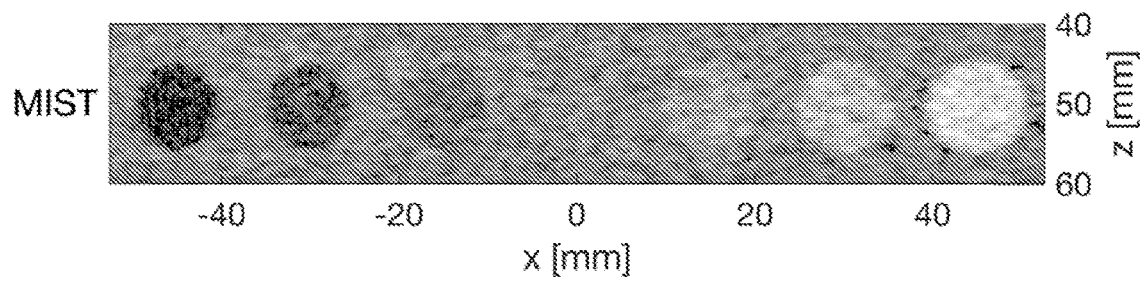
Figure 21C:
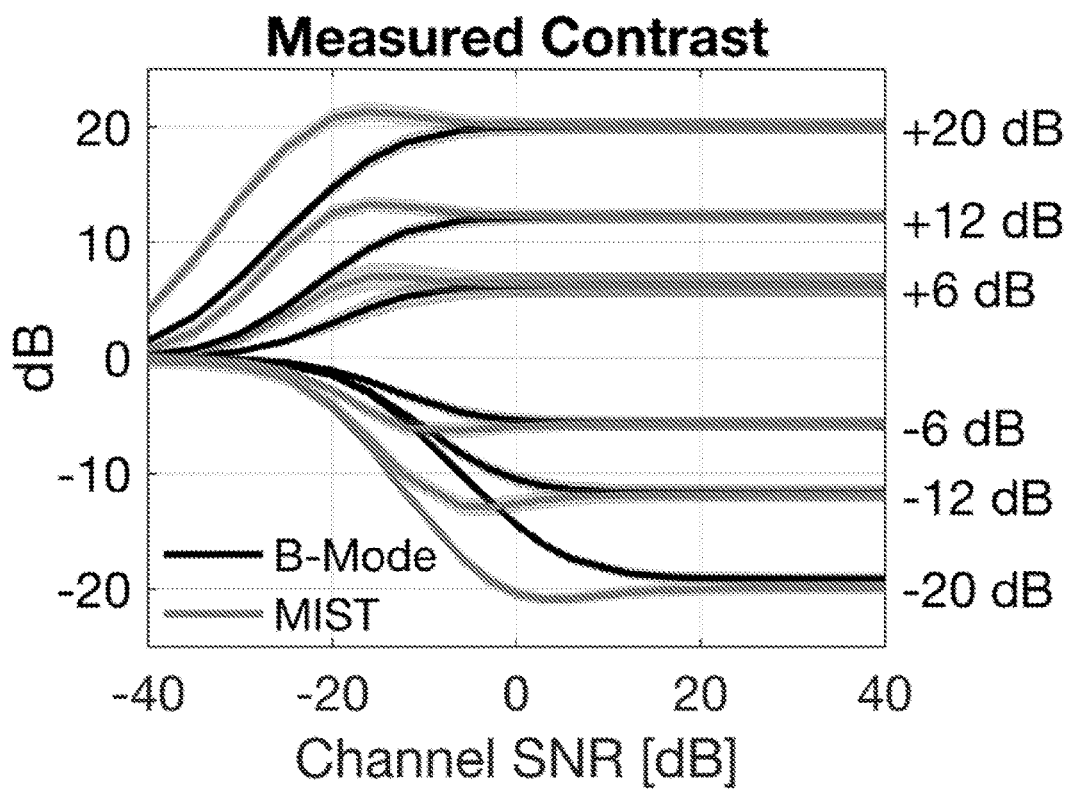
FIG. 21C is a plot of measured contrast vs. channel SNR to demonstrate the stability of MIST across SNR.

FIGS. 21A-21B illustrate a comparison of B-mode (FIG. 21A) and MIST (FIG. 21B) images across targets of varying native contrast at a channel SNR of 0 dB. FIG. 21C is a plot of measured contrast vs. channel SNR demonstrate the stability of MIST across SNR. Across native contrast targets, MIST attains the true target contrast at a lower SNR than B-Mode.

FIGS. 22A-22B are sample images of the edge phantom with a speckle generating and an anechoic region ($-\infty$dB contrast). FIG. 22C is a graph of averaged lateral profiles of B-Mode and MIST images for each set of phantom simulations. The native contrast of the imaging phantom is indicated by the axis on the right.

Figure 23A:
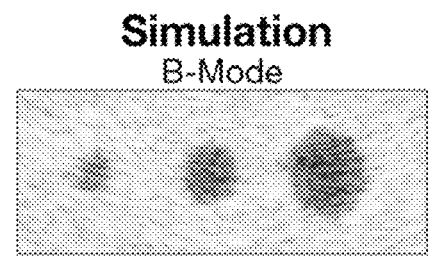
Figure 23D:
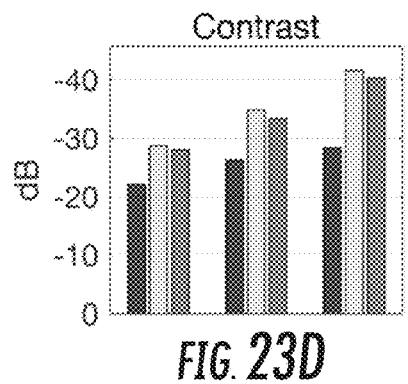
FIG. 23D is a graph of the contrast for the simulation.
Figure 23I:
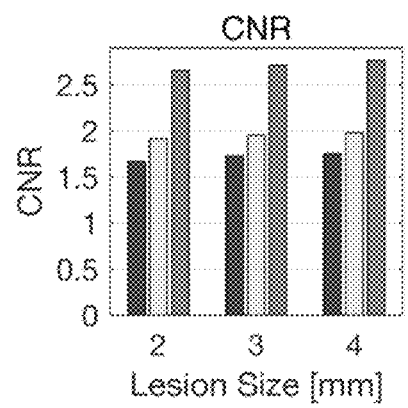
FIG. 23I is a graph of the contrast for the phantom.
Figure 23J:
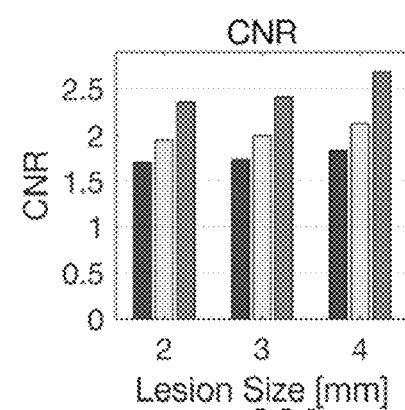
FIG. 23J is the CNR graph for the phantom plotted to compare performance for each lesion.

FIGS. 23A-23C and FIGS. 23F-2311 are images of approximately matched B-Mode images (FIGS. 23A and 23F) and MIST images using a single sample (0λ) (FIGS. 23B and 23G) and axial averaging of the covariance matrix over a wavelength (1λ) (FIGS. 23c and 23H). FIGS. 23A-23C are simulation images and FIGS. 23F-23H are phantom images. FIG. 23D is a graph of the contrast for the simulation, FIG. 23E is the CNR graph for the simulation, FIG. 231 is a graph of the contrast for the phantom, and FIG. 23E is the CNR graph for the phantom plotted to compare performance for each lesion.

FIGS. 24A-23D are in vivo liver images comparing B-Mode (FIG. 24A), receive spatial compounding (3 apertures, 50% overlap) (FIG. 24B), SLSC (Q=5%, 1λ kernel) (FIG. 24C), and MIST (1λ) (FIG. 24D). B-Mode, receive spatial compounding, and MIST images are shown on a 70 dB dynamic range. SLSC is shown on a [0-1] scale.

FIGS. 25A-25D are in vivo fetal images comparing B-mode (FIG. 25A), receive spatial compounding (3 apertures, 50% overlap) (FIG. 25B), SLSC (Q=5%, 1λ kernel) (FIG. 25C), and MIST (1λ) (FIG. 25D). B-Mode, receive spatial compounding, and MIST images are shown on a 60 dB dynamic range. SLSC is shown on a [0-1] scale.

The foregoing is illustrative of the present invention and is not to be construed as limiting thereof. Although a few example embodiments of this invention have been described, those skilled in the art will readily appreciate that many modifications are possible in the example embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

REFERENCES

[1] A. Papoulis and S. U. Pillai, Probability, Random Variables, and Stochastic Processes (Tata McGraw-Hill Education, N.Y., 2002).

[2] J. W. Goodman, "Statistical properties of laser speckle patterns," in Laser Speckle and Related Phenomena (Springer, Berlin, 1975), pp. 9-75.

[3] R. F. Wagner, S. W. Smith, J. M. Sandrik, and H. Lopez, "Statistics of speckle in ultrasound b-scans," IEEE Trans. Son. Ultrason. 30(3), 156-163 (1983).

[4] J. W. Goodman, Statistical Optics (Wiley, New York, 2015).

[5] J. W. Goodman, "Role of coherence concepts in the study of speckle," Proc. SPIE 194, 86-94 (1979).

[6] P. Beckmann and A. Spizzichino, The Scattering of Electromagnetic Waves from Rough Surfaces (Pergamon Press, New York, 1963).

[7] R. F. Wagner, M. F. Insana, and D. G. Brown, "Unified approach to the detection and classification of speckle texture in diagnostic ultrasound," Opt. Eng. 25(6), 738-742 (1986).

[8] M. F. Insana, R. F. Wagner, B. S. Garra, D. G. Brown, and T. H. Shawker, "Analysis of ultrasound image texture via generalized Rician statistics," Opt. Eng. 25(6), 743-748 (1986).

[9] J. Dainty, "Some statistical properties of random speckle patterns in coher-ent and partially coherent illumination," Opt. Acta: Int. J. Opt. 17(10), 761-772 (1970).

[10] C. B. Burckhardt, "Speckle in ultrasound b-mode scans," IEEE Trans. Son. Ultrason. 25(1), 1-6 (1978).

[11] E. Verdet, "Étude sur la constitution de la lumiere non polarisée et de la lumiere partiellement polarisée" ("Study on the constitution of non polarized and polarized light"), Ann. Sci. Éc. Norm. Supér. 2,291-316 (1865).

[12] L. Rayleigh, "XII. On the resultant of a large number of vibrations of the same pitch and of arbitrary phase," London Edinburgh Dublin Philos. Mag. J. Sci. 10(60), 73-78 (1880).

[13] J. D. Rigden and E. I. Gordon, "The granularity of scattered optical maser light," Proc. I.R.E. 50,2367 (1962).

[14] B. Oliver, "Sparkling spots and random diffraction," Proc. IEEE 51(1), 220-221 (1963).

[15] J. W. Goodman, "Statistical properties of laser sparkle patterns," TR-2303-1, Stanford University Electronics Labs (1963).

[16] L. I. Goldfischer, "Autocorrelation function and power spectral density of laser-produced speckle patterns," J. Opt. Soc. A 55(3), 247-253 (1965).

[17] W. Martienssen and S. Spiller, "Holographic reconstruction without gran-ulation," Phys. Lett. A 24(2), 126-128 (1967).

[18] J. Dainty, "The statistics of speckle patterns," in Progress in Optics (Elsevier, Amsterdam, 1977), Vol. 14, pp. 1-46.

[19] J. C. Dainty, "An introduction to Gaussian speckle," Proc. SPIE 243,2-8 (1980).

[20] P. Van Cittert, "Kohaerenz-problems" ("Coherence problems"), Physica 6(7-12), 1129-1138 (1939).

[21] F. Zernike, "Diffraction and optical image formation," Proc. Phys. Soc. 61(2), 158 (1948).

[22] L. Mandel and E. Wolf, Optical Coherence and Quantum Optics (Cambridge University Press, Cambridge, 1995).

[23] R. Mallart and M. Fink, "The van Cittert-Zernike theorem in pulse echo measurements," J. Acoust. Soc. Am. 90(5), 2718-2727 (1991).

[24] R. F. Wagner, M. F. Insana, and S. W. Smith, "Fundamental correlation lengths of coherent speckle in medical ultrasonic images," IEEE Trans. Ultrason. Ferroelectr. Freq. Control 35(1), 34-44 (1988).

[25] R. Mallart and M. Fink, "Adaptive focusing in scattering media through sound-speed inhomogeneities: The van Cittert Zernike approach and focusing criterion," J. Acoust. Soc. Am. 96(6), 3721-3732 (1994).

[26] K. Hollman, K. Rigby, and M. O'Donnell, "Coherence factor of speckle from a multi-row probe," in IEEE Ultrasonics Symposium (1999), Vol. 2, pp. 1257-1260.

[27] J. C. Bamber, R. A. Mucci, and D. P. Orofino, "Spatial coherence and beamformer gain," in Acoustical Imaging (Springer, Berlin, 2002), pp. 43-48.

[28] J. C. Bamber, R. A. Mucci, D. P. Orofino, and K. Thiele, "B-mode speckle texture: The effect of spatial coherence," in Acoustical Imaging (Springer, Berlin, 2002), pp. 141-146.

[29] G. F. Pinton, G. E. Trahey, and J. J. Dahl, "Sources of image degradation in fundamental and harmonic ultrasound imaging using nonlinear, full-wave simulations," IEEE Trans. Ultrason. Ferroelectr. Freq. Control 58(4), 754-765 (2011).

[30] G. F. Pinton, G. E. Trahey, and J. J. Dahl, "Spatial coherence in human tissue: Implications for imaging and measurement," IEEE Trans. Ultrason. Ferroelectr. Freq. Control 61(12), 1976-1987 (2014).

[31] W. Long, N. Bottenus, and G. E. Trahey, "Lag-one coherence as a metric for ultrasonic image quality," IEEE Trans. Ultrason. Ferroelectr. Freq. Control 65(10), 1768-1780 (2018).

[32] G. E. Trahey, S. Smith, and O. Von Ramm, "Speckle pattern correlation with lateral aperture translation: Experimental results and implications for spatial compounding," IEEE Trans. Ultrason. Ferroelectr. Freq. Control 33(3), 257-264 (1986).

[33] M. O'Donnell and S. D. Silverstein, "Optimum displacement for com-pound image generation in medical ultrasound," IEEE Trans. Ultrason. Ferroelectr. Freq. Control 35(4), 470-476 (1988).

[34] P.-C. Li and M.-L. Li, "Adaptive imaging using the generalized coherence factor," IEEE Trans. Ultrason. Ferroelectr. Freq. Control 50(2), 128-141 (2003).

[35] J. Camacho, M. Parrilla, and C. Fritsch, "Phase coherence imaging," IEEE Trans. Ultrason. Ferroelectr. Freq. Control 56(5), 958-974 (2009).

[36] M. A. Lediju, G. E. Trahey, B. C. Byram, and J. J. Dahl, "Short-lag spatial coherence of backscattered echoes: Imaging characteristics," IEEE Trans. Ultrason. Ferroelectr. Freq. Control 58(7), 1377-1388 (2011).

[37] G. Matrone, A. S. Savoia, G. Caliano, and G. Magenes, "The delay multi-ply and sum beamforming algorithm in ultrasound b-mode medical imag-ing," IEEE Trans. Med. Imag. 34(4), 940-949 (2015).

[38] F. Prieur, O. M. H. Rindal, and A. Austeng, "Signal coherence and image amplitude with the filtered delay multiply and sum beamformer," IEEE Trans. Ultrason. Ferroelectr. Freq. Control 65(7), 1133-1140 (2018).

[39] M. R. Morgan, G. E. Trahey, and W. F. Walker, "Multi-covariate imaging of sub-resolution targets," IEEE Trans. Med. Imag. 38(7), 1690-1700 (2019).

[40] R. J. Fedewa, K. D. Wallace, M. R. Holland, J. R. Jago, G. C. Ng, M. R. Rielly, B. S. Robinson, and J. G. Miller, "Spatial coherence of the nonli-nearly generated second harmonic portion of backscatter for a clinical imaging system," IEEE Trans. Ultrason. Ferroelectr. Freq. Control 50(8), 1010-1022 (2003).

[41] J. W. Goodman, Introduction to Fourier Optics (Roberts and Company, Englewood, Colo., 2005).

[42] W. F. Walker and G. E. Trahey, "Speckle coherence and implications for adaptive imaging," J. Acoust. Soc. Am. 101(4), 1847-1858 (1997).

[43] J. A. Jensen and N. B. Svendsen, "Calculation of pressure fields from arbi-trarily shaped, apodized, and excited ultrasound transducers," IEEE Trans. Ultrason. Ferroelectr. Freq. Control 39(2), 262-267 (1992).

[44] J. A. Jensen, "Field: A program for simulating ultrasound systems," in 10th Nordicbaltic Conference on Biomedical Imaging, Citeseer (1996), Vol. 4, Suppl. 1, Part 1, pp. 351-353.

⁴⁵N. B. Bottenus and G. E. Trahey, "Equivalence of time and aperture domain additive noise in ultrasound coherence," J. Acoust. Soc. Am. 137(1), 132-138 (2015).

⁴⁶M. A. Fink and J.-F. Cardoso, "Diffraction effects in pulse-echo meas-urement," IEEE Trans. Son. Ultrason. 31(4), 313-329 (1984).

⁴⁷H. Van Trees, K. Bell, and Z. Tian, Detection Estimation and Modulation Theory, Part I: Detection, Estimation, and Filtering Theory, Detection Estimation and Modulation Theory (Wiley, New York, 2013).

⁴⁸M. A. Richards, Fundamentals of Radar Signal Processing (Tata McGraw-Hill Education, N.Y., 2005).

⁴⁹A. E. A. Blomberg, C.-I. C. Nilsen, A. Austeng, and R. E. Hansen, "Adaptive sonar imaging using aperture coherence," IEEE J. Ocean. Eng. 38(1), 98-108 (2013).

⁵⁰H. Torp, A. Rodriguez-Molares, and L. Lovstakken, "Optimum beam-former strategy for detecting signals in clutter noise," in 2015 IEEE International Ultrasonics Symposium (IUS), (IEEE, Piscataway, N.J., 2015), pp. 1-4.

⁵¹R. Schmidt, "Multiple emitter location and signal parameter estimation," IEEE Trans. Ant. Propag. 34(3), 276-280 (1986).

⁵²B. M. Asl and A. Mahloojifar, "Eigenspace-based minimum variance beamforming applied to medical ultrasound imaging," IEEE Trans. Ultrason. Ferroelectr. Freq. Control 57(11), 2381-2390 (2010).

⁵³F. W. Mauldin, D. Lin, and J. A. Hossack, "The singular value filter: A general filter design strategy for PCA-based signal separation in medical ultrasound imaging," IEEE Trans. Med. Imag. 30(11), 1951-1964 (2011).

⁵⁴C. Demene, T. Deffieux, M. Pernot, B.-F.Osmanski, V. Biran, J.-L. Gennisson, L.-A. Sieu, A. Bergel, S. Franqui, J.-M. Correas, I. Cohen, O. Baud, and M. Tanter, "Spatiotemporal clutter filtering of ultrafast ultra-sound data highly increases Doppler and ultrasound sensitivity," IEEE Trans. Med. Imag. 34(11), 2271-2285 (2015).

⁵⁵J. Capon, "High-resolution frequency-wavenumber spectrum analysis," Proc. IEEE 57(8), 1408-1418 (1969).

⁵⁶O. L. Frost, "An algorithm for linearly constrained adaptive array processing," Proc. IEEE 60(8), 926-935 (1972).

⁵⁷J. Capon, "High-resolution frequency-wavenumber spectrum analysis," Proc. IEEE, vol. 57, no. 8, pp. 1408-1418, August 1969.

⁵⁸O. L. Frost, III, "An algorithm for linearly constrained adap-tive array processing," Proc. IEEE, vol. 60, no. 8, pp. 926-935, August 1972.

⁵⁹J. A. Mann and W. F. Walker, "A constrained adaptive beamformer for medical ultrasound: Initial results," in Proc. IEEE Ultrason. Symp., vol. 2, October 2002, pp. 1807-1810.

⁶⁰M. Sasso and C. Cohen-Bacrie, "Medical ultrasound imaging using the fully adaptive beamformer," in Proc. IEEE Int. Conf. Acoust., Speech, Signal Process. (ICASSP), vol. 2, March 2005, p. ii-489.

⁶¹F. Viola and W. Walker, "Adaptive signal processing in medical ultra-sound beamforming," in Proc. IEEE Ultrason. Symp., vol. 4, September 2005, pp. 1980-1983.

⁶²J.-F. Synnevag, A. Austeng, and S. Holm, "Benefits of minimum-variance beamforming in medical ultrasound imaging," IEEE Trans. Ultrason., Ferroelectr., Freq. Control, vol. 56, no. 9, pp. 1868-1879, September 2009.

⁶³I. K. Holfort, F. Gran, and J. A. Jensen, "Broadband minimum variance beamforming for ultrasound imaging," IEEE Trans. Ultra-son., Ferroelectr., Freq. Control, vol. 56, no. 2, pp. 314-325, February 2009.

⁶⁴C. K. Abbey, N. Q. Nguyen, and M. F. Insana, "Optimal beamforming in ultrasound using the ideal observer," IEEE Trans. Ultrason., Ferroelectr., Freq. Control, vol. 57, no. 8, pp. 1782-1796, August 2010.

⁶⁵C.-I. C. Nilsen and S. Holm, "Wiener beamforming and the coherence factor in ultrasound imaging," IEEE Trans. Ultrason., Ferroelectr., Freq. Control, vol. 57, no. 6, pp. 1329-1346, June 2010.

⁶⁶Y.-H. Wang and P.-C. Li, "SNR-dependent coherence-based adaptive imaging for high-frame-rate ultrasonic and photoacoustic imaging," IEEE Trans. Ultrason., Ferroelectr., Freq. Control, vol. 61, no. 8, pp. 1419-1432, August 2014.

⁶⁷B. Byram, K. Dei, J. Tierney, and D. Dumont, "A model and regulariza-tion scheme for ultrasonic beamforming clutter reduction," IEEE Trans. Ultrason., Ferroelect., Freq. Control, vol. 62, no. 11, pp. 1913-1927, November 2015.

⁶⁸J. Shin and L. Huang, "Spatial prediction filtering of acoustic clutter and random noise in medical ultrasound imaging," IEEE Trans. Med. Imag., vol. 36, no. 2, pp. 396-406, February 2017.

⁶⁹K. B. Petersen et al., "The matrix cookbook," Tech. Univ. Denmark, vol. 7, no. 15, p. 510, 2008.

⁷⁰L. Scharf and C. Demeure, Statistical Signal Processing: Detection, Estimation, and Time Series Analysis (Addison-Wesley Series in Electri-cal and Computer Engineering). Reading, Mass., USA: Addison-Wesley, 1991.

⁷¹H. L. Van Trees, K. L. Bell, and Z. Tian, Detection Estimation and Modulation Theory, Part I: Detection, Estimation, and Filtering Theory. Hoboken, N.J., USA: Wiley, 2013.

⁷²C. L. Lawson and R. J. Hanson, Solving Least Squares Problems, vol. 15. Philadelphia, Pa., USA: SIAM, 1995.

⁷³M. R. Morgan, G. E. Trahey, and W. F. Walker, "Speckle coherence of piecewise-stationary stochastic targets," The Journal of the Acoustical Society of America, vol. 146, no. 3, pp. 1721-1731, September 2019.

That which is claimed is:

1. An ultrasound system for imaging a target, the system comprising:
   a plurality of transducer elements;
   at least one transmitter configured to excite at least one of the transducer elements to emit ultrasound energy to the target;
   a plurality of samplers configured to sample echo signals received by at least some of the plurality of transducer elements, the echo signals comprising acoustic echoes received from the target responsive to the ultrasound energy;
   a coherence calculator configured to calculate a plurality of coherence values, each of the plurality of coherence values corresponding to a measure of similarity between at least two sampled echo signals;
   an estimator configured to estimate a plurality of coherence contribution estimates, each of the plurality of coherence contribution estimates comprising an estimate of a parameter of at least one coherence model applied to the plurality of coherence values; and
   an image generator configured to map at least some of the plurality of coherence contribution estimates from the estimator to respective image locations corresponding to locations in the target and to generate an image of the target based on the at least some of plurality of coherence contribution estimates.

2. The system of claim 1, wherein the estimator is configured to generate estimated contributions of at least one coherence model to the plurality of coherence values using a least squares estimation, maximum likelihood estimation, minimum mean square error (MMSE), maximum posteriori (MAP), minimum variance unbiased (MVUB/MVUE) or Bayes estimators.

3. The system of claim 1, wherein the image generator is configured to generate the image of the target based on the plurality of coherence contribution estimates in an absence of processing beamsummed data.

4. The system of claim 1, wherein the estimator is configured to select the at least one coherence model based on an adaptive coherence estimation.

5. The system of claim 1, wherein the at least one coherence model comprises a spatial covariance model, an angular covariance model and/or a noise model.

6. The system of claim 1, wherein the at least one coherence model comprises a covariance model and each of the plurality of coherence contribution estimates comprises a covariance of the received signals.

7. The system of claim 1, wherein the at least one coherence model comprises a normalized correlation model and each of the plurality of coherence contribution estimates comprises a normalized correlation of the received signals.

8. The system of claim 1, wherein the at least one coherence model comprises a phase difference model and each of the plurality of coherence contribution estimates between any two received signals comprises a phase difference between those received signals.

9. The system of claim 1, wherein the at least one transmitter comprises a plurality of transmitters configured to form a shaped beam within the target.

10. The system of claim 1, wherein the plurality of transducer elements forms one of a linear array, a curved array, a curvilinear array, a 1.25D array, a 1.5D array, a 1.75D array, a 2D array, or an annular array.

11. The system of claim 1, wherein the plurality of transducer elements forms a sparsely sampled array.

12. The system of claim 1, wherein the plurality of transducer elements incorporates elements of varying sizes.

13. The system of claim 1, wherein the system incorporates receive protection circuitry to enable at least one transmit circuit to address at least one array element that is also addressed by at least one sampler.

14. The system of claim 1, wherein the system incorporates a demodulator configured to generate in-phase/quadrature data from received echoes.

15. The system of claim 1, wherein the coherence calculator computes coherences between all possible pairs of sampled signals.

16. The system of claim 1, wherein the coherence calculator computes coherences between a subset of possible pairs of sampled signals.

17. The system of claim 1, wherein signals received from a plurality of portions of the plurality of transducer elements are delayed and summed to yield sub-aperture signals corresponding to some of the plurality of portions of the plurality of transducer elements, and the coherence calculator computes coherences of sub-aperture signals.

18. The system of claim 1, wherein the estimator processes coherence averaged from multiple spatial locations.

19. The system of claim 1, wherein the estimator processes coherence averaged from multiple signal bandwidths.

20. The system of claim 1, wherein the plurality of coherence contribution estimates from a region of interest in the target is estimated from multiple coherences from multiple acquisitions from a same spatial location within the target, but utilizing different transmitter configurations.

21. The system of claim 20 wherein the transmitter configurations correspond to transmission from different portions of the plurality of transducer elements.

22. The system of claim 20 wherein the transmitter configurations utilize different phasing and/or weighting of the plurality of transducer elements.

23. The system of claim 1, wherein the system includes delay elements configured to apply differential delays to the received signals.

24. A method for ultrasound imaging a target, the method comprising:
    exciting at least one of a plurality of transducer elements to emit ultrasound energy to the target;
    sampling echo signals received by at least some of the plurality of transducer elements, the echo signals comprising acoustic echoes received from the target responsive to the ultrasound energy;
    calculating a plurality of coherence values, each of the plurality of coherence values corresponding to a measure of similarity between at least two sampled echo signals;
    estimating a plurality of coherence contribution estimates, each of the plurality of coherence contribution estimates comprising an estimate of a parameter of at least one coherence model applied to the plurality of coherence values;
    mapping at least some of the plurality of coherence contribution estimates from the estimator to respective image locations corresponding to locations in the target; and
    generating an image of the target based on at least some of the plurality of coherence contribution estimates.

25. A computer program product for ultrasound imaging a target, the computer program product comprising: a non-transient computer readable medium having computer readable program code embodied therein, the computer readable program code comprising:
    computer readable program code configured to excite at least one of a plurality of transducer elements to emit ultrasound energy to the target;
    computer readable program code configured to sample echo signals received by at least some of the plurality of transducer elements, the echo signals comprising acoustic echoes received from the target responsive to the ultrasound energy;
    computer readable program code configured to calculate a plurality of coherence values, each of the plurality of coherence values corresponding to a measure of similarity between at least two sampled echo signals;
    computer readable program code configured to estimate a plurality of coherence contribution estimates, each of the coherence contribution estimates comprising an estimate of a parameter of at least one coherence model applied to the plurality of coherence values;
    computer readable program code configured to map at least some of the plurality of coherence contribution estimates from the estimator to respective image locations corresponding to locations in the target; and
    computer readable program code configured to generate an image of the target based on at least some of the plurality of coherence contribution estimates.

26. An ultrasound system for ultrasound analysis on a target, the system comprising:
    a plurality of transducer elements;
    at least one transmitter configured to excite at least one of the transducer elements to emit ultrasound energy to the target;

a plurality of samplers configured to sample echo signals received by at least some of the plurality of transducer elements, the echo signals comprising acoustic echoes received from the target responsive to the ultrasound energy;
a coherence calculator configured to calculate a plurality of coherence values, each of the plurality of coherence values corresponding to a measure of similarity between at least two sampled echo signals;
an estimator configured to estimate a plurality of coherence contribution estimates, each of the plurality of coherence contribution estimate comprising an estimate of a parameter of at least one coherence model applied to the plurality of coherence values; and
a filter generator configured to modify the echo signals based on at least some of the plurality of coherence contribution estimates from the estimator and to optionally further process the filtered echo signals using B-mode imaging, Doppler ultrasound, flow estimation, speckle tracking, elastography or strain imaging, displacement estimation, acoustic radiation force-based methods, phase or aberration correction and/or tissue characterization.

* * * * *